(12) United States Patent
Weissenbach et al.

(10) Patent No.: US 6,924,126 B1
(45) Date of Patent: Aug. 2, 2005

(54) CLONING, EXPRESSION AND CHARACTERIZATION OF THE SPG4 GENE RESPONSIBLE FOR THE MOST FREQUENT FORM OF AUTOSOMAL SPASTIC PARAPLEGIA

(75) Inventors: Jean Weissenbach, Paris (FR); Jamilé Hazan, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 42 days.

(21) Appl. No.: 09/830,902

(22) PCT Filed: Sep. 4, 2000

(86) PCT No.: PCT/FR00/02433

§ 371 (c)(1),
(2), (4) Date: Oct. 19, 2001

(87) PCT Pub. No.: WO01/18198

PCT Pub. Date: Mar. 15, 2001

(30) Foreign Application Priority Data

Sep. 3, 1999 (FR) .............................. 99/11097

(51) Int. Cl.⁷ ............................................... C12P 19/34
(52) U.S. Cl. ................... 435/91.2; 536/23.1; 536/24.33
(58) Field of Search .................. 435/91.2; 536/23.1, 536/24.33, 24.31; 514/44

(56) References Cited

PUBLICATIONS

R. Kikuno et al, "Prediction of the Coding Sequences of Unidentified Human Genes. XIV. The Complete Sequences of 100 cDNA Clones From Brain for Large Proteins in Vitro.", *DNA RES*, Jun. 30, 1999, vol. 6, pp. 197–205 [XP000852618].

R.M. Myers, "Human STS SHGC–44567", Database EMBL Sequences 'Online!, Accession No. HS1179930, Mar. 29, 1997 [XP002156510].

J. Hazan et al, "Spastin, a New AAA Protein, is Altered in the Most Frequent Form of Autosomal Dominent Spastig Paraplegia", *Nat. Genet.*, Nov. 1999, vol. 23, pp. 296–303 [XP000914979].

O. Heinzlef et al, "Mapping of a Complicated Familial Spastic Paraplegia to Locus SPG4 on Chromosome 2p", *J. Med. Genet.*, Feb. 1998, vol. 35, No. 2, pp. 89–93 [XP000914971].

*Primary Examiner*—Dave Trong Nguyen
*Assistant Examiner*—Celine Qian
(74) *Attorney, Agent, or Firm*—Burns, Doane, Swecker & Mathis, LLP

(57) ABSTRACT

The invention concerns the identification and characterization of the SPG4 gene encoding spastin, and some mutations thereof responsible for the most frequent form of autosomal dominant familial spastic paraplegia, to the cloning and characterization of its cDNA and the corresponding polypeptides. The invention also concerns vectors, transformed cells and transgenic animals as well as diagnostic methods and kits, and methods for selecting a chemical or biological compound capable of directly or indirectly interacting with said polypeptide.

31 Claims, 7 Drawing Sheets

FIGURE 1A
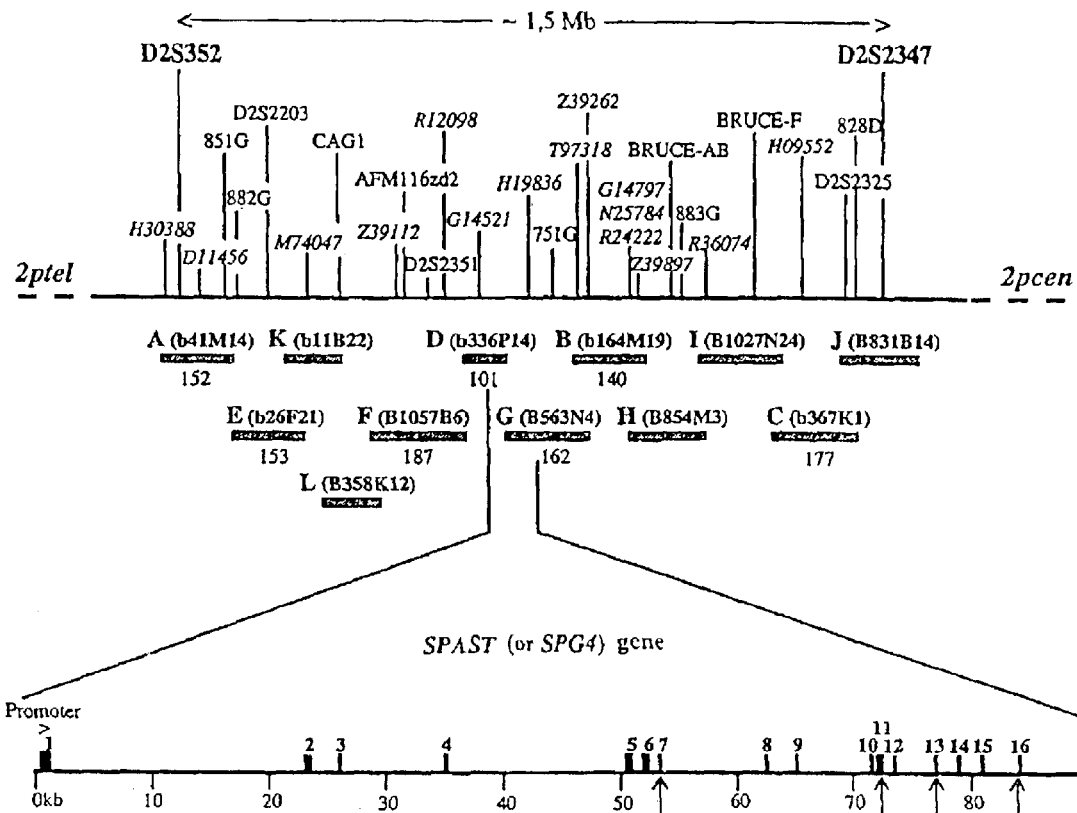
FIGURE 1B
FIGURE 1C
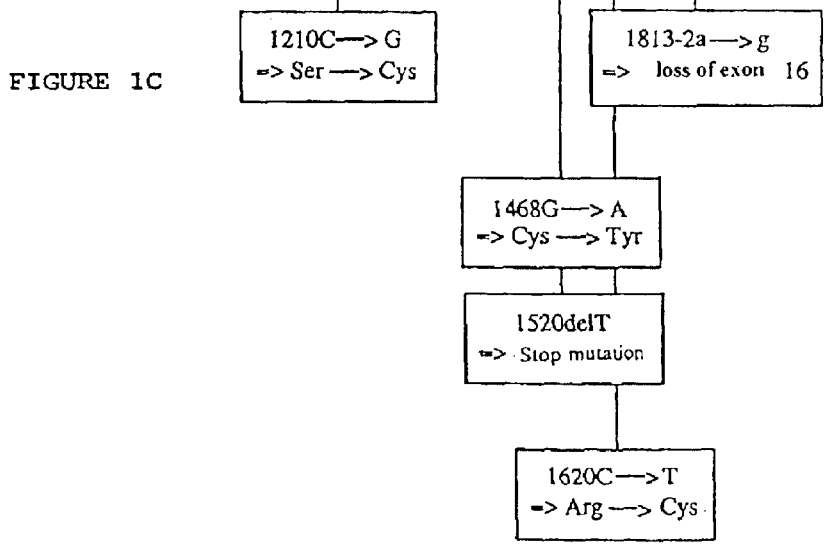

```
   GCTCCTGAGACCGGCGGGCACACGGGGGTCTGTGGCCCCCGCCGTAGCAGTGGCTGCCGCCGTCGCTTGGTTCCCGTCGGTCTGCGGGAGGCGGG    95
 1 TTATGGCGGCGGCGGCAGTGAGAGCTGTGAATGAATTCTCCGGGTGGACGAGGGAAGAAGAAAGGCTCCGGCGGCGGCCAGCAACCCGGTGCCTCC   190
                       M  N  S  P  G  G  R  G  K  K  K  G  S  G  G  A  S  N  P  V  P  P
   CAGGCCTCCGCCCCCTTGCCTGGCCCCCGCCCCTCCCGCCGCCGGGCCGGCCCCTCCGCCCGAGTCGCCGCATAAGCGGAACCTGTACTATTTCT   285
23  R  P  P  P  C  L  A  P  A  P  P  A  A  G  P  A  P  P  P  E  S  P  H  K  R  N  L  Y  Y  F  S
   CCTACCCGCTGTTTGTAGGCTTCGCGCTGCTGCGTTTGGTCGCCTTCCACCTGGGGCTCCTCTTCGTGTGGCTCTGCCAGCGCTTCTCCGCGCC    380
55    Y  P  L  F  V  G  F  A  L  L  R  L  V  A  F  H  L  G  L  L  F  V  W  L  C  Q  R  F  S  R  A
   CTCATGGCAGCCAAGAGGAGCTCCGGGGCCGCGGCAGCACCTGCCTCGGCCTGGCCCCGGCGCCGGTGCCGGGCGGCGAGGCCGAGCGCGTCCG    475
86   L  M  A  A  K  R  S  S  G  A  A  P  A  P  A  S  A  S  A  P  A  P  V  P  G  G  E  A  E  R  V  R
   AGTCTTCCACAAACAGGCCTTCGAGTACATCTCCATTGCCCTGCGCATCGATGAGGATGAGAAGCAGGACAGAAGGAGCAAGCTGTGGAATGGT    570
118   V  F  H  K  Q  A  F  E  Y  I  S  I  A  L  R  I  D  E  D  E  K  A₂G  Q  K  E  Q  A  V  E  W  Y
   ATAAGAAAGGTATTGAAGAACTGGAAAAAGGAATAGCTGTTATAGTTACAGGACAAGGTGAACAGTGTGAAAGAGCTAGACGCCTTCAAGCTAAA    665
150   K  K  G  I  E  E  L  E  K  G  I  A  V  I  V  T  G  Q  G₃E  Q  C  E  R  A  R  R  L  Q  A  K
   ATGATGACTAATTTGGTTATGGCCAAGGACCGCTTACAACTTCTAGAGAAGATGCAACCAGTTTTGCCATTTTCCAAGTCACAAACGGACGTCTA   760
181   M  M  T  N  L  V  M  A  K  D  R  L  Q  L  L  E₄K  M  Q  P  V  L  P  F  S  K  S  Q  T  D  V  Y
   TAATGACAGTACTAACTTGGCATGCCGCAATGGACATCTCCAGTCACAAAGTGGAGCTGTTCCAAAAAGAAAAGACCCCTTAACACACACTAGTA   855
213   N  D  S  T  N  L  A  C  R  N  G  H  L  Q  S  E₅S  G  A  V  P  K  R  K  D  P  L  T  H  T  S  N
   ATTCACTGCCTCGTTCAAAAACAGTTATGAAAACTGGATCTGCAGGCCTTTCAGGCCACCATAGAGCACCTAGTTACAGTGGTTTATCCATGGT    950
245    S  L  P  R  S  K  T  V  M  K  T  G  S  A  G  L₆S  G  H  H  R  A  P  S  Y  S  G  L  S  H  V
   TCTGGAGTGAAACAGGGATCTGGTCCTGCTCCTACCACTCATAAGGTACTCCGAAACAAATAGGACAAATAAACCTTCTACCCCTACAACTGC  1045
276   S  G  V  K  Q  G  S  G  P  A  P  T  T  H  K  G₆T  P  K  T  N  R  T  N  K  P  S  T  P  T  T  A
   TACTCGTAAGAAAAAAGACTTGAAGAATTTTTAGGAATGTGGACAGCAACCTTGCTAACCTTATAATGAATGAAATTGTGGACATTGGAACAGCTG  1140
308   T  R  K  K  K  D  L  K  N  F  R  N  V  D  S  H  L  A  N  L  I  M  N  E  I  V  D  N  G₇T  A  V
   TTAAATTTGATGATATAGCTGGTCAAGACTTGGCAAAACAAGCATTGCAAGAAATTGTTATTCTTCCTCTCTGAGGCCTGACTTGTTCACAGGG  1235
340   K  F  D  D  I  A  G  Q  D  L  A  K  Q  A  L  Q  E  I  V  I  L  P  S  L  R  P  E  L₈F  T  G
   CTTAGAGCTCCTGCCAGAGGGCTTGTTACTCTTTGGTCGCACCTGGGAATGGAAGACAATGCTGCTAAAGCAGTAGCTGCAGAATCGAATGCAAC  1330
371   L  R  A  P  A  R  G  L  L  L  F  G  P  P  G  N  G  K  T  M  L  A₉K  A  V  A  A  E  S  N  A  T
   CTTCTTTAATATAAGTGCTGCAAGTTTAACTTCAAAATACGTGGGAGAAGGAGAGAAATTGGTGAGGGCTCTTTTTGCTGTGGCTCGAGAACTTC  1425
403   F  F  N  I  S  A  A  S  L  T  S  K  Y  V₁₀G  E  G  E  K  L  V  R  A  L  F  A  V  A  R  E  L  Q
   AACCTTCTATAATTTTTATAGATGAAGTTGATAGCCTTTTGTGTGAAAGAAGAGAAGGGGAGCACGATGCTAGTAGACGCCTAAAAACTGAATTT  1520
435   P  S  I  I  F  I  D₁₁E  V  D  S  L  L  C  E  R  R  E  G  E  H  D  A  S  R  R  L  K  T  E  F
   CTAATAGAATTTGATGGTGTACAGTCTGCTGGAGATGACAGATACTTGTAATGGGTGCAACTAATAGGCCACAAGAGCTTGATGAGGCTGTTCT  1615
466   L  I  E  F  D  G  V₁₂Q  S  A  G  D  D  R  V  L  V  H  G  A  T  N  R  P  Q  E  L  D  E  A  V  L
   CAGGCGTTTCATCAAACGGGTATATGTGTCTTTACCAAATGAGGAGCAAGACTACTTTTGCTTAAAAATCTGTTATGTAAACAAGGAAGTCCAT  1710
498   R₁₃R  F  I  K  R  V  Y  V  S  L  P  N  E  E  T₁₄R  L  L  L  L  K  N  L  L  C  K  Q  G  S  P  L
   TGACCCAAAAAGAACTAGCACAACTTGCTACAATGACTGATGGATACTCAGGAAGTGACCTAACAGCTTTGGCAAAAGATGCAGCACTGGGTCCT  1805
530    T  Q  K  E  L  A  Q  L  A  R  M₁₅T  D  G  Y  S  G  S  D  L  T  A  L  A  K  D  A  A  L  G  P
   ATCCGAGAACTAAAACCAGAACAGGTGAAGAATATGTCTGCCAGTGAGTGAAATATTCGATTATCTGACTTCACTGAATCCTTGAAAAAAAT    1900
561   I  R  E₁₆L  K  P  E  Q  V  K  N  M  S  A  S  E  M₁₇R  N  I  R  L  S  D  F  T  E  S  L  K  K  I
   AAAACGCAGCGTCAGCCCTCAAACTTTAGAAGCGTACATACGTTGGAACAAGGACTTTGGAGATACCACTGTTTAAGGAAATACCCTTTGTAAACC  1995
593   K  R  S  V  S  P  Q  T  L  E  A  Y  I  R  W  N  K  D  F  G  D  T  T  V  *
   TGCAGAACATTTTACTTAAAAGAGGAAACACAAGATCTTCAATGAACGTCATCGGCTACAGAAACAGCCTAAGTTTACAGGACTTTTTAGAGTCT 2090
   TACATATTTGTGCACCAAACTTGAAGATGAACCAGAAAACAGACTTAAACAAAATATACAATGCAAATGTAATTTTTTGTTGTTTAAGGCCTTGC 2185
   CTTGATGGTCACAGTTATCCCAATGGACACTAAGTTAGAGCACAACAAAACCTGATTCTGGTCTTCTTTACCAATATAATCATAATGTAAATAAT 2280
   AATTTGTATATTGTGTTGCAGATGAAAGTATTCCAGGAACAGTGAATGGTAGAAGACACAAGAACATTTGTTTGTTTGTCTTCTGATGTTTTTTC 2375
   TTAAAATAGTAATTTCTCCTACTTTTCTTTTCTACTGTTGTCTTAACTACAGGTGATTGGAATGCCAAACACTCTTAAGTTTATTTTCTTTTTTC 2470
   GTTTTATAAATTCAGTGTGCCAAATGAAACTTTTTTCCTAAGTAACTGTAATAGGAAAAAGTTTATTTTGAGAGTTTCTTCTTCATAAATCTACA 2565
   GACATTAAACAATTGTTGTGTTCTTTTTACCTTTTATTTTTCTATTACCTTGCTACCAAACAGTTTAGATAGCAATATAATAGCAAAAAGCAAA 2660
   TATGGTAAAATAGAGAAGGTTTGAAGGTTTGAGTTACTCTGTCATATAACATGTAGATCAGTCTTCATGTGACCTGCAGTATTTTTTTTCTAAT 2755
   GTATTTGTCAGAAATCTGTTGTAGACTGTTAACTTCTTCCTGATGGAATTTATTTTCTGCAAGAATTATTCTGATATTTAAGAGAGCCAATTTTA 2850
   ACTGCTGTCAAAATGTTTCCAGTGCAAGAGAAGGGAAATACTAGGAACTACAACATTTCTAATTTATTGCTTATTACTTTCTTAATTTTACAGGA 2945
   TAATTATAAGCAAGTGGAACTACCATCTTTTATTCTTAATAATTATTAATCCCTTCAATGAAACTTTAAAAAAACTGAATTTTTATACATGGCAT 3040
   ACATTTTTCTAGTTCCTTCTGCTTGCTTTATTAACTCAAAAGTTCTAGTTCTAGTCTGTTGATCTGCCTTTTGTTCTCCCAAAATGTACAGTAAT 3135
   TCCATTTGTTTGTATAAATATGCCTGGATTTTCATTATAAAAATGTCATTGTAGGGAGTAGAGACTCATATCATGGCCTTTTAAATATTGTAATA 3230
   AAGGCAAATAGATATTTGCCCTTAGTTTACTGG 3263
```

CLONING, EXPRESSION AND CHARACTERIZATION OF THE SPG4 GENE RESPONSIBLE FOR THE MOST FREQUENT FORM OF AUTOSOMAL SPASTIC PARAPLEGIA

BACKGROUND OF THE INVENTION

1. Field of Invention

The invention relates to the identification and characterization of the SPG4 gene encoding spastin, which is responsible for the most common form of autosomal dominant hereditary spastic paraplegia (HSP), to the cloning and characterization of its cDNA, and also to the corresponding polypeptides. The invention also relates to vectors, to transformed cells and to transgenic animals, and also to diagnostic methods and kits and to methods for selecting a chemical or biochemical compound capable of interacting directly or indirectly with a polypeptide according to the invention.

2. Background of the Invention

Hereditary spastic paraplegias (HSPs) are degenerative disorders of the central nervous system, characterized by bilateral and progessive spasticity of the lower limbs. They reveal themselves clinically through difficulties in walking possibly evolving into total paralysis of both legs. The physiopathology of this set of diseases is, to date, relatively undocumented; however, anatomopathological data make it possible to conclude that the attack is limited to the pyramidal tracts responsible for voluntary motricity in the spinal cord (Reid, 1997). Various clinical and genetic forms of HSP exist. The so-called "pure" HSPs, which correspond to isolated spasticity of the lower limbs, are clinically distinguished from the "complex" HSPs, for which the spasticity of the legs is associated with other clinical signs of neurological or non-neurological type (Bruyn et al., 1991). From a genetic point of view, the HSPs can be transmitted according to the autosomal dominant (AD-HSP), autosomal recessive (AR-HSP) or X-linked (X-HSP) mode. The "pure" form of HSP, which is most commonly transmitted according to the autosomal dominant mode, remains the most frequent (approximately 80% of HSPs) (Reid, 1997). The incidence of HSPs, which remains difficult to estimate because of rare epidemiological studies and the considerable clinical variability, varies from 0.9:100 000 in Denmark, 3 to 9.6:100 000 in certain regions of Spain (Polo et al., 1991) or 14:100 000 in Norway (Skre, 1974) (approximately 3:100 000 in France).

In addition to this great clinical variability, which is observed not only between various families but also between various affected members of the same family, the HSPs are also characterized by considerable genetic heterogeneity. In the case of AD-HSPs, four loci have been identified, to date, on chromosomes 14 (locus SPG3) (Hazan et al., 1993), 2 (locus SPG4) (Hazan et al., 1994; Hentali et al., 1994), 15 (locus SPG6) (Fink et al., 1995) and 8 (locus SPG8) (Hedera et al., 1999). The study of a large number of families exhibiting an AD-HSP has shown that the gene carried by chromosome 2 is a main locus of this form of the disease, found in 40 to 50% of the families analyzed (The Hereditary Spastic Paraplegia Working Group, 1996; Durr et al., 1996). An anticipation phenomenon was observed in some locus SPG4-linked HSP families; this phenomenon has, subsequently, been associated with the expansion of a (CAG)n repeat demonstrated in 6 Danish families (Nielsen et al., 1997) using the RED (for Rapid Expansion Detection) technique. It has, however, never been possible to confirm this expansion in any of the families tested by this method or by the systematic search for sequences of (CAG)n type in physical maps composed of YAC (for Yeast Artificial Chromosome) or BAC (for Bacterial Artificial Chromosome) clones (Hazan et al., Genomics, 60 (3), 309–19, 1999).

To date, three genes responsible for two forms of X-HSP and one form of AR-HSP have been identified. Mutations in the gene which encodes a neuron-specific cell adhesion molecule, L1-CAM (for L1 Cell Adhesion Molecule), and which is located at Xq28 (locus SPG1) cause a complex form of HSP (Jouet et al., 1994) in which the spasticity is associated with a mental handicap, whereas mutations in the PLP (for ProteoLipid Protein) gene located at Xq21 (locus SPG2), which encodes a constitutive molecule of the myelin layer, cause pure and complex forms of X-HSP (Saugier-Veber, P. et al., 1994). More recently, mutations in the gene located at 16q24.3 (locus SPG7), which encodes paraplegin, a mitochondrial ATPase of the AAA (for "ATPases Associated with diverse cellular Activities") protein family (Confalonieri et al., 1995), have been associated with complex and pure forms of AR-HSP (Casari et al., 1998).

Thus, there remains, today, a great need to identify and characterize the gene responsible for the most common form of AD-HSP. The identification of this gene should, in particular, allow, besides the possibility of a test for antenatal screening in the families concerned, a better understanding of some of the molecular mechanisms engendering these degenerations specific for nerve bundles of the spinal cord, or even make it possible to provide an elementary response regarding therapeutic treatment for the patients.

SUMMARY OF THE INVENTION

This is precisely the subject of the present invention.

After having delimited the localization range between the D2S352 and D2S2347 genetic markers by studying recombination events in locus SPG4-linked HSP families, the inventors have established a contig of BACs covering a physical distance evaluated at approximately 1.5 Mb and have undertaken a positional cloning strategy based on sequencing the SPG4 range in order to completely identify all the genes located in the candidate region. The analysis of the sequence of the two BACs, D (b336P14) and G (B763N4), has revealed the presence of a gene which is composed of 17 exons, extending over a distance of approximately 100 kb, and which exhibits homology with the genes encoding proteins of the AAA family. Comparison of the sequence of this gene between the healthy and affected individuals of AD-HSP families has made it possible to demonstrate various mutations in the patients.

A subject of the invention is thus the identification and characterization of the SPG4 (or SPAST) gene encoding a novel nuclear member of the AAA family, responsible for the most common form of AD-HSP.

In a first aspect, a subject of the present invention is a purified or isolated nucleic acid of the SPG4 gene, characterized in that it comprises at least 15 consecutive nucleotides, preferably 20, 25, 30, 35, 40, 45, 50, 75, 100 or 200 consecutive nucleotides, of a sequence chosen from the group comprising:

the sequence SEQ ID No. 1, which is a genomic sequence of the human SPG4 gene;

the nucleic acid sequences which are homologs or variants of the nucleic acid of sequence SEQ ID No. 1;

the sequence which is complementary thereto; and the sequence of the corresponding RNA thereof.

The present invention relates, of course, to both the DNA and RNA sequences, and also the sequences which hybridize with them, as well as the corresponding double-stranded DNAs.

The terms "nucleic acid", "nucleic acid sequence" or "sequence of nucleic acid", "polynucleotide", "oligonucleotide", "polynucleotide sequence", and "nucleotide sequence", which will be used equally in the present description, will be intended to refer to both a double-stranded DNA, a single-stranded DNA and products of transcription of said DNAs, and/or an RNA fragment, said isolated natural, or synthetic fragments which may or may not include unnatural nucleotides, referring to a precise series of nucleotides, which may or may not be modified, making it possible to define a fragment or a region of a nucleic acid. The expression "natural isolated, or synthetic DNA and/or RNA fragment, which may or may not include unnatural nucleotides" is intended to mean a precise series of nucleotides, which may or may not be modified, making it possible to define a fragment, a segment or a region of a nucleic acid.

It should be understood that the present invention does not relate to the genomic nucleotide sequences in their natural chromosomal environment, i.e. in the natural state. It involves sequences which have been isolated and/or purified, i.e. they have been removed directly or indirectly, for example by copying, their environment having been at least partially modified.

The term "homologous nucleic acid sequence" is intended to refer to the sequences which have, with respect to the reference nucleic acid sequence, certain modifications, such as in particular a deletion, a truncation, an extension, a chimeric fusion and/or a mutation, in particular a point mutation, and the nucleic acid sequence of which shows at least 80%, preferably 90% or 95%, identity after alignment, with the reference nucleic acid sequence.

For the purpose of the present invention, the term "percentage of identity" between two nucleic acid or amino acid sequences is intended to refer to a percentage of nucleotides or of amino acid residues which are identical between the two sequences to be compared, obtained after the best alignment, this percentage being purely statistical and the differences between the two sequences being distributed randomly and throughout their length. Sequence comparisons between two nucleic acid or amino acid sequences are traditionally carried out by comparing these sequences after having optimally aligned them, said comparison being carried out by segment or by "window of comparison" in order to identify and compare local regions of sequence similarity. The optimal alignment of the sequences for comparison can be produced, besides manually, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444], and by means of computer programs using these algorithms (GAP, BESTFIT, FASTA and TFASTA in the Wisconsin Genetics Software Package, Genetics Computer Group, 575 Science Dr., Madison, Wis., or with the BLAST N or BLAST P comparison programs).

The percentage of identity between two nucleic acid or amino acid sequences is determined by comparing these two optimally aligned sequences by window of comparison in which the region of the nucleic acid or amino acid sequence to be compared can comprise additions or deletions with respect to the reference sequence for optimal alignment between these two sequences. The percentage of identity is calculated by determining the number of identical positions for which the nucleotide or the amino acid residue is identical between the two sequences, dividing this number of identical positions by the total number of positions in the window of comparison and multiplying the result obtained by 100 so as to obtain the percentage of identity between these two sequences.

For example, the BLAST program "BLAST 2 sequences" (Tatusova et al., "Blast 2 sequences—a new tool for comparing protein and nucleotide sequences", FEMS Microbiol. Lett. 174:247–250), available on the National Institutes of Health Website, may be used, the parameters used being those given by default (in particular for the parameters "open gap penalty": 5, and "extension gap penalty": 2; the matrix chosen being, for example, the "BLOSUM 62" matrix proposed by the program), the percentage of identity between the two sequences to be compared being calculated directly by the program.

It preferably involves sequences for which the complementary sequences are capable of hybridizing specifically with one of the sequences of the invention. Preferably, the specific or high stringency hybridization conditions will be such that they ensure at least 80%, preferably 90% or 95%, identity after alignment between one of the two sequences and the sequence which is complementary to the other.

Hybridization under high stringency conditions means that the temperature and ionic strength conditions are chosen such that they allow the hybridization between two complementary DNA fragments to be maintained. By way of illustration, high stringency conditions of the hybridization step for the purposes of defining the polynucleotide fragments described above are advantageously as follows.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SDS), 10× Denhardt's, 5% of dextran sulfate and 1% of salmon sperm DNA; (2) actual hybridization for 20 hours at a temperature dependent on the size of the probe (i.e. 42° C. for a probe of size >100 nucleotides), followed by two 20-minute washes at 20° C. in 2×SSC+2% SDS and one 20-minute wash at 20° C. in 0.1×SSC+0.1% SDS. The final wash is carried out in 0.1×SSC+0.1% SDS for 30 minutes at 60° C. for a probe of size >100 nucleotides. The high stringency hybridization conditions described above for a polynucleotide of defined size will be adjusted by those skilled in the art for oligonucleotides of greater or smaller size, according to the teaching of Sambrook et al., 1989.

The term "nucleic acid sequence which is a variant" or "nucleic acid which is a variant" of a reference nucleic acid sequence will be intended to refer to the set of nucleic acid sequences corresponding to allelic variants, i.e. individual variations of the reference nucleic acid sequence. These natural mutated sequences correspond to polymorphisms present in mammals, in particular in human beings, and in particular to polymorphisms which can cause a pathology to occur and/or to develop.

While the sequences according to the invention relate to normal sequences, they also relate to sequences which are mutated insofar as they include at least one point mutation, and preferably at most 10% of mutations, with respect to the normal sequence.

In particular, the variant nucleic acid sequences will comprise any sequence of at least 15 consecutive nucleotides, preferably 20, 25, 30, 50, 100 or 200 consecutive nucleotides, of a polymorphic sequence of the genomic sequence of the human SPG4 gene of sequence SEQ ID No. 1, and the nucleic acid sequence of which has, with respect to the sequence SEQ ID No. 1, at least one mutation corresponding in particular to a truncation, deletion, substitution and/or addition of an amino acid residue. In the present case, the variant nucleic acid sequences having at least one mutation will herein be linked to the pathologies of AD-HSP type linked to SPG4 locus.

Preferably, the present invention relates to the mutated nucleic acid sequences in which the mutations produce a modification of the amino acid sequence of the polypeptide encoded by the normal sequence.

The term "variant nucleic acid sequences" will also be intended to refer to any RNA or cDNA resulting from a mutation of a splice site of the genomic nucleic acid sequence SEQ ID No. 1.

Preferably, the invention relates to a purified or isolated nucleic acid of the SPG4 gene according to the invention, characterized in that it comprises a sequence chosen from the group comprising:

a) the sequence SEQ ID No. 1, the sequence SEQ ID No. 2, the sequence SEQ ID No. 72, the sequence SEQ ID No. 106 or the sequence of at least 15, preferably 20, 25, 30, 35, 40, 45, 50, 75, 100 or 200, consecutive nucleotides of the sequence SEQ ID No. 1, SEQ ID No. 2, SEQ ID No. 72 or SEQ ID No. 106;

b) the nucleic acid sequences which are homologs or variants of the sequences SEQ ID No. 1, SEQ ID No. 2, SEQ ID No. 72 or SEQ ID No. 106; and c) the complementary sequence or the RNA sequence corresponding to the sequences as defined in a) and b), preferably with the exception of the nucleic acid identified in the GenBank database under the accession number AB029006.

The nucleic acid the sequence of which is disclosed in the GenBank database under the accession number AB029006 corresponds to the sequence of one of the 100 cDNAs derived from a human brain mRNA library identified by the Kazusa DNA Research Institute in Japan (Kikuno et al., DNA Resarch, 6, 197–205, 1999).

Preferably, the invention relates to a purified or isolated nucleic acid according to the invention, characterized in that it comprises at least one sequence of at least 15 consecutive nucleotides, preferably 20, 25, 30. 50 or 75 consecutive nucleotides, of the nt 714–809, ends inclusive, fragment of the sequence SEQ ID No. 2, of the sequence complementary thereto or of the sequence of the corresponding RNA thereof.

The invention preferably relates to a purified or isolated nucleic acid according to the present invention, characterized in that it comprises a sequence chosen from the following group:

the sequence SEQ ID No. 1;

the sequence SEQ ID No. 2, which is the cDNA sequence encoding human spastin;

the sequences SEQ ID No. 72 and SEQ ID No. 106, the sequence SEQ ID No. 72 representing the sequence of the incomplete cDNA encoding murine spastin represented in FIG. 5, "mouse" line, and the SEQ ID No. 106 representing the complete sequence thereof;

the nucleic acid sequences which are homologs or variants of the sequences SEQ ID No. 1, SEQ ID No. 2, SEQ ID No. 72 or SEQ ID No. 106;

the sequence complementary thereto; and the sequence of the corresponding RNA thereof.

Preferably, the invention relates to a purified or isolated nucleic acid according to the invention, characterized in that it comprises at least one mutation which corresponds to a natural polymorphism in humans, in particular the position and nature of which are identified in Table 5.

The primers or probes, characterized in that they comprise a sequence of a nucleic acid according to the invention, also form part of the invention.

The present invention thus relates to the set of primers which can be deduced from the nucleotide sequences of the invention and which may make it possible to demonstrate said nucleotide sequences of the invention, in particular the mutated sequences, using in particular an amplification method such as the PCR method, or a related method.

The present invention also relates to the set of probes which can be deduced from the nucleotide sequences of the invention, in particular from the sequences capable of hybridizing with them, and which may make it possible to demonstrate said nucleotide sequences, in particular to distinguish the normal sequences from the mutated sequences.

The present invention relates, in particular, to the probes or primers having sequences chosen from the sequences SEQ ID No. 4 to SEQ ID No. 71.

The invention also relates to the use of a nucleic acid sequence according to the invention as a probe or primer, for detecting, identifying, assaying or amplifying a nucleic acid sequence.

According to the invention, the polynucleotides which can be used as a probe or as a primer in processes for detecting, identifying, assaying or amplifying a nucleic acid sequence will have a minimum size of 15 bases, preferably of 20 bases, or better still of 25 to 30 bases.

The set of probes and primers according to the invention may be labeled directly or indirectly with a radioactive or nonradioactive compound, using methods well known to those skilled in the art, in order to obtain a detectable and/or quantifiable signal.

The nonlabeled polynucleotide sequences according to the invention can be used directly as a probe or primer.

The sequences are generally labeled so as to obtain sequences which can be used for many applications. The labeling of the primers or of the probes according to the invention is carried out with radioactive elements or with nonradioactive molecules.

Among the radioactive isotopes used, mention may be made of $^{32}P$, $^{33}P$, $^{35}S$, $^{3}H$ or $^{125}I$. The nonradioactive entities are selected from ligands, such as biotin, avidin or streptavidin, dioxygenin, haptens, colorants and luminescent agents, such as radioluminescent, chemiluminescent, bioluminescent, fluorescent or phosphorescent agents.

The polynucleotides according to the invention can thus be used as a primer and/or probe in processes using, in particular, the PCR (polymerase chain reaction) technique (Erlich, 1989; Innis et al., 1990, and Rolfs et al., 1991). This technique requires choosing pairs of oligonucleotide primers framing the fragment which must be amplified. Reference may, for example, be made to the technique described in American patent U.S. Pat. No. 4,683,202. The amplified fragments can be identified, for example after agarose or polyacrylamide gel electrophoresis, or after a chromatographic technique such as gel filtration or ion exchange chromatography, and then sequenced. The specificity of amplification can be controlled using, as a primer, the nucleotide sequences of polynucleotides of the invention and, as a matrix, plasmids containing these sequences or the derived amplification products. The amplified nucleotide fragments can be used as reagents in hybridization reactions in order to demonstrate the presence, in a biological sample, of a target nucleic acid having a sequence complementary to that of said amplified nucleotide fragments.

The invention is also directed toward the nucleic acids which can be obtained by amplification using primers according to the invention.

Other techniques for amplifying the target nucleic acid can be advantageously employed as an alternative to PCR (PCR-like), using pairs of primers having nucleotide sequences according to the invention. The term "PCR-like" will be intended to refer to all methods using direct or indirect reproductions of nucleic acid sequences, or in which the labeling systems have been amplified. These techniques are, of course, known. In general, they involve amplifying the DNA with a polymerase; when the sample of origin is an RNA, it is advisable to perform reverse transcription beforehand. There are, currently, a great many processes which enable this amplification, such as for example the SDA (Strand Displacement Amplification) technique (Walker et al., 1992), the TAS (Transcription-based Amplification System) technique described by Kwoh et al. in 1989, the 3SR (Self-Sustained Sequence Replication) technique described by Guatelli et al. in 1990, the NASBA (Nucleic Acid Sequence Based Amplification) technique described by Kievitis et al. in 1991, the TMA (Transcription Mediated Amplification) technique, the LCR (Ligase Chain Reaction) technique described by Landegren et al. in 1988 and improved by Barany et al. in 1991, which uses a heat-stable ligase, the RCR (Repair Chain Reaction) technique described by Segev in 1992, the CPR (Cycling Probe Reaction) technique described by Duck et al. in 1990, and the Q-beta-replicase amplification technique described by Miele et al. in 1983 and improved, in particular, by Chu et al. in 1986 and Lizardi et al. in 1988, and then by Burg et al., and also by Stone et al., in 1996.

When the target polynucleotide to be detected is an mRNA, use will advantageously be made, prior to carrying out an amplification reaction using the primers according to the invention or carrying out a detection process using the probes of the invention, of an enzyme of reverse transcriptase type in order to obtain a cDNA from the mRNA contained in the biological sample. The cDNA obtained will then serve as a target for the primers or probes used in the amplification or detection process according to the invention.

The probe hybridization technique can be carried out in diverse ways (Matthews et al., 1988). The most general method consists in immobilizing the nucleic acid extracted from the cells of various tissues or from cells in culture, on a support (such as nitrocellulose, nylon or polystyrene), and in incubating the immobilized target nucleic acid with the probe, under well defined conditions. After hybridization, the excess probe is eliminated and the hybrid molecules formed are detected using the appropriate method (measurement of the radioactivity, of the fluorescence or of the enzymatic activity linked to the probe).

According to another embodiment of the nucleic acid probes according to the invention, the latter can be used as a capture probe. In this case, a probe, termed "capture probe", is immobilized on a support and is used to capture, by specific hybridization, the target nucleic acid obtained from the biological sample to be tested, and the target nucleic acid is then detected using a second probe, termed "detection probe", labeled with an easily detectable element.

The splice acceptor or donor site sequences according to the present invention identified in Table 3 (sequences SEQ ID No. 74 to SEQ ID No. 105) also form part of the present invention.

In another aspect, the invention comprises a method for screening cDNA or genomic DNA libraries, or for cloning isolated genomic or cDNA encoding spastin, characterized in that it uses a nucleic acid sequence according to the invention.

Among these methods, mention may be made in particular of:

the screening of cDNA libraries and the cloning of the isolated cDNAs (Sambrook et al., 1989; Suggs et al., 1981; Woo et al., 1979), using the nucleic acid sequences according to the invention;

the screening of genomic libraries, for example of BACs (Chumakov et al., 1992; Chumakov et al., 1995), and, optionally, a genetic analysis by FISH (Cherif et al., 1990), using sequences according to the invention, enabling the isolation and chromosomal localization, and then the complete sequencing, of the SPG4 gene encoding spastin.

In particular, these methods according to the invention may be used for identifying and thus obtaining the genomic sequence or the cDNA of the SPG4 gene in other mammals, in particular mice.

These screening and/or cloning methods will comprise, in particular, a step of hybridization of a nucleic acid according to the invention with a nucleic acid contained in a genomic or cDNA library.

The invention also comprises a method for identifying the nucleic acid sequences which promote and/or regulate the expression of the SPG4 gene of sequence SEQ ID No. 1, characterized in that it uses a nucleic acid according to the invention.

The computer tools available to those skilled in the art enable them to easily identify, using the genomic nucleic acid sequences according to the invention, the promoter regulatory boxes required and sufficient for controlling gene expression, in particular the TATA, CCAAT and GC boxes, and also the stimulatory regulatory sequences ("enhancers"), or inhibitory regulatory sequences ("silencers"), which control, in CIS, the expression of the genes according to the invention; among these regulatory sequences, mention should be made of IRE, MRE and CRE.

The invention also relates to the methods for identifying mutations carried by the human SPG4 gene, in particular mutations responsible for autosomal dominant hereditary spastic paraplegia, characterized in that they use a nucleic acid sequence according to the invention.

These methods for identifying these mutations will, in particular, comprise the following steps: (i) isolation of the DNA from the biological sample to be analyzed, or production of a cDNA from the mRNA of the biological sample; (ii) specific amplification of the target DNA likely to have a mutation, using primers according to the invention; (iii) analysis of the amplification products, in particular the size and/or the sequence of the amplification products, with respect to a reference sequence.

The expression "methods for identifying a mutation according to the invention" is also intended to refer to a method which makes it possible to obtain the nucleic acid on which said mutation has been identified.

The promoter and/or regulatory sequences of the SPG4 gene according to the invention having mutations which may modify the expression of the corresponding protein also form part of the invention.

The nucleic acids characterized in that they can be obtained using one of the preceding methods according to the invention, or the nucleic acids capable of hybridizing, under high stringency conditions (homology of at least 80% between one of the two sequences and the sequence complementary to the other), with said nucleic acids, form part of the invention, especially the variant or homologous nucleic acids, in particular the nucleic acid sequences of allelic variants of the SPG4 gene of sequence SEQ ID No. 1 or of its cDNA of sequence SEQ ID No. 2, and also the genomic sequences of the homologous genes of other mammals such as mice.

In the present description, the term "Spg4" will be intended to refer to the mouse gene homologous to the human SPG4 gene.

The use of a nucleic acid sequence according to the invention as a probe or primer for screening a genomic library or a cDNA of course forms part of the subject of the present invention.

In another aspect, the invention comprises a purified or isolated polypeptide encoded by a nucleic acid according to the invention, preferably with the exception of the 584 amino acid peptide, the sequence of which is identified in the GenBank database under the accession number AB029006.

In the present description, the term "polypeptide" will be used to refer equally to a protein or a peptide.

Preferably, the present invention relates to a polypeptide according to the invention, characterized in that it comprises an amino acid sequence chosen from the following group:

the sequence SEQ ID No. 3, corresponding to human spastin encoded by the sequence SEQ ID No. 2 of the cDNA of the human SPG4 gene;

the sequence SEQ ID No. 73, corresponding to a fragment of murine spastin encoded by the sequence SEQ ID No. 72 of the incomplete cDNA of the mouse Spg4 gene, the sequence SEQ ID No. 73 is represented in FIG. 4A, "SPAST_MOUSE" line;

the sequence SEQ ID No. 107, corresponding to murine spastin encoded by the sequence SEQ ID No. 106 of the complete cDNA of the mouse Spg4 gene;

the sequences of polypeptides which are homologs and variants of the polypeptide of sequence SEQ ID No. 3, SEQ ID No. 73 or SEQ ID No. 107; and the sequences of the fragments thereof of at least 8, 10, 15, 30 or 50 consecutive amino acids.

Also preferably, a subject of the invention is a polypeptide according to the invention, characterized in that it comprises an amino acid sequence chosen from the group comprising:

a) the sequence SEQ ID No. 3, the sequence SEQ ID No. 73, the sequence SEQ ID No. 107 or the sequence of at least 10 consecutive amino acids of one of these sequences; and b) the sequences which are homologs or variants of the sequences SEQ ID No. 3, SEQ ID No. 73 or SEQ ID No. 107.

Also preferably, a subject of the invention is a polypeptide according to the invention, characterized in that it comprises the sequence of at least 8, preferably of at least 10, 15, 20 or 30, consecutive amino acids of the sequence of the aa 197–228, ends inclusive, fragment of the sequence SEQ ID No. 3.

Also preferably, a subject of the invention is a polypeptide according to the invention, characterized in that it comprises an amino acid sequence chosen from the following group:

the sequence SEQ ID No. 3, the sequence SEQ ID No. 73 and the sequence SEQ ID No. 107, which sequences carrying at least one of the mutations corresponding to a natural polymorphism in humans, in particular those the nature and location of which are identified in Table 5 hereinafter, or those which may be identified using the methods for identifying mutations of the SPG4 gene, according to the present invention; and the sequences of the fragments thereof of at least 8, 10, 15, 30 or 50 consecutive amino acids.

It should be understood that the invention does not relate to polypeptides in natural form, i.e. they are not taken in their environment. Specifically, the invention relates to the peptides which are obtained by purification from natural sources, or obtained by genetic recombination or by chemical synthesis, and which can therefore include unnatural amino acids. The production of a recombinant polypeptide, which can be carried out using one of the nucleotide sequences according to the invention, is particularly advantageous since it makes it possible to obtain an increased degree of purity of the desired polypeptide.

The term "homologous polypeptide" will be intended to refer to the polypeptides which have certain modifications with respect to the reference polypeptide, such as in particular one or more deletions or truncations, an extension, a chimeric fusion and/or one or more substitutions, and the amino acid sequence of which shows at least 80%, preferably 90% or 95%, identity after alignment, with the reference amino acid sequence.

The term "variant polypeptide" (or protein variant) will be intended to refer to the set of polypeptides encoded by the variant nucleic acid sequences as defined above.

In particular, the variant polypeptides will comprise any polypeptide which is encoded by the mutated genomic sequence of the SPG4 gene of sequence SEQ ID No. 1, and the amino acid sequence of which has at least one mutation corresponding in particular to a truncation, deletion, substitution and/or addition of amino acid residues with respect to the sequence SEQ ID No. 3. In the present case, the variant polypeptides having at least one mutation will be linked to the pathologies of AD-HSP type.

The term "variant polypeptide" will also be intended to refer to any polypeptide resulting from mutation of a splice site in the genomic nucleic acid sequence SEQ ID No. 1.

The invention also comprises the cloning and/or expression vectors containing a nucleic acid sequence according to the invention.

The vectors according to the invention, characterized in that they include the elements which allow the expression and/or the secretion of said sequences in a host cell, or a cellular addressing sequence, also form part of the invention.

The vectors characterized in that they include a promoter and/or regulator sequence according to the invention also form part of the invention.

Said vectors will preferably include a promoter, translation initiation and termination signals, and also suitable regions for regulating the transcription. They should be able to be maintained stably in the cell and can, optionally, have particular signals which specify secretion of the translated protein.

These various control signals are chosen as a function of the host cell used. To this effect, the nucleic acid sequences according to the invention can be inserted into vectors which replicate autonomously in the host chosen, or vectors which integrate in the host chosen.

Among the systems which replicate autonomously, use will preferably be made, as a function of the host cell, of the systems of plasmid or viral type, the viral vectors possibly in particular being adenoviruses (Perricaudet et al., 1992), retroviruses, lentiviruses, poxviruses or herpesviruses (Epstein et al., 1992). Those skilled in the art know the technology which can be used for each of these systems.

When integration of the sequence into the chromosomes of the host cell is desired, use may be made, for example, of the systems of plasmid or viral type; such viruses will, for example, be retroviruses (Temin, 1986), or AAVs (Carter, 1993).

Among the nonviral vectors, preference is given to naked polynucleotides such as naked DNA or naked RNA according to the technique developed by the company VICAL, yeast artificial chromosomes (YAC) for expression in yeast, mouse artificial chromosomes (MAC) for expression in murine cells and, preferably, human artificial chromosomes (HAC) for expression in human cells.

Such vectors will be prepared according to the methods commonly used by those skilled in the art, and the clones resulting therefrom can be introduced into a suitable host using standard methods, such as for example lipofection, electroporation or heat shock.

The invention also comprises the host cells, in particular the eukaryotic and prokaryotic cells, transformed with the vectors according to the invention, and also the transgenic animals, except humans, comprising one of said transformed cells according to the invention.

Among the cells which can be used for these purposes, mention may of course be made of bacterial cells (Olins and Lee, 1993), but also yeast cells (Buckholz, 1993), as well as animal cells, in particular cultures of mammalian cells (Edwards and Aruffo, 1993), and especially Chinese hamster ovary (CHO) cells, but also insect cells in which it is possible to use processes implementing baculoviruses, for example (Luckow, 1993). A preferred cellular host for expressing the proteins of the invention consists of CHO cells.

Among the mammals according to the invention, preference will be given to animals such as mice, rats or rabbits, expressing a polypeptide according to the invention.

Among the mammals according to the invention, preference will also be given to those comprising a transformed cell characterized in that the sequence of at least one of the two alleles of the SPG4 gene contains at least one of the mutations corresponding to a natural polymorphism in humans, in particular those the nature and location of which are identified in Table 5 hereinafter, or those which may be identified using the methods for identifying a mutation of the SPG4 gene, according to the present invention.

Among the mammals according to the invention, preference will also be given to animals such as mice, rats or rabbits, characterized in that the gene encoding spastin according to the invention is not functional or is knocked out.

Among the animal models more particularly advantageous herein, there are, in particular:
  the transgenic animals having, at least in one of their two allelic sequences of the SPG4 gene, at least one of the mutations the position and nature of which are identified in Table 5 or identified using a method according to the present invention These transgenic animals are obtained, for example, by homologous recombination on embryonic stem cells, transfer of these stem cells to embryos, selection of the chimeras affected in the reproductive lines, and growth of said chimeras;
  the transgenic animals (preferably mice) overexpressing the SPG4 gene into which one of said mutations according to the invention may be introduced. The mice are obtained, for example, by transfection of a copy of this gene under the control of a strong promoter which is ubiquitous in nature or selective for a tissue type, or after viral transcription;
  the transgenic animals (preferably mice) made deficient for the SPG4 gene according to the invention by inactivation using the LOXP/CRE recombinase system (Rohlmann et al., 1996) or any other system for inactivating the expression of this gene.

The cells and mammals according to the invention can be used in a method for producing a polypeptide according to the invention, as described below, and can also be used as a model for analysis and for DNA (genomic or cDNA) library screening.

The transformed cells or mammals as described above can thus be used as models in order to study the interactions between the polypeptides according to the invention, and chemical or protein compounds, which are involved directly or indirectly in the activities of the polypeptides according to the invention, this being in order to study the various mechanisms and interactions which come into play.

They can especially be used for selecting products which interact with the polypeptides according to the invention, in particular human spastin of sequence SEQ ID No. 3 or the variants thereof according to the invention, as a cofactor or as an inhibitor, in particular a competitive inhibitor, or which have agonist or antagonist activity for the activity of the polypeptides according to the invention. Preferably, said transformed cells or transgenic animals will be used as a model which, in particular, enables the selection of products which make it possible to combat the pathology linked to the SPG4 gene mentioned above.

The invention also relates to the use of a cell, of a mammal or of a polypeptide according to the invention for screening a chemical or biochemical compound which can interact directly or indirectly with the polypeptides according to the invention, and/or which is capable of modulating the expression or the activity of these polypeptides.

The invention also relates to the use of a nucleic acid sequence according to the invention for synthesizing recombinant polypeptides.

The method for producing a polypeptide of the invention in recombinant form is, itself, included in the present invention, and is characterized in that the transformed cells, in particular the cells or mammals of the present invention, are cultured under conditions which allow the expression of a recombinant polypeptide encoded by a nucleic acid sequence according to the invention, and in that said recombinant polypeptide is recovered.

The recombinant polypeptides, characterized in that they can be obtained using said production method, also form part of the invention.

The recombinant polypeptides obtained as indicated above can be in both glycosylated and nonglycosylated form and may or may not have the natural tertiary structure.

These polypeptides can be produced based on the nucleic acid sequences defined above, according to the techniques for producing recombinant polypeptides known to those skilled in the art. In this case, the nucleic acid sequence used is placed under the control of signals which allow its expression in a cellular host.

An effective system for producing a recombinant polypeptide requires a vector and a host cell according to the invention.

These cells can be obtained by introducing into host cells a nucleotide sequences inserted into a vector as defined above, and then culturing said cells under conditions which allow the replication and/or expression of the transfected nucleotide sequence.

The processes for purifying a recombinant polypeptide which are used are known to those skilled in the art. The recombinant polypeptide can be purified from cell lyzates and extracts and/or from the culture medium supernatant, with methods used individually or in combination, such as fractionation, chromatography methods, immunoaffinity techniques using specific monoclonal or polyclonal antibodies, etc.

The polypeptides according to the present invention can be obtained by chemical synthesis, this using one of the many known peptide syntheses, for example the techniques which implement solid phases or techniques which use partial solid phases, by condensation of fragments or by a conventional synthesis in solution.

The solid-phase synthesis technique is well known to those skilled in the art. See in particular Stewart et al. (1984) and Bodansky (1984).

The polypeptides which are obtained by chemical synthesis and which can include corresponding unnatural amino acids are also included in the invention.

The mono- or polyclonal antibodies or their fragments, chimeric antibodies or immunoconjugates, characterized in that they are capable of specifically recognizing a polypeptide according to the invention, form part of the invention.

Specific polyclonal antibodies can be obtained from a serum of an animal immunized against the polypeptides according to the invention, in particular produced by genetic recombination or by peptide synthesis, according to conventional procedures.

The advantage of antibodies which specifically recognize certain polypeptides, variants or immunogenic fragments thereof, according to the invention, will in particular be noted.

The specific monoclonal antibodies can be obtained according to the conventional hybridoma culture method described by Köhler and Milstein, 1975.

The antibodies according to the invention are, for example, chimeric antibodies, humanized antibodies, or Fab or F(ab')$_2$ fragments. They can also be in the form of labeled antibodies or immunoconjugates in order to obtain a detectable and/or quantifiable signal.

The invention also relates to methods for detecting and/or purifying a polypeptide according to the invention, characterized in that they use an antibody according to the invention.

The invention also comprises purified polypeptides, characterized in that they are obtained using a method according to the invention.

Moreover, besides their use for purifying the polypeptides, the antibodies of the invention, in particular the monoclonal antibodies, can also be used for detecting these polypeptides in a biological sample.

They thus constitute a means of immunocytochemically or immuno-histochemically analyzing the expression of the polypeptides according to the invention, in particular the polypeptide of sequence SEQ ID No. 3 or a variant thereof, on specific tissue sections, for example by immunofluorescence or gold labeling, or with an enzymatic immunoconjugates.

They may make it possible, in particular, to demonstrate abnormal expression of these polypeptides in the biological samples or tissues, which makes them useful for monitoring the progression of the disease and the molecular diagnosis.

More generally, the antibodies of the invention can be advantageously used in any situation in which the expression of a normal or mutated polypeptide according to the invention must be observed.

The methods for determining allelic variability, a mutation, a deletion, a loss of heterozygosity or any genetic abnormality of the SPG4 gene, according to the invention, characterized in that they use a nucleic acid sequence or an antibody according to the invention, also form part of the invention.

The present invention thus comprises a method for genotypic diagnosis of the pathology associated with the SPG4 gene, characterized in that a nucleic acid sequence according to the invention is used.

Preferably, the invention relates to a method for genotypic diagnosis of the disease associated with the presence of at least one mutation on a sequence of the SPG4 gene, using a biological sample from a patient, characterized in that it includes the following steps:

a) where appropriate, isolation of the genomic DNA from the biological sample to be analyzed, or production of cDNA from the RNA of the biological sample;
b) specific amplification of said DNA sequence of the SPG4 gene likely to contain a mutation, using primers according to the invention;
c) analysis of the amplification products obtained and comparison of their sequence with the corresponding normal sequence of the SPG4 gene.

The invention also comprises a method for diagnosing the disease associated with abnormal expression of a polypeptide encoded by the SPG4 gene, in particular the polypeptide of sequence SEQ ID No. 3, characterized in that one or more antibodies according to the invention is (are) brought into contact with the biological material to be tested, under conditions which allow the possible formation of specific immunological complexes between said polypeptide and said antibody or antibodies, and in that the immunological complexes possibly formed are detected and/or quantified.

These methods are, for example, directed toward the methods for diagnosis, in particular antenatal diagnosis, of AD-HSP associated with the presence of a mutation in the SPG4 gene, according to the invention, by determining, using a biological sample from the patient, the presence of mutations in at least one of the sequences described above. The nucleic acid sequences analyzed may equally be genomic DNA, cDNA or mRNA.

Nucleic acids or antibodies based on the present invention may also be used to enable positive diagnosis in a patient or presymptomatic diagnosis in an individual at risk, in particular an individual with a family history of the disease.

There are, of course, a great number of methods which make it possible to demonstrate a mutation in a gene with respect to the wild-type gene. They can essentially be divided into two main categories. The first type of method is that in which the presence of a mutation is detected by comparing the mutated sequence with the corresponding wild-type sequence, and the second type is that in which the presence of the mutation is detected indirectly, for example through evidence of mismatches due to the presence of the mutation.

These methods can use the probes and primers of the present invention which have been described. They are generally purified nucleic acid hybridization sequences comprising at least 15 nucleotides, preferably 20, 25 or 30 nucleotides, characterized in that they can hybridize specifically with a nucleic acid sequence according to the invention.

Preferably, the specific hybridization conditions are such as those defined above or in the examples. The length of these nucleic acid hybridization sequences can range from 15, 20 or 30 to 200 nucleotides, particularly from 20 to 50 nucleotides.

Among the methods for determining allelic variability, a mutation, a deletion, a loss of heterozygocity or a genetic abnormality, preference is given to the methods comprising at least one so-called PCR (polymerase chain reaction) or PCR-like amplification step for the target sequence according to the invention likely to have an abnormality, using a pair of primers having nucleotide sequences according to the invention. The amplified products may be treated with a suitable restriction enzyme before carrying out the detection and assaying of the product targeted.

The mutations of the SPG4 gene according to the invention may be responsible for various modifications of the translation product thereof, these modifications possibly being used for a diagnostic approach. Specifically, the antigenicity modifications linked to these mutations may allow the development of specific antibodies. The mutated gene product can be distinguished using these methods. All these modifications can be employed in a diagnostic approach, using several well-known methods based on the use of mono- or polyclonal antibodies which recognize the normal polypeptide or mutated variants, such as for example by RIA or by ELISA.

Thus, a subject of the invention is also a kit or pack for diagnosis, in particular for diagnosing AD-HSP associated with the presence of a mutation in the SPG4 gene, according to the invention, characterized in that it comprises at least one compound chosen from the following group of compounds:

a) a nucleic acid, in particular as a primer or probe, according to the present invention; and
b) an antibody according to the invention.

In another aspect, the invention comprises a method for selecting a chemical or biochemical compound capable of preventing and/or treating AD-HSP associated with the SPG4 gene, characterized in that a nucleic acid sequence according to the invention, a polypeptide according to the invention, a vector according to the invention, a cell according to the invention, a mammal according to the invention or an antibody according to the invention is used.

The methods for selecting chemical or biochemical compounds capable of interacting directly or indirectly with polypeptides according to the invention or with the nucleic acids according to the invention, and/or making it possible to modulate the expression or the activity of these polypeptides, characterized in that they comprise bringing a polypeptide according to the invention, a transformed cell according to the invention or a mammal according to the invention into contact with a candidate compound, and detecting a modification of the activity of said polypeptide, are also included in the invention.

For example, but without being limited thereto, mention may be made of a method for identifying molecules capable of interacting with a polypeptide according to the invention, using a bacterial or yeast two hybrid system such as the Matchmaker Two Hybrid System 2, according to the instructions of the manual which is supplied with the Matchmaker Two Hybrid System 2 (Catalog No. K1604-1, Clontech).

The nucleic acids encoding proteins which interact with the promoter and/or regulatory sequences of the SPG4 gene, according to the invention, can be screened and/or selected using a one hybrid system such as that described in the manual which is supplied with the Matchmaker One Hybrid System kit from Clontech (Catalog No. K1603-).

In other aspect, the invention comprises the use of a nucleic acid or of a polypeptide according to the invention, of a vector according to the invention, of a cell according to the invention or of a mammal according to the invention, for studying the expression or the activity of the SPG4 gene.

Other characteristics and advantages of the invention appear in the remainder of the description with the examples and figures, the legends of which are given hereinafter.

BRIEF DESCRIPTION OF THE DRAWINGS

FIGS. 1A, 1B and 1C: Physical map of the SPG4 range and genomic organization of SPG4.

FIG. 1A: The 1.5 Mb candidate region is delimited by the D2S352 and D2S2347 genetic markers indicated in bold characters. The position of the polymorphic markers and other STSs is indicated in standard characters, whereas the position of the ESTs is indicated in italics. The BAC clones constituting the presequencing map are represented by rectangles, with the name shown above and the precise size of the clone, if it could be determined, shown below. The name of the BACs A, B, C, etc. is followed by brackets containing the name of the clone preceded by a "b" if the clone is derived from the BACs library CITB_978_SKB, or by a "B" if it originates from the library RPCI-11.

FIG. 1B: Schematic representation of the SPG4 gene which overlaps BACs D (b336P14) and G (B563N4). The exons are shown as black rectangles with their name above.

FIG. 1C: The five mutations identified in seven SPG4 locus-linked AD-HSP families are positioned in exons 7, 11 and 13 and in the splice acceptor site of intron 15.

FIG. 2: Nucleic acid (SEQ ID NO:2) and protein sequence (SEQ ID NO:3) of the SPG4 cDNA of spastin.

The 17 vertical bars with a number located below represent the junctions between the various exons. The ATG initiator codon is located at nt position 126–128 and the STOP codon for termination is located at nt position 1974–1976. Five of the mutations identified to date, including the loss of exon 16, are indicated in italics (nt 1210, nt 1468, nt 1520, nt 1620 and for the loss of exon 16: nt 1813–1853). The polyadenylation site is in italics and underlined. The putative nuclear localization signal (NLS), RGKKK, and also the three conserved domains predicted by the analysis in the ProDom database are located at aa positions 7–11 (NLS), 342–409 (domain 92), 411–509 (domain 179) and 512–599 (domain 6226), respectively. The four motifs predicted by the sequence comparison in the Prosite database are: two "leucine zipper" motifs at aa positions 50–78 and 508–529, the ATP binding site (or Walker A motif) at aa positions 382–389 and the "helix-loop-helix" dimerization domain at aa positions 478–486. The Walker A and B motifs, "GPPGNGKT" and "IIFIDE", and also the AAA minimum consensus [lacuna] are underlined.

Figure 3:
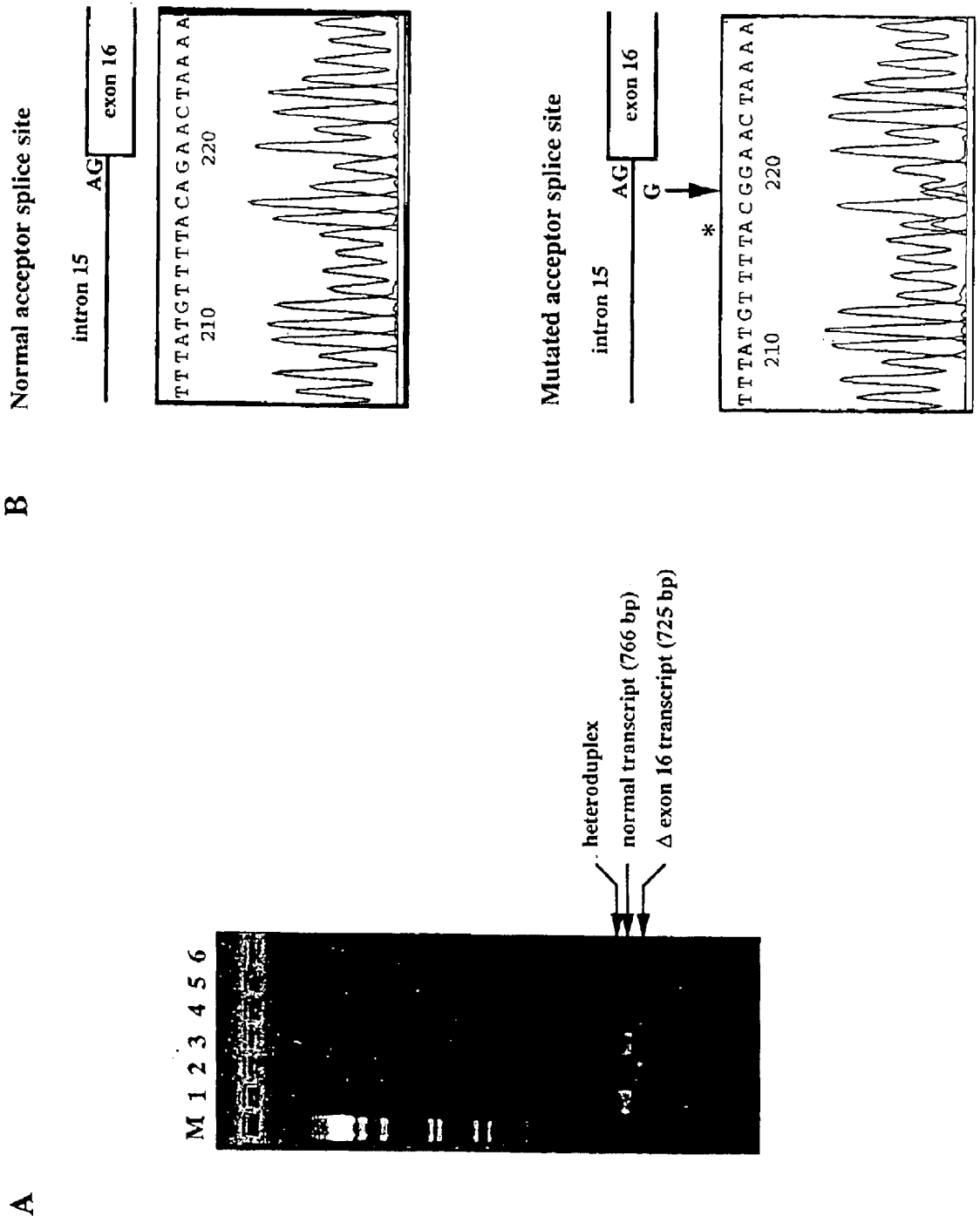

FIGS. 3A and 3B: Characterization of a splice site mutation in the affected individuals of three SPG4 locus-linked AD-HPS families.

FIG. 3A: PCR amplification of fragment IV of the SPG4 cDNA using lymphoblast cDNA: well M, size marker VII (Boehringer); well 1, unaffected member of family 2992; well 2, patient of family 2992; well 3, unaffected member of family 5330; well 4, patient of family 5330; well 5, patient of family 5226; well 6, negative control (human genomic DNA).

FIG. 3B: Sequence graph for the mutation of the splice acceptor site of intron 15.

Genomic sequence of the control individual above and of a patient of family 2992 below. The asterisk at nt position 1813-4 indicates an A→C polymorphism which affects a nonconserved nucleotide of the splice acceptor site of intron 15 in the patient.

Figure 4A:
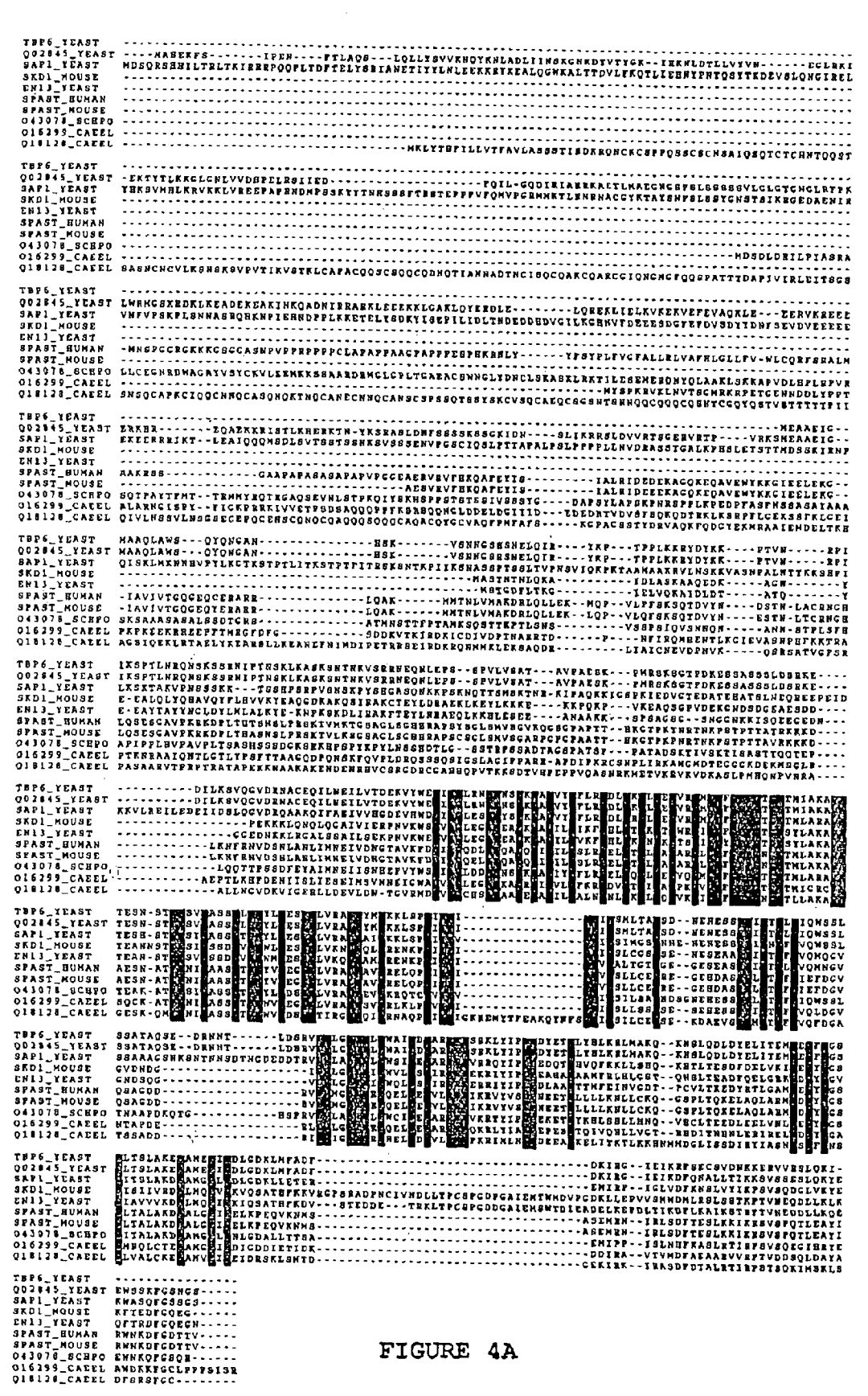

FIGS. 4A and 4B: Spastin homologies.

The identical residues are highlighted by shaded areas.

FIG. 4A: Multiple alignment created by CLUSTAL W of eight proteins derived from various organisms and having strong sequence homology with human spastin and murine spastin (SEQ ID No. 73).

FIG. 4B: Alignement by CLUSTAL W of the yeast metalloproteases AFG3, RCA1 and YME1, and of human plaraplegin and spastin.

Figure 5:
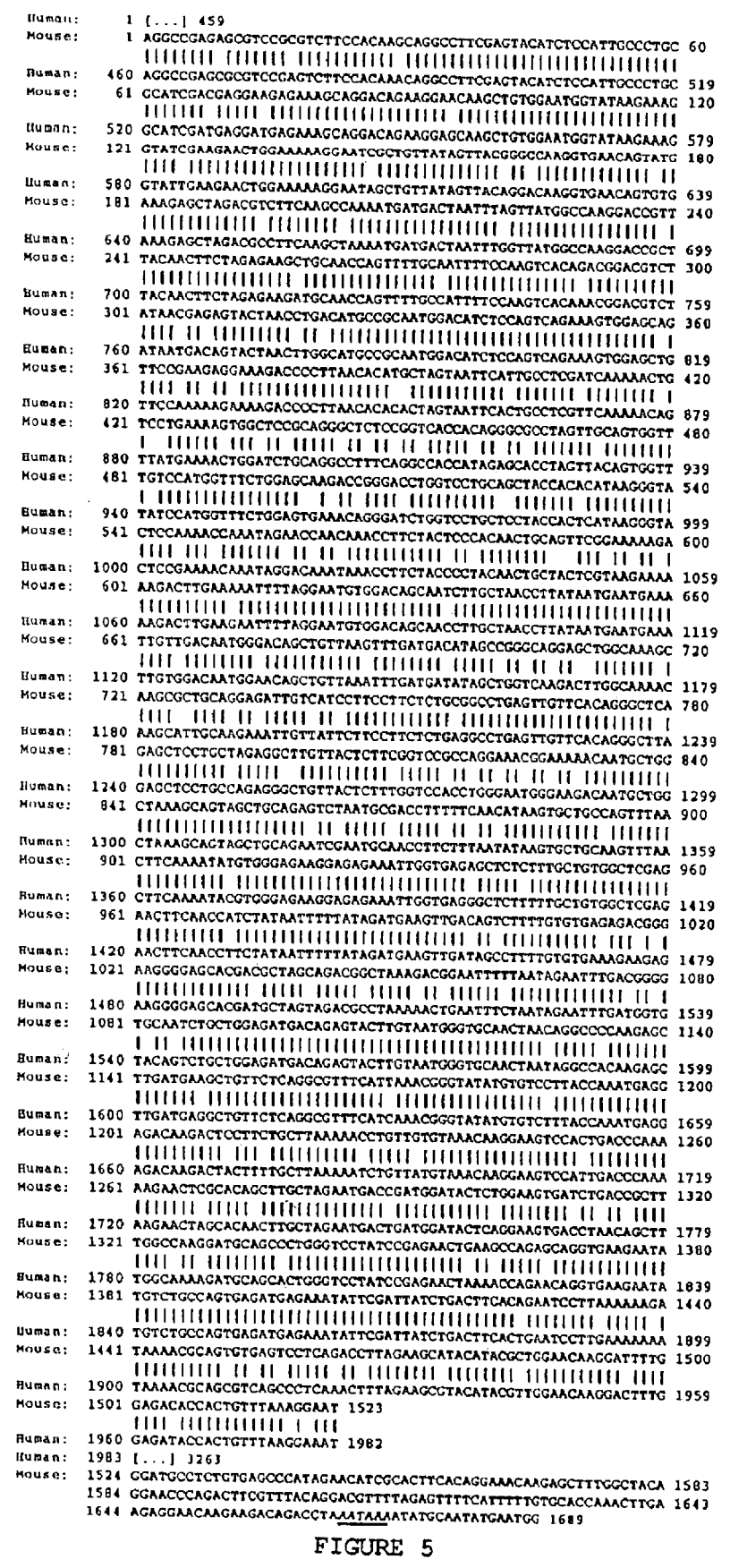

FIG. 5: Alignment by BLASTN of the nucleic acid sequences of the SPG4 cDNA and of its mouse ortholog Spg4 (SEQ ID No. 72). The polyadenylation site of the murine cDNA is underlined and in italics. The STOP codon is located at nt position 1515–1517 in the murine cDNA and at nt position 1974–1976 in the human cDNA.

Figure 6:
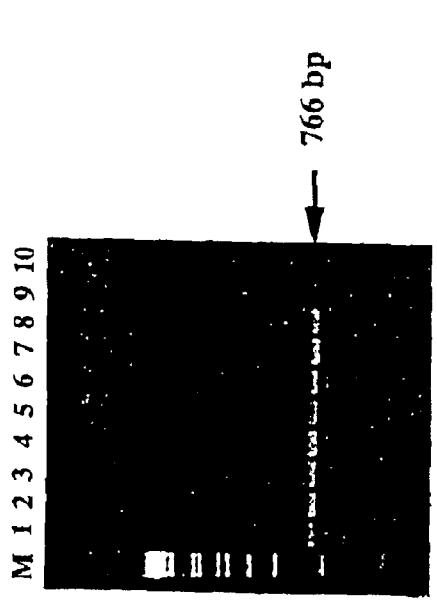
Figure 6:
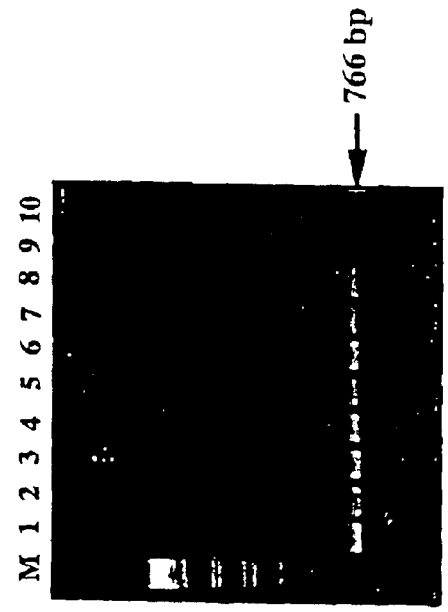
Figure 6:
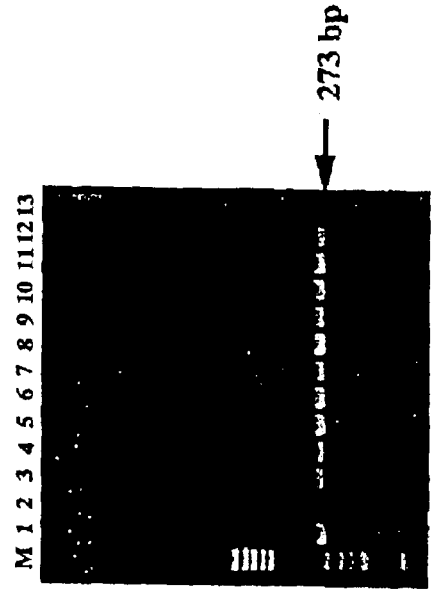

FIGS. 6A, 6B and 6C: PCR analysis of the expression of SPG4 and of its murine ortholog Spg4.

FIG. 6A: Collection of cDNA originating from multiple mouse tissues.

Well M, size marker V (Boehringer); well 1, heart, well 2, brain; well 3, spleen; well 4, lung; well 5, liver; well 6, skeletal muscle; well 7, kidney; well 8, testicle; well 9, E7 7-day embryo; well 10, E11 11-day embryo; well 11, E15 15-day embryo; well 12, E17 17-day embryo; well 13, negative control (mouse genomic DNA).

FIG. 6B: Collection of cDNA originating from multiple human tissues.

Well M, size marker VII (Boehringer); well 1, brain; well 2, heart; well 3, kidney; well 4, liver; well 5, lung; well 6, pancreas; well 7, placenta; well 8, skeletal muscle, well 9, negative control (human genomic DNA); well 10, negative control (no DNA).

FIG. 6C: Collection of cDNA originating from multiple human fetal tissues.

Well M, size marker VII (Boehringer); well 1, brain; well 2, heart; well 3, kidney; well 4, liver; well 5, lung; well 6, skeletal muscle; well 7, spleen; well 8, thymus; well 9, negative control (human genomic DNA); well 10, negative control (no DNA).

DETAILED DESCRIPTION OF THE PREFERRED EMBODIMENTS

EXAMPLES

Example 1

Materials and Methods
1) Subcloning and Sequencing of the Candidate Region

Twelve BACs originating from two human genomic libraries, CITB_978_SKB (sold by Research Genetics) and RPCI-11 (Osoegawa et al., 1998), and covering the SPG4 range, were selected to be sequenced (Hazan et al., Genomics, 60 (3), 309–19, 1999). 40 µg of the DNA of each BAC were partially digested with the CviJI restriction enzyme (CHIMERx) and separated by electrophoresis on 0.4% LMP agarose gel (FMC). DNA fractions, the sizes of which vary in the region of 3, 5 and 10 kb, were eluted with β-agarase (Biolabs) and ligated to a plasmid vector pBAM3, which had been digested with SmaI and dephosphorylated, beforehand, in a ratio of 1× insert per 5× vector. Electrocompetent *E. coli* DH10B bacteria (GIBCO-BRL) were transformed with the various ligations, by electroporation. Approximately 1 000 to 1 500 subclones per BAC (8 to 10 equivalent genomes), consisting of 20% of clones with inserts at 10 kb, 40% of clones with inserts at 5 kb and 40% of clones with inserts at 3 kb, were isolated. The ends of the inserts of these clones were sequenced on a LICOR 4200 automatic sequencer. For each BAC, the sequences were assembled into a backbone consisting of several contigs, using the Phred and Phrap programs. The holes between each contig were sequenced with labeled dideoxynucleotides on an ABI 377 sequencer (PE-Applied Biosystems). The exons contained in these sequence contigs were predicted with the GRAIL II, GENSCAN, FGENEH and Genie computer programs. The sequences were also compared in the EMBL and GenBank nucleic acid and protein databases, with the BLASTN and BLASTX programs. The determination of the promoter sequences was carried out using the TSSG and TSSW computer programs. The results of all these sequence analyses were visualized using the Genotator sequence annotation program.

2) cDNA Cloning

The cDNA of the SPG4 gene was isolated through 5' and 3' RACE-PCR experiments on polyA+ RNAs of fetal brain, adult brain and adult liver, using the Marathon cDNA amplification kit (Clontech) according to the supplier's instructions. A first PCR followed by an internal PCR were carried out with various pairs of primers, the sequences of which are indicated in Table 1 hereinafter:

TABLE 1

Primers used for the RACE-PCRs and the cDNA amplifications

| Primer | Sequence (5'–3') | 5' position pair/ PCR product size | | |
|---|---|---|---|---|
| SPA_5RACE5 | CGGAGCTCCTCTTGGCTGCCATG (SEQ ID No. 4) | nt 405 | | |
| SPA_5RACE6 | AGAAGCGCTGGCAGAGCCACACGAAG (SEQ ID No. 5) | nt 372 | | |
| SPA_5RACE7 | AAGGCGACCAAACGCAGCAGCGCGAAG (SEQ ID No. 6) | nt 331 | | |
| SPA_3RACE1 | AGGAGCAAGCTGTGGAATGGTATAAG (SEQ ID No. 7) | nt 550 | | |
| SPA_3RACE2 | TGGTTATGGCCAAGGACCGCTTACAAC (SEQ ID No. 8) | nt 689 | | |
| SPA_3RACE3 | CAAACGGACGTCTATAATGACAGTAC (SEQ ID No. 9) | nt 747 | | |
| SPA_3RACE4 | TTAGGAATGTGGACAGCAACCTTGC (SEQ ID No. 10) | nt 1075 | | |
| SPA_3RACE5 | CTTCTCTGAGGCCTGAGTTGTTCAC (SEQ ID No. 11) | nt 1207 | | |
| SPA_3RACE6 | TGCTAGAATGACTGATGGATACTCAGG (SEQ ID No. 12) | nt 1736 | | |
| SPA_3RACE7 | AGATGCAGCACTGGGTCCTATCCG (SEQ ID No. 13) | nt 1787 | | |
| SPA_3RACE8 | ATGAACGTCATCGGCTACAGAAACAG (SEQ ID No. 14) | nt 2037 | | |
| SPA_Db | TAGCAGTGGCTGCCGCCGT (SEQ ID No. 15) | nt 45 | b + m | 655 bp |
| SPA_Dm | AAGCGGTCCTTGGCCATAAC (SEQ ID No. 16) | nt 700 | | |
| SPA_Dc | GGCGGCAGTGAGAGCTGTG (SEQ ID No. 17) | nt 106 | c + n | 543 bp |
| SPA_Dn | CTAGCTCTTTCACACTGTTC (SEQ ID No. 18) | nt 649 | | |
| SPA_Ad | AACAGGCCTTCGAGTACATC (SEQ ID No. 19) | nt 487 | d + n | 746 bp |
| SPA_Am | CTGTGAACAACTCAGGCCTC (SEQ ID No. 20) | nt 1233 | | |
| SPA_Ac | ATGAGAAAGCAGGACAGAAG (SEQ ID No. 21) | nt 532 | | |
| SPA_An | TGCCAAGTCTTGACCAGC (SEQ ID No. 22) | nt 1175 | | |
| SPA_Ba | CTACAACTGCTACTCGTAAG (SEQ ID No. 23) | nt 1036 | a + m | 763 bp |
| SPA_Bm | CAGTGCTGCATCTTTTGCC (SEQ ID No. 24) | nt 1799 | | |
| SPA_Bb | TAGGAATGTGGACAGCAACC (SEQ ID No. 25) | nt 1076 | | |
| SPA_Bn | AAAGCTGTTAGGTCACTTCC (SEQ ID No. 26) | nt 1780 | | |
| SPA_Ca | TGGAGATGACAGAGTACTTG (SEQ ID No. 27) | nt 1550 | a + m | 766 bp |

TABLE 1-continued

Primers used for the RACE-PCRs and the cDNA amplifications

| | | |
|---|---|---|
| SPA_Cm | CTGGAATACTTTCATCTGC (SEQ ID No. 28) | nt 2316 |
| SPA_Cb | ATGAGGCTGTTCTCAGGCG (SEQ ID No. 29) | nt 1603 |

The RACE-PCR products were cloned with the TA-cloning kit (Invitrogen) and the corresponding clones were sequenced on an ABI 377 (PE-Applied Biosystems). The sequence of the SPG4 transcript was varified by sequencing PCR products amplified from a cDNA population originating from the lymphoblasts of 6 healthy individuals.

3) Detection of Mutations

The total RNAs were extracted from lymphoblast lines of one affected individual per family studied and of 6 control individuals, using the RNA PLUSR kit (bioprobe System). The cDNA synthesis was carried out on 500 ng to 1 µg of RNA, with 100 pmol of random hexameric primers (Pharmacia) and 200 units of Superscript II reverse transcriptase (Gibco BRL), under standard conditions. Four PCR amplifications, generating overlapping fragments which cover all of the SPG4 open reading frame, were carried out on the cDNAs of the patients and controls. Fragment I was amplified with the SPA_Db/SPA_Dm primers, and then by internal PCR with the SPA_Dc/SPA_Dn primers. Fragments II, III, and IV were amplified with the SPA_Ad/SPA_Am, SPA_Ba/SPA_Bm and SPA_Ca/SPA_Cm primers (cf. the sequences of these primers in Table 1), respectively. Each amplification was carried out in a total volume of 50 µl containing 4 µl of cDNA (~1/7th of the prep.), 20 pmol of each primer, 200 µM of dNTPs, 50 mM of KCl, 10 mM of Tris, pH 9, 1.5 mM $MgCl_2$, 0.1% of triton X-100, 0.01% of gelatin and 2.5 units of Taq polymerase (Cetus-PE). The PCR reactions were carried out according to the "hot start" process: the Taq polymerase is added at 92° C., after a first denaturation step of 5 min at 94° C. The samples are subsequently subjected to 35 cycles of denaturation (94° C. for 40 sec), of hybridization (55° C. for 50 sec, with the exception of fragment I; 58° C. for 50 sec) and of elongation (72° C. for 1 min), followed by a final elongation step (5 min at 72° C.). The PCR products are sequenced on an ABI 377 automatic sequencer (PE-Applied Biosystems), with the SPA_Dc/SPA_Dn, SPA_Ac/SPA_An, SPA_Bb/SPA_Bn and SPA_Cb/SPA_Cm primers for fragments I, II, III and IV, respectively.

The mutations were also sought or confirmed by sequencing the 17 predicted exons of the SPG4 gene in the patients and controls. Each exon was amplified with the corresponding "a+m" pair of primers (cf. Table 2 hereinafter), with the exception of exon 1 (gSPAex1c/gSPAex1m), and exons 10, 11 and 12 which were co-amplified with the gSPAex10a/gSPAex12m and gSPAex11a/gSPAex12m pairs of primers.

TABLE 2

PCR primers for amplifying and sequencing the exons

| Exon | Product size | PCR program | Primer | Sequence (5'–3') (SEQ ID Nos.; 30 to 71) |
|---|---|---|---|---|
| 1 | 1048 bp | 0 | gSPAex1c | GTGAGCCGAACTGCACATTG |
| | | | gSPAex1m | CAAAGTCGACAGCTACAGTGC |
| | | | gSPAex1d | GGAACTGTAGTTGAGTGGGA |
| | | | gSPAex1n | AGATGAGGCTCCGACCTAC |
| 2 | 624 bp | 3 | gSPAex2a | AATGCCACACTTGTAATCTC |
| | | | gSPAex2m | TGTGAATATATCATAATTTGGG |
| | | | gSPAex2b | TACAGCAGTTCTCATGATG |
| 3 | 812 bp | 1 | gSPAex3a | GACCAAATTGGTGCATGCATG |
| | | | gSPAex3m | ACATTTCCAATACATCCCAC |
| 4 | 379 bp | 3 | gSPAex4a | ATTTGTCATTTCACATGCAC |
| | | | gSPAex4m | TTAGAATGACTATACCTGAC |
| | | | gSPAex4n | TCAGGTTAAGTAAGACTC |
| 5 | 830 bp | 4 | gSPAex5a | TTCCTATCTACCTAGTGAC |
| | | | gSPAex5m | TTTTATAGCAAGTTGCCCTG |
| | | | gSPAex5b | CCTATGAAGATCCTGGTAC |
| 6 | 484 bp | 3 | gSPAex6a | TGTCATGATTCTAACAAGGG |
| | | | gSPAex6m | TCTATTTCACTCCTGACATG |
| 7 | 420 bp | 2 | gSPAex7a | GTCATAGGGCTTAGGCTTC |
| | | | gSPAex7m | ATCATACTACCCACTTTTCC |
| 8 | 647 bp | 3 | gSPAex8a | TGTTTGGGAAGATGCTACTG |
| | | | gSPAex8m | CTACTGAAGATAACGTACATG |
| 9 | 1268 bp | 1 | gSPAex9a | CATTGATTGCCATGTATTGG |
| | | | gSPAex9m | AGAAGGCCAGAAATACTCAG |
| | | | gSPAex9b | GTACTTAAATCGGTAAATATGG |
| 10 11 12 | 1061 bp 551 bp | 4 3 | gSPAex10a gSPAex10b gSPAex11a gSPAex12m | CTCAAGTCTTAGGAATGCAG GCACTTAACCAGGCTGTATG CTCAGATGACTCACATAGC CTTTACTAGACTAATTCTCCTG |
| 13 | 1361 bp | 4 | gSPAex13a | CAGATTCAAGAAGACAGATC |
| | | | gSPAex13m | GCAATAATTCACCACACTTG |
| | | | gSPAex13n | GGTAGTTCTTGTTTCTGCTC |

TABLE 2-continued

PCR primers for amplifying and sequencing the exons

| Exon | Product size | PCR program | Primer | Sequence (5'–3') (SEQ ID Nos.; 30 to 71) |
|---|---|---|---|---|
| 14 | 985 bp | 4 | gSPAex14a | CAAGTGTGGTGAATTATTGC |
|  |  |  | gSPAex14m | GAGCTGAAAAGTATTCAGC |
|  |  |  | gSPAex14n | TGCAAAGGACATAGCCAGTG |
| 15 | 1076 bp | 1 | gSPAex15a | AGCCTCTGGAGATAGTATGC |
|  |  |  | gSPAex15m | CTAGAACAGGGGTCACAGTC |
|  |  |  | gSPAex15n | TTGGACTTCTTAAACTTC |
| 16 | 1404 bp | 4 | gSPAex16a | GCAGTATGCAAGAAATTGAAC |
|  |  |  | gSPAex16m | GGCCTGTAATTTTCTTCTG |
|  |  |  | gSPAex16b | GTACTGAATAGATACATGTAG |
| 17 | 445 bp | 3 | gSPAex17a | GTGTAGCAGATCAACATAG |
|  |  |  | gSPAex17m | CATCTTCAAGTTTGGTGCAC |

Other than for exon 1, which is amplified using the Advantage GC genomic PCR kit (Clontech) according to the supplier's instructions, four slightly different PCR programs (1, 2, 3 and 4) were used to amplify the SPG4 exons (see Table 2). The amplifications were all carried out in a volume of 50 μl containing 100 ng of genomic DNA, 50 pmol of each primer, 250 μM pf dNTPs, 1× Takara buffer and 1 unit of Takara La Taq Taq polymerase (Shuzo Co.). The PCR reactions were carried out according to the "hot start" process: the Taq polymerase is added at 94° C., after a first denaturation step of 5 min at 96° C. The samples are subsequently subjected to 30 cycles of denaturation (94° C. for 40 sec), of hybridization (prog. 1: 60° C. for 50 sec; prog. 2: 58° C. for 50 sec, prog. 3 and 4: 55° C. for 50 sec) and of elongation (prog. 1 and 4: 72° C. for 1 min, prog. 2 and 3: 72° C. for 40 sec), followed by a final elongation step (10 min at 72° C.). The sequencing of these PCR products was carried out on an ABI 377 sequencer (PE-Applied Biosystems), using either the PCR primers or the internal primers termed "b" and "n" (see Table 2).

4) Characterization of SPG4

The cDNA clones 977312 (EST AA560327) and 568234 (EST AA107866) derived from the mouse blastocyst and E8 embryo cDNA libraries, which both correspond to the murine ortholog of SPG4, were isolated using the IMAGE consortium and sequenced in the laboratory on an ABI 377 sequencer (PE-Applied Biosystems). In order to analyze the expression profile of SPG4 and of its murine ortholog Spg4, the collections of cDNA from various fetal and adult human tissues, and also from mouse tissues (MTC panels, Clontech), were tested by PCR according to the supplier's protocol, with the SPA__Ca/SPA__Cm pair of primers for the human cDNAs and the SPA__Ca/spam (spam: 5'-ACCGAAGTCAAGAGCCTATC-3') pair for the mouse cDNAs. The PCR conditions are those used for amplifying SPG4 from lymphoblast line cDNA (cf. § Detection of mutations), except that these samples were subjected to 32 cycles for the cDNAs derived from adult human tissues and from mouse tissues, and to 28 cycles for the cDNAs derived from fetal tissues. The amplification products migrated by electrophoresis on 2% agarose gels.

5) Histological Analysis of a Muscle Biopsy from a Patient

The histological and histo-enzymatic analyses were carried out on a muscle biopsy from a patient derived from an SPG4 locus-linked family according to the standard techniques described in Casari et al., 1998.

6) Accession Numbers in the Public Databases

The SPG4 (or SPAST) cDNA and the deduced protein sequence, GenBank/EMBL AJ246001; the incomplete Spg4 cDNA clone, GenBank/EMBL AJ246002; the SPG4 (or SPAST) gene, GenBank/EMBL AJ246003.

Example 2

Analysis of the Sequence of the SPG4 Range

The analysis of the recombination events made it possible to reduce the SPG4 candidate region to a genetic range of 0 cM between the D2S352 and D2S2347 markers (19, 20). A presequencing map of the SPG4 range composed of 37 BACs was constructed (Hazan et al., in press in Genomics); the candidate region covers a physical distance of approximately of 1.5 Mb. Twelve overlapping BACs, stretching over the SPG4 region, with the exception of a single 4 kb hole between clones A and E, were selected to be sequenced (FIG. 1A). Seven of these BACs (A, B, C, D, E, F and G), covering approximately 70% of the region of interest, have already been sequenced. The sequences of these 7 BACs were compared with those of the nucleic acid and protein databases, and analyzed with four exon prediction programs. These preliminary sequence-analyses made it possible to reveal 14 potential transcription units, including three corresponding to the genes encoding xanthine dehydrogenase, steroid 5α-reductase 2 and a TGFβ-binding protein. Of the 14 genes detected by the sequence analysis, 9 had been previously identified in the EST (for "Expressed Sequence Tag") databases and located-in the SPG4 range (Hazan et al., in press in Genomics); the 5 remaining genes could only be identified by sequencing the candidate region. One of these 5 novel genes showed homology in 3' of its coding region, with the genes encoding the AAA protein family (Confalonieri et al., 1995). More thorough sequence analyses showed that this gene, named SPG4 (or SPAST), was composed of 17 exons and extended over a region of approximately 90 kb, covered by two adjacent BAC clones, D and G (cf. FIG. 1B). The first three predicted exons of this gene were identified in BAC D, by two of the four exon prediction programs used, GRAIL II and GENSCAN; they show strong homology with a mouse blastocyst EST, AA560327. The last 14 exons are found in BAC G. The protein sequence deduced from exons 7 to 17 is significantly homologous to a subclass of the AAA family, which includes the Yta6p (Schnall et al., 1994), TBP6 (Schnall et al., 1994) and End 13 yeast proteins, and also the SKD1 mouse protein (Perier et al., 1994).

Of the four exon prediction programs FGENEH appears to be the most reliable and the most powerful, enabling detection of most of the genes of this chromosomal region at 2p21–p22. This observation also applies to the SPG4 gene, for which 15 exons could be demonstrated using this program, while only 4, 9 or 11 exons could be located using the Genie, GRAIL II and GENSCAN programs, respectively. The genomic organization of this gene (FIG. 1B) could subsequently be confirmed by determining the sequence of the SPG4 cDNA. The intron/exon junctions are represented on table 3 hereinafter: the exon size ranges from 41 bp (exon 16) to 1.410 kb (exon 17), that of the introns ranging from 140 bp (intron 11) to 23.247 kb (intron 1).

Example 4

Mutations in the SPG4 Gene

Heterozygous mutations were sought in the SPG4 cDNA originating from lymphoblasts of 14 patients derived from SPG4 locus-linked families (1 affected individual per family). Four overlapping PCR fragments, I, II, III and IV, covering the open reading frame of the SPG4 cDNA, were

TABLE 3

Intron/exon organization of the SPG4 gene

| Exon/ intron | Exon size (bp) | Position on the cDNA | Splice acceptor site (SEQ ID No. 74 to 89) | Splice donor site (SEQ ID Nos. 90 to 105) | intron size (bp) |
|---|---|---|---|---|---|
| 1 | 540 | 1 | | TGAGAAAG/gtaactaggggctgg | 23247 |
| 2 | 87 | 541 | atttttatttaaag/CAGGACAG | AGGACAAG/gtaagattgtatttgt | 1943 |
| 3 | 84 | 628 | aatttttctttcag/GTGAACAG | ACTTCTAG/gtatcaattaatgtat | 9190 |
| 4 | 96 | 712 | cttctctgttgcatag/AGAAGATG | CCAGTCAG/gtgggtttaggttaac | 15745 |
| 5 | 188 | 808 | acttttccttgtcag/AAAGTGGA | CTCATAAG/gtattctgggacagta | 876 |
| 6 | 134 | 996 | ttttgtatccttaag/GGTACTCC | GTGGACAA/gtaagttttgccatct | 283 |
| 7 | 94 | 1130 | aggtcttgttcttag/TGGAACAG | GGCCTGAG/gtaagaactttatatt | 10735 |
| 8 | 75 | 1224 | agtatatattttag/TTGTTCAC | CAATGCTG/gtaagggttctcttca | 1385 |
| 9 | 72 | 1299 | cttgtgatttttaaag/GCTAAAGC | CAAAATAC/gtgagtgctctgtttc | 8083 |
| 10 | 76 | 1371 | taatgctttgttttag/GTGGGAGA | TTTTATAG/gtaagaacatatttc | 238 |
| 11 | 92 | 1447 | cttgtatttcctctag/ATGAAGTT | TTGATGGT/gtaagtgttgattatg | 140 |
| 12 | 80 | 1539 | gatttttgcttgtag/GTACAGTC | GTTCTCAG/gtagggagatttatat | 4715 |
| 13 | 43 | 1619 | ggattttttttttag/GCGTTTCA | ATGAGGAG/gtatgtatctgtgttt | 1389 |
| 14 | 80 | 1662 | ttttaatattttcag/ACAAGACT | CTTGCTAG/gtgagtaatttggatt | 1521 |
| 15 | 71 | 1742 | tccttcccttcctcag/AATGACTG | TATCCGAG/gtaggtatacaagagc | 2210 |
| 16 | 41 | 1813 | cttttatgttttacag/AACTAAAA | CCAGTGAG/gtatagtattttacaa | 7115 |
| 17' | 1410 | 1854 | cttttaaaaatctag/ATGAGAAA | | |

The sequences of the exons and introns are indicated in upper case and lower case, respectively.

Example 3

Identification of the SPG4 cDNA

Several successive amplifications by 5' and 3' RACE-PCR were carried out on collections of adult liver and brain and fetal brain cDNA, in order to characterize the SPG4 transcript. All the 5' RACE-PCRs gave amplification products terminating at nt position 263 of the SPG4 cDNA (FIG. 2), which was probably due to the rich GC content of the 5' region of the transcript (90% of GC in the 60 bp preceding nt position 263). Four overlapping PCR products, covering all of the coding region, were amplified from the cDNAs derived from the lymphoblasts of six control individuals, and entirely sequenced with the aim of verifying the sequence of the SPG4 transcript. Aligning the sequences of all the PCR and RACE-PCR products made it possible to reconstitute a 3263 bp sequence comprising a 1848 bp open reading frame preceded by a 125 bp untranslated 5' region (5' UTR for "5' UnTranslated Region") and followed by 1290 bp 3' UTR region including a polyadenylation site between nt positions 3227–3232, ~35 bp upstream of the polyA tail (FIG. 2). Comparing the sequence of the SPG4 cDNA with the EST databanks made it possible to detect significant homology with 6 human ESTs, including EST N47973 which contains a more extended 3' noncoding region (+180 bp) comprising a second polyadenylation site. The translation initiation site was identified by the presence of a Kosak consensus sequence (CTGTGAatgA) defined as a "suitable context" for translation initiation given that a purine is located 3 nt upstream of the initiator ATG, itself preceded by a STOP codon. The 3263 bp cDNA sequence is identical to the transcribed sequence deduced from the 17 exons of the SPG4 gene. The analysis of the sequence of the 5' region using the TSSG and TSSW computer programs suggests the presence of a promoter sequence of the TATA box type located 43 bp upstream of nt position 1 of exon 1.

amplified and sequenced in the 14 patients, and also in 6 healthy control individuals. The agarose gel electrophoresis of PCR fragment IV showed three bands of equal intensity in 3 patients from families 2992, 5226 and 5330 originating from the same region of Switzerland, which would suggest a microdeletion or a mutation of a splice site; the two additional bands were not present in 2 healthy individuals derived from families 2992 and 5330 (FIG. 3A). The genomic sequence of exon 16 revealed a heterozygous A→G mutation of the splice acceptor site (AG) of intron 15 in the affected individuals of these three families (FIG. 3B); this mutation engenders the loss of exon 16, followed by a reading frame shift in the abnormal transcript. None of the healthy members, including husbands and wives, carry this mutation of the splice site. The identification of the same mutation in all the affected members of these three Swiss families demonstrates the existence of a common ancestor, which had probably been suggested by the study of the haplotypes.

Three point mutations, 1210C→G, 1468G→A and 1620C→T, which introduced amino acid substitutions into the protein sequence (S362C, C448Y and R499C), were respectively revealed by sequencing PCR fragments III and IV in the affected individuals of families 624, 4014 and 618. These three substitutions all involve a cysteine residue, inducing the loss or insertion of a cysteine in the protein sequence. A 1 bp deletion, 1520delT, which creates the appearance of a STOP codon inducing a truncated protein composed of 465 amino acids (aa), was detected in the affected individuals of family A. None of the five mutations summarized in table 4 hereinafter was found in the control individuals tested, whether they belong to the healthy siblings or to the spouses of the seven families analyzed herein. These five mutations significantly affect the protein sequence in a very conserved domain, or AAA cassette (Beyer, 1997), which is composed of several protein motifs presumed to be responsible for the ATPase activity in all the members of the AAA family.

TABLE 4

Mutations in SPG4 in the patients suffering from AD-HSP

| Family | Location | Mutation[a] | Amino acid change[b] | Consequence |
|---|---|---|---|---|
| 624 | exon 7 | 1,210 C ↦ G | S362C | missense |
| 4014 | exon 11 | 1,468 G ↦ A | C448Y | missense |
| A | exon 11 | 1,520 delT | 466STOPcodon | nonsense |
| 618 | exon 13 | 1,620 C ↦ | TR499C | missense |
| 2992 | intron 15 | 1,813-2a ↦ g | Δ aa564 ↦ aa576 (PTC+7 aa) | loss of exon 16 + shift |
| 5226 | intron 15 | 1,813-2a ↦ g | Δ aa564 ↦ aa576 (PTC+7 aa) | loss of exon 16 + shift |
| 5330 | intron 15 | 1,813-2a ↦ g | Δ aa564 ↦ aa576 (PTC+7 aa) | loss of exon 16 + shift |

[a]The nt positions refer to the sequence of the SPG4 cDNA.
[b]The aa positions refer to the spastin sequence.
The bases of the exons are indicated in upper case, those of the introns in lower case.
PTC+7 aa = "premature termination codon" at 7 aa downstream of exon 16.

In addition to these five mutations described above, searches for heterozygous mutations, carried out on patients suffering from AD-HSP derived from 36 other families, made it possible to reveal 34 other mutations which modified or were likely to modify the product of expression of the SPG4 gene.

The characteristics of these 34 other mutations are summarized in table 5 hereinafter, into which the first five mutations mentioned above have also been inserted.

TABLE 5

Mutations in SPG4 in the patients suffering from AD-HSP

| Family | Location | Mutation[a] | Amino acid change[b] | Consequence |
|---|---|---|---|---|
| 624 | exon 7 | 1210 C ↦ G | S362C | missense |
| 6958 | exon 8 | 1233 G ↦ A | G370R | missense |
| 214 | exon 8 | 1267 T ↦ G | F381C | missense |
| 1002 | exon 8 | 1283 T ↦ G | N386K | missense |
| 027 | exon 8 | 1288 A ↦ G | K388R | missense |
| 019 | exon 10 | 1401 C ↦ G | L426V | missense |
| 4014 | exon 11 | 1468 G ↦ A | C448Y | missense |
| 148 | exon 11 | 1504 G ↦ T | R460L | missense |
| 618 | exon 13 | 1620 C ↦ T | R499C | missense |
| 636 | exon 15 | 1788 G ↦ A | D555N | missense |
| 627 | exon 15 | 1792 C ↦ T | A556V | missense |
| 2971 | exon 3 | 702 C ↦ T | Q193STOP | nonsense |
| 3655 | exon 5 | 873 A ↦ T | K229STOP | nonsense |
| 1010 | exon 5 | 907 C ↦ A | S261STOP | nonsense |
| 3938 | exon 5 | 932 C ↦ G | Y269STOP | nonsense |
| 6922 | exon 10 | 1416 C ↦ T | R431STOP | nonsense |
| 616 | exon 10 | 1416 C ↦ T | R431STOP | nonsense |
| 605 | exon 15 | 1809 C ↦ T | R562STOP | nonsense |
| 030 | exon 2 | 578–579insA | PTC + 2 aa | shift + nonsense |
| 615 | exon 5 | 852del11 | PTC + 18 aa | shift + nonsense |
| 042 | exon 5 | 882–883insA | PTC + 12 aa | shift + nonsense |
| 032 | exon 5 | 906delT | PTC + 17 aa | shift + nonsense |
| 189 | exon 9 | 1299delG | PTC + 3 aa | shift + nonsense |
| 3686 | exon 9 | 1340del5 | PTC + 35 aa | shift + nonsense |
| 625 | exon 9 | 1340del5 | PTC + 35 aa | shift + nonsense |
| A | exon 11 | 1520delT | PTC + 7 aa | shift + nonsense |
| 115 | exon 12 | 1574delGG | PTC + 2 aa | shift + nonsense |
| 3266 | exon 13 | 1634del22 | PTC + 18 aa | shift + nonsense |
| 149 | exon 14 | 1684–1685insTT | PTC + 9 aa | shift + nonsense |
| 645 | exon 14 | 1685del4 | PTC + 7 aa | shift + nonsense |
| 029 | intron 4 | 808–2 a ↦ g | ? | splice site mutation |
| 162 | intron 6 | 1129+2 t ↦ g | ? | splice site mutation |
| 125 | intron 7 | 1223+1 g ↦ t | ? | splice site mutation |
| 143 | intron 8 | 1299+1 g ↦ a | ? | splice site mutation |
| 1620 | intron 11 | 1538+5 g ↦ a | (PTC + 6 aa) | loss of exon 11 + shift |
| 1006 | intron 11 | 1538+3 del4 | ? | splice site mutation |
| 1605 | intron 13 | 1661+1 g ↦ t | ? | splice site mutation |
| 1012 | intron 13 | 1662–2 a ↦ t | ? | splice site mutation |
| 1626 | intron 15 | 1812+1 g ↦ a | ? | splice site mutation |
| 2992 | intron 15 | 1813–2 a ↦ g | Δ aa564 ↦ aa576 (PTC+7 aa) | loss of exon 16 + shift |
| 5226 | intron 15 | 1813–2 a ↦ g | Δ aa564 ↦ aa576 (PTC+7 aa) | loss of exon 16 + shift |
| 5330 | intron 15 | 1813–2 a ↦ g | Δ aa564 ↦ aa576 (PTC+7 aa) | loss of exon 16 + shift |
| 1611 | intron 16 | 1853+1 g ↦ a | ? | splice site mutation |

[a]The nt positions refer to the sequence of the SPG4 cDNA.
[b]The aa positions refer to the spastin sequence.
The exon bases are indicated in upper case, those of the introns in lower case.
PTC+n aa - "premature termination codon" at n amino acids downstream of the mutation.

Example 5

Analysis of the Protein Sequence of Spastin

The open reading frame of SPG4 encodes a 616 aa protein which we have named spastin and the molecular weight of which is approximately 67.2 kDaltons (kD). The comparison of this amino acid sequence in the protein databases, using the BLAST programs, made it possible to reveal a region of strong homology with several members of the AAA family, at the C-terminal end of spastin. The "typical" motifs of the AAA family, encompassed in the AAA cassette, are located between aa positions 342 and 599 (see FIG. 2) according to the sequence comparisons in the ProDom and Prosite protein domain databases. The three conserved typical domains, including the Walker A and B motifs and also the minimum consensus motif of the AAA proteins are located in the AAA cassette at aa positions 382–389, 437–442 and 480–498, respectively, (FIG. 2). The Walker A motif, "GPPGNGKT", also called p-loop, which corresponds to the ATP-binding domain, and the B motif, "IIFIDE", are very conserved among all the members of the AAA family, including spastin.

The comparison of the AAA cassettes present in 150 proteins of this ATPase family, derived from organisms which are very far apart in evolution made it possible to classify this set of proteins into several subgroups, as a function of the number of AAA cassettes identified (1 or 2) and of the sequence homologies between these various cassettes (Beyer, 1997). Among all the proteins of the AAA family, spastin shows stronger homology with a particular subclass of the AAAs, and more specifically with the following proteins, most of which were identified through the complete sequencing of the genome of the organism in question: two proteins of Caenorhabditis elegans, O16299 and Q18128; two subunits of the 26S proteasome of Saccharomyces cerevisiae, Yta6p (Q02845) and TBP6 (P40328) (Schnall et al., 1994); a subunit of the proteasome of Schizosaccharomyces pombe (O43078); the SAP1 (P39955) and END13 (P52917) proteins of S. cerevisiae and the murine SKD1 protein (P46467) (Perier et al., 1994). The multiple alignment of these 8 proteins with spastin is represented in FIG. 4A. Of the 257 amino acids encompassing the AAA cassette (aa positions 342–599), spastin shows 52%, 51% and 50% sequence identity with the Yta6p (Q02845) yeast protein, the O16299 nematode protein and the TBP6 (P40328) yeast protein, respectively. Similar results were obtained by analyzing the protein sequence of spastin in the ProDom database, which showed the existence of three domains of homology (named 92, 179 and 6226, and corresponding to aa positions 342–409, 411–509 and 512–599) found in the putative subunits of the 26S proteasome of yeast. In addition, the members of this AAA subgroup most commonly contain motifs of the leucine-zipper type, two of which could be detected in the protein sequence of spastin at aa positions 50–78 and 508–529, by analyzing the sequence in the Prosite database (see FIG. 2). This analysis was also able to predict the presence of a dimerization motif of the helix-loop-helix type, located between aa positions 478 and 486.

The comparison of the protein sequence of spastin with those of the mitochondrial metalloproteases, such as the AFG3, RCA1 and YME1⁻ yeast proteins, and also paraplegin, which is implicated in a rare form of AR-HSP, shows that the homology between these five members of the AAA family is limited to the 257aa region encompassing the AAA cassette (FIG. 4B). In this region, the sequence identity between spastin and paraplegin is only 29%, whereas paraplegin and the AFG3 yeast protein are 57% identical over this same portion of the protein sequence. This sequence comparison suggests that spastin does not belong to the same AAA subgroup as paraplegin and other mitochondrial metalloproteases. In addition, the computer analysis of the spastin sequence using the PSORT II program, which makes it possible to predict the subcellular location of the proteins, appears to indicate that spastin is a nuclear protein. A possible nuclear localization signal (NLS), RGKKK, was revealed between aa positions 7 and 11, whereas no signal peptide characteristic of importation into mitochondria could be detected, unlike what had been observed for paraplegin.

Example 6

Expression Profiles for SPG4 and for its Mudne Ortholog Spq4

The comparison of the nucleic acid sequence of SPG4 in the EST databanks made it possible to detect several human, murine and rat ESTs showing strong homology with SPG4. The mouse blastocyst and E8 embryo cDNA clones corresponding to two of the murine ESTs, AA560327 and AA107866, were obtained from the IMAGE consortium and entirely sequenced. The assembly of the sequences of these cDNA clones made it possible to reconstitute a 1689 bp consensus sequence including a 1514 bp incomplete open reading frame. The comparison between the human SPG4 cDNA and this mouse cDNA showed that the murine transcript lacks approximately 460 bp at the 5' end, including the translation initiation codon. The mouse open reading frame is followed by a 175 bp 3' noncoding region (3' UTR) containing a polyadenylation site located ~20 bp upstream of the polyA tail (FIG. 5). The nucleic acid sequence of SPG4 and the protein sequence of human spastin show 89% (between nt positions 460 and 1982) and 96% (between aa positions 113 and 616) identity, respectively, with the mouse cDNA and deduced protein sequences. This considerable degree of homology makes it possible to affirm that this mouse transcript corresponds to the murine ortholog of SPG4, which was therefore named Spg4.

The hybridization of Northern blots comprising the mRNAs of various human and murine tissues (Clontech) with the SPG4 and Spg4 cDNA clones did not give any convincing results, except a very weak band corresponding to a 2.5 kb transcript in the mouse testicle after exposure for 10 days. Because of the low level of expression of this gene, the expression profiles for SPG4 and Spg4 were determined by PCR experiments on normalized collections of cDNA originating from various adult and fetal tissues (see FIG. 6A to 6C). The murine Spg4 gene is expressed ubiquitously in the adult tissues of mice, and also from the E7 stage to the E17 stage of mouse embryos (FIG. 6A). Higher expression of Spg4 was detected in the liver, skeletal muscle and testicles, and also at the E15 stage of embryos. The early expression of Spg4 during embryonic development was confirmed by the presence of ESTs originating from blastocyst, E8 embryo and embryonic carcinoma cDNA libraries in the public EST databanks. The human SPG4 gene is, itself, also expressed ubiquitously in adult (FIG. 6B) and fetal (FIG. 6C) tissues, with perhaps more marked expression in fetal brain.

Example 7

No Oxidative Phosphorylation Impairment in SPG4 Locus-linked AD-HSP

In order to determine whether spastin mutations induced an oxidative phosphorylation (OXPHOS) impairment in mitochondria, in the same way as had been observed for paraplegin, a muscle biopsy was performed on a patient from one of the SPG4 locus-linked AD-HSP families. The morphological and histo-enzymatic analyses of this muscle biopsy did not reveal any muscle fibers of the RRF (for "ragged red fiber") type, characteristic of OXPHOS impairments in mitochondria. The fact that all the muscle fibers appear to be normal, and also the prediction of a nuclear localization for spastin, seem to indicate that SPG4 locus-linked AD-HSP is not a mitochondrial disease of the OXPHOS type, unlike SPG7 locus-linked AR-HSP.

Using a positional cloning approach based on sequencing a 1.5 Mb region, we have identified the SPG4 (or SPAST) gene responsible for the most common form of AD-HSP, previously located on chromosomal bands 2p21–p22. Thirty nine mutations which modify or are likely to modify the gene product, named spastin, could be detected in the affected individuals from forty one families with AD-HSP showing a link to the SPG4 locus. Spastin is a novel member of the AAA protein family, which appears to have a nuclear localization and which shows strong homology with the subunits of the 26S proteasome of yeast. Despite great homology restricted to a domain of 230 to 250 aa, termed AAA cassette, the many members of this protein family can participate in very varied cellular mechanisms, such as the transport of proteins in vesicles, cell cycle regulation, organelle biogenesis, i.e. control of transcription, etc. However, all these cellular mechanism involve the assembly, the functioning or the degradation of protein complexes, which suggest that the members of the AAA family are so-called "chaperon" proteins.

References

Barany, F., (1991), Proc. Natl. Acad. Sci. USA, 88, 189–193.
Beyer, A. Sequence analysis of the AAA protein family. Protein Sci. 6, 2043–2058 (1997).
Bodansky M., Principles of peptide synthesis, (1984).
Bruyn, R. P. M. & Scheltens, P. H. Hereditary spastic paraparesis (Strumpell-Lorrain) in Handbook of clinical neurology Vol. 15 (ed. de Jong, J. M. B. V.) 301–318 (Elsevier Science Publishers B.V., 1991).
Buckholz, R. G. Curr. Op. Biotechnology 4: 538–542, 1993.
Burg, J. L. et al. (1996), Mol. and Cell. Probes, 10, 257–271.
Carter, B. J. Curr. Op. Biotechnology 3: 533–539, 1993.
Casari, G. et al. Spastic paraplegia and OXPHOS impairment caused by mutations in Paraplegin, a nuclear-encoded mitochondrial metalloprotease. Cell 93, 973–983 (1998).
Cherif D., Julier, C., Delattre, O., Derré, J., Lathrop, G. M., and Berger, R. Proc. Natl. Acad. Sci. USA. 87: 6639–6643, 1990.
Chu, B. C. F. et al. (1986), Nucleic Acids Res., 14, 5591–5603.
Chumakov, I., Rigault, P., Guillou, S., Ougen, P., Billault, A., Guasconi, G., Gervy, P., Le Chumakov, I. M., Rigault, P., Le Gall, I., et al. Nature 377: 175–183, 1995.
Confalonieri, F. & Duguet, M. A 200-amino acid ATPase module in search of a basic function. BioEssays 17, 639–650 (1995).
Duck, P. et al. (1990), Biotechniques, 9, 142–147.
Durr, A. et al. Phenotype of autosomal spastic paraplegia linked to chromosome 2. Brain 119, 1487–1496 (1996).
Edwards, C. P., and Aruffo, A. Curr. Op. Biotechnology 4: 558–563, 1993.
Epstein, A. Medecine/Sciences 8: 902–911, 1992.
Erlich, H. A., (1989), New York: Stockton Press.
Guatelli J. C. et al. Proc. Natl. Acad. Sci. USA 87: 1874–1878, 1990 et al. Cell 85: 281–290, 1996.
Fink, J. K. et al. Autosomal dominant familial spastic paraplegia: tight linkage to chromosome 15q. Am. J. Hum. Genet. 56, 188–192 (1995).
Hazan, J., Lamy, C., Melki, J., Munnich, A., de Recondo, J., & Weissenbach, J. Autosomal dominant familial spastic paraplegia is genetically heterogeneous and one locus maps to chromosome 14q. Nature Genet. 5, 163–167 (1993).
Hazan, J. et al. Linkage of a new locus for autosomal dominant familial spastic paraplegia to chromosome 2p. Hum. Mol. Genet. 3, 1569–1573 (1994).
Hedera, P. et al. Novel locus for autosomal dominant hereditary spastic paraplegia, on chromosome 8q. Am. J. Hum. Genet. 64, 563–569 (1999).
Heinzlef, O. et al. Mapping of a complicated familial spastic paraplegia to locus SPG4 on chromosome 2p. J. Med. Genet. 35, 89–93 (1998).
Hentati, A. et al. Linkage of a locus for autosomal dominant familial spastic paraplegia to chromosome 2p markers. Hum. Mol. Genet. 3, 1867–1871 (1994).
The Hereditary Spastic Paraplegia Working Group. Hereditary spastic paraplegia: advances in genetic research. Neurology 46, 1507–1514 (1996).
Innis, M. A. et al. (1990), Academic Press.
Jouet, M. et al. X-linked spastic paraplegia (SPG1), MASA syndrome and X-linked hydrocephalus result from mutations in the L1 gene. Nature Genet. 7, 402–407 (1994).
Kievitis, T. et al. (1991), J. Virol. Methods, 35, 273–286.
Köhler et Milstein. Nature 256, 495–497, 1975.
Kwoh, D. Y. et al. (1989), Proc. Natl. Acad. Sci. USA, 86, 1173–1177.
Landegren U., Kaiser R., Sanders J. & Hood L. Science 241: 1077–1080, 1988.
Lizardi, P. M. et al. (1988), Bioltechnology, 6, 1197–1202.
Luckow, V. A. (1993), Curr. Op. Biotechnology 4, 564–572.
Matthews, J. A. et al. (1988), Anal. Biochem., 169: 1–25.
Miele, E. A. et al. (1983), J. Mol. Biol., 171: 281–295.
Nielsen, J. E. et al. CAG repeat expansion in autosomal dominant pure spastic paraplegia linked to chromosome 2p21–24. Hum. Mol. Genet. 6, 1811–1816 (1997).
Olins, P. O., and Lee, S. C. Curr. Op. Biotechnology 4: 520–525, 1993.
Osoegawa, K. et al. An improved approach for construction of bacterial artificial chromosome libraries. Genomics 52, 1–8 (1998).
Perier, F. et al. Identification of a novel mammalian member of the NSF/CDC48p/Pas1p/TBP-1 family through heterologous expression in yeast. FEBS lett. 351, 286–290 (1994).
Perricaudet, M., Stratford-Perricaudet, L. and Briand, P. La Recherche 23: 471–473, 1992.
Polo, J. M., Calleja, J., Combarros, O. & Berciano, J. Hereditary ataxias and paraplegias in Cantabria, Spain. An epidemiological and clinical study. Brain 114, 855–866 (1991).
Reid, E. Pure hereditary spastic paraplegia. J. Med. Genet. 34, 499–503 (1997).
Rohlmann, A., Gotthardt, M., Willnow, T. E., Hammer, R. E., and Herz, J. Nature Biotech. 14: 1562–1565, 1996.
Rolfs, A. et al. (1991), Berlin: Springer-Verlag.
Sambrook, J., Fritsch, E. F., and Maniatis, T. Molecular cloning: a laboratory manual.
Saugier-Veber, P. et al. X-linked spastic paraplegia and Pelizaeus-Merzbacher disease are allelic disorders at the proteolipid protein locus. Nature Genet. 6, 257–262 (1994).
Schnall, R. et al. Identification of a set of yeast genes coding for a novel family of putative ATPases with high similarity to constituents of the 26S protease complex. Yeast 10, 1141–1155 (1994).
Scott, W. K. et al. Locus heterogeneity, anticipation, and reduction of the chromosome 2p minimal candidate region in autosomal dominant familial spastic paraplegia. Neurogenetics 1, 95–102 (1997).
Sec. Ed. Cold Spring Harbor Lab., Cold Spring Harbor, N.Y.
Segev, D., (1992), Kessler C. Springer Verlag, Berlin, New-York, 197–205.
Skre, H. Hereditary spastic paraplegia in Western Norway. Clin. Genet. 6, 165–183 (1974).
Stone, B. B. et al. (1996). Mol. and Cell. Probes, 10: 359–370.
Stewart J. M. et Yound J. D., solid phase peptides synthesis, Pierce Chem. Company, Rockford, 111, 2ème éd., (1984).

Suggs S. V., Wallace R. B., Hirose T., Kawashima E. H. and Itakura K. PNAS 78: 6613–6617, 1981.

Temin, H. M. Retrovirus vectors for gene transfer. In Kucherlapati R., ed. Gene Transfer, New York, Plenum Press, 149–187, 1986.

Walker G. T., Fraiser M. S., Schram J. L., Little M. C., Nadeau J. G., & Malinowski D. P. Nucleic Acids Res. 20: 1691–1696, 1992.

Werdedin, L. Hereditary ataxias. Occurence and clinical features. Acta Neurol. Scand. 73 (Suppl. 106) (1986).

Woo S. L. C. Methods Enzymol. 68: 389, 1979.

What is claimed and desired to be secured by Letters Patent of the United States is:

1. A method for genotypic diagnosis of AD-HSP associated with the presence of at least one mutation on a sequence of the human SPG4 gene, comprising the steps of:
   a) obtaining a biological sample from a patient,
   b) where appropriate, isolation of the genomic DNA from the biological sample to be analyzed, or production of cDNA from the RNA of the biological sample;
   c) specific amplification of said DNA sequence of the human SPG4 gene likely to contain a mutation, using primers comprising a sequence selected from the group consisting of SEQ ID NO:1, at least 15 consecutive nucleotides of SEQ ID NO:1 and, a sequence complementary to SEQ ID NO:1;
   d) analysis of the amplification products obtained and comparison of their sequence with the corresponding normal sequence of the human SPG4 gene,
wherein, if the amplification products comprise a sequence associated with the presence of at least one mutation in a sequence of the human SPG4 gene, AD-HSP is diagnosed in the patient.

2. A method for detecting one or more polymorphisms in the human SPG4 gene of a human biological sample, said method comprising:
   a) Amplifying human SPG4 gene DNA of the sample thereby obtaining an amplification product,
   b) sequencing the amplification product, thereby obtaining a DNA sequence of the amplification product; and
   c) comparing the DNA sequence of the amplification product with the DNA sequence of a wild-type human SPG4 gene;
whereby, if the DNA sequence of the amplification product is different from the DNA sequence of the wild-type human SPG4 gene, then one or more polymorphisms in the human SPG4 gene of the sample have been detected.

3. The method of claim 2, wherein the DNA in the sample is genomic DNA.

4. The method of claim 2, wherein the DNA in the sample is cDNA.

5. The method of claim 2, wherein the human biological sample is an antenatal human biological sample.

6. The method of claim 2, wherein the human biological sample comprises lymphoblasts.

7. The method of claim 2, wherein amplifying the DNA is performed by a method selected from the group consisting of: polymerase chain reaction, strand displacement amplification, transcription-based amplification system, self-sustained sequence replication, nucleic acid sequence based amplification, transcription mediated amplification, ligase chain reaction, repair chain reaction and cycling probe reaction.

8. A method for detecting one or more polymorphisms in the human SPG4 gene of a human biological sample, said method comprising:

d) amplifying the human SPG4 gene DNA of the sample thereby obtaining an amplification product, e) sequencing the amplification product, thereby obtaining a DNA sequence of the amplification product; and f) comparing the DNA sequence of the amplification product with the DNA sequence of the wild-type human SPG4 gene;

whereby, if the DNA sequence of the amplification product is different from the DNA sequence of the wild-type human SPG4 gene, then one or more polymorphisms in the human SPG4 gene of the sample have been detected, wherein at least one primer is used, and wherein the primer comprises any of the following:

the complement of nucleotides 383–405 of SEQ ID NO:1;
the complement of nucleotides 10278–10303 of SEQ ID NO:1;
the complement of nucleotides 10262–10236 of SEQ ID NO:1;
nucleotides 33728–33753 of SEQ ID NO:1;
nucleotides 35800–35826 of SEQ ID NO:1;
nucleotides 45058–45083 of SEQ ID NO:1;
nucleotides 62007–62031 of SEQ ID NO:1;
nucleotides 91208–91231 of SEQ ID NO:1;
nucleotides 100783–100808 of SEQ ID NO:1;
nucleotides 9976–9994 of SEQ ID NO:1;
the complement of nucleotides 35802–35821 of SEQ ID NO:1;
nucleotides 10037–10055 of SEQ ID NO:1;
the complement of nucleotides 35751–35770 of SEQ ID NO:1;
nucleotides 10418–10437 of SEQ ID NO:1;
the complement of nucleotides 62373–62390 of SEQ ID NO:1;
nucleotides 61968–61987 of SEQ ID NO:1;
the complement of nucleotides 91202–91220 of SEQ ID NO:1;
nucleotides 62008–62027 of SEQ ID NO:1;
the complement of nucleotides 91182–91201 of SEQ ID NO:1;
nucleotides 83346–83365 of SEQ ID NO:1;
the complement of nucleotides 101044–101062 of SEQ ID NO:1;
the complement of nucleotides 9638–9657 of SEQ ID NO:1;
the complement of nucleotides 10666–10686 of SEQ ID NO:1;
nucleotides 9658–9677 of SEQ ID NO:1;
the complement of nucleotides 10615–10633 of SEQ ID NO:1;
nucleotides 33230–33249 of SEQ ID NO:1;
the complement of nucleotides 33832–33853 of SEQ ID NO:1;
nucleotides 33251–33269 of SEQ ID NO:1;
nucleotides 35065–35085 of SEQ ID NO:1;
the complement of nucleotides 35857–35876 of SEQ ID NO:1;
nucleotides 44934–44953 of SEQ ID NO:1;
the complement of nucleotides 45293–45312 of SEQ ID NO:1;
the complement of nucleotides 45169–45186 of SEQ ID NO:1;
nucleotides 60684–60702 of SEQ ID NO:1;
the complement of nucleotides 61494–61513 of SEQ ID NO:1;
nucleotides 60707–60725 of SEQ ID NO:1;
nucleotides 61660–61679 of SEQ ID NO:1;
the complement of nucleotides 62124–62143 of SEQ ID NO:1;
nucleotides 62267–62285 of SEQ ID NO:1;
the complement of nucleotides 62667–62686 of SEQ ID NO:1;
nucleotides 73071–73090 of SEQ ID NO:1;
the complement of nucleotides 73697–73717 of SEQ ID NO:1;
nucleotides 74168–74187 of SEQ ID NO:1;
the complement of nucleotides 75416–75435 of SEQ ID NO:1;
nucleotides 74553–74574 of SEQ ID NO:1;
nucleotides 82534–82553 of SEQ ID NO:1;
nucleotides 82582–82601 of SEQ ID NO:1;
nucleotides 83044–83062 of SEQ ID NO:1;
the complement of nucleotides 83594–83615 of SEQ ID NO:1,
nucleotides 87840–87859 of SEQ ID NO:1;
the complement of nucleotides 89181–89200 of SEQ ID NO:1;
the complement of nucleotides 88206–88225 of SEQ ID NO:1;
nucleotides 89181–89200 of SEQ ID NO:1;
the complement of nucleotides 90165–90183 of SEQ ID NO:1;
the complement of nucleotides 89833–89852 of SEQ ID NO:1;
nucleotides 90619–90638 of SEQ ID NO:1;
the complement of nucleotides 91675–91694 of SEQ ID NO:1;
the complement of nucleotides 91285–91302 of SEQ ID NO:1;
nucleotides 93216–93236 of SEQ ID NO:1;
the complement of nucleotides 94601–94619 of SEQ ID NO:1;
nucleotides 93340–93360 of SEQ ID NO:1;
nucleotides 100421–100439 of SEQ ID NO:1; and
the complement of nucleotides 100846–100865 of SEQ ID NO:1.

9. A method for detecting one or more polymorphisms in the human SPG4 gene of a human biological sample, said method comprising:

a) amplifying the human SPG4 gene DNA of the sample thereby obtaining an amplification product;

b) hybridizing the amplification product with a probe that hybridizes specifically with the DNA of the wild-type human SPG4 gene, to produce a hybridized DNA; and c) applying a method to detect one or more mismatches in the hybridized DNA;

whereby, if one or more mismatches are detected in the hybridized DNA, then one or more polymorphisms in the human SPG4 gene of the sample have been detected.

10. The method of claim 9, wherein the DNA in the sample is genomic DNA.

11. The method of claim 9, wherein the DNA in the sample is cDNA.

12. The method of claim 9, wherein the human biological sample is an antenatal human biological sample.

13. The method of claim 9, wherein the human biological sample comprises lymphoblasts.

14. The method of claim 9, wherein amplifying the DNA is performed by a method selected from the group consisting of: polymerase chain reaction, strand displacement amplification, transcription-based amplification system, self-sustained sequence replication, nucleic acid sequence based amplification, transcription mediated amplification, ligase chain reaction, repair chain reaction and cycling probe reaction.

15. The method of claim 9, wherein the probe comprises any of the following:

the complement of nucleotides 383–405 of SEQ ID NO:1;
the complement of nucleotides 10278–10303 of SEQ ID NO:1;
the complement of nucleotides 10262–10236 of SEQ ID NO:1;
nucleotides 33728–33753 of SEQ ID NO:1;
nucleotides 35800–35826 of SEQ ID NO:1;
nucleotides 45058–45083 of SEQ ID NO:1;
nucleotides 62007–62031 of SEQ ID NO:1;
nucleotides 91208–91231 of SEQ ID NO:1;
nucleotides 100783–100808 of SEQ ID NO:1;
nucleotides 9976–9994 of SEQ ID NO:1;
the complement of nucleotides 35802–35821 of SEQ ID NO:1;
nucleotides 10037–10055 of SEQ ID NO:1;
the complement of nucleotides 35751–35770 of SEQ ID NO:1;
nucleotides 10418–10437 of SEQ ID NO:1;
the complement of nucleotides 62373–62390 of SEQ ID NO:1;
nucleotides 61968–61987 of SEQ ID NO:1;
the complement of nucleotides 91202–91220 of SEQ ID NO:1;
nucleotides 62008–62027 of SEQ ID NO:1;
the complement of nucleotides 91182–91201 of SEQ ID NO:1;
nucleotides 83346–83365 of SEQ ID NO:1;
the complement of nucleotides 101044–101062 of SEQ ID NO:1;
the complement of nucleotides 9638–9657 of SEQ ID NO:1;
the complement of nucleotides 10666–10686 of SEQ ID NO:1;
nucleotides 9658–9677 of SEQ ID NO:1;
the complement of nucleotides 10615–10633 of SEQ ID NO:1;
nucleotides 33230–33249 of SEQ ID NO:1;
the complement of nucleotides 33832–33853 of SEQ ID NO:1;
nucleotides 33251–33269 of SEQ ID NO:1;
nucleotides 35065–35085 of SEQ ID NO:1;
the complement of nucleotides 35857–35876 of SEQ ID NO:1;
nucleotides 44934–44953 of SEQ ID NO:1;
the complement of nucleotides 45293–45312 of SEQ ID NO:1;
the complement of nucleotides 45169–45186 of SEQ ID NO:1;
nucleotides 60684–60702 of SEQ ID NO:1;
the complement of nucleotides 61494–61513 of SEQ ID NO:1;
nucleotides 60707–60725 of SEQ ID NO:1;
nucleotides 61660–61679 of SEQ ID NO:1;
the complement of nucleotides 62124–62143 of SEQ ID NO:1;
nucleotides 62267–62285 of SEQ ID NO:1;
the complement of nucleotides 62667–62686 of SEQ ID NO:1;
nucleotides 73071–73090 of SEQ ID NO:1;
the complement of nucleotides 73697–73717 of SEQ ID NO:1;
nucleotides 74168–74187 of SEQ ID NO:1;
the complement of nucleotides 75416–75435 of SEQ ID NO:1;
nucleotides 74553–74574 of SEQ ID NO:1;
nucleotides 82534–82553 of SEQ ID NO:1;
nucleotides 82582–82601 of SEQ ID NO:1;
nucleotides 83044–83062 of SEQ ID NO:1;
the complement of nucleotides 83594–83615 of SEQ ID NO:1;
nucleotides 87840–87859 of SEQ ID NO:1;
the complement of nucleotides 89181–89200 of SEQ ID NO:1;
the complement of nucleotides 88206–88225 of SEQ ID NO:1;
nucleotides 89181–89200 of SEQ ID NO:1;
the complement of nucleotides 90165–90183 of SEQ ID NO:1;
the complement of nucleotides 89833–89852 of SEQ ID NO:1;
nucleotides 90619–90638 of SEQ ID NO:1;
the complement of nucleotides 91675–91694 of SEQ ID NO:1;
the complement of nucleotides 91285–91302 of SEQ ID NO:1;
nucleotides 93216–93236 of SEQ ID NO:1;
the complement of nucleotides 94601–94619 of SEQ ID NO:1;
nucleotides 93340–93360 of SEQ ID NO:1;
nucleotides 100421–100439 of SEQ ID NO:1; and
the complement of nucleotides 100846–100865 of SEQ ID NO:1.

16. A method for diagnosing the presence or absence of an autosomal dominant hereditary spastic paraplegia in a human, wherein the autosomal dominant hereditary spastic paraplegia is associated with the presence of a mutation in the human SPG4 gene, the method comprising detecting the presence or absence of one or more mutations in the human SPG4 gene in a biological sample obtained from the human, wherein if the biological sample comprises a sequence associated with the presence of at least one mutation in the human SPG4 gene, an autosomal dominant hereditary spastic paraplegia is diagnosed in the human.

17. The method of claim 16, wherein detecting the presence or absence of one or more mutations in the human SPG4 gene comprises amplifying DNA of the biological sample obtained from the human using primers, determining the DNA sequence of the amplified product, and comparing the DNA sequence of the amplified product with the DNA sequence of the wild-type human SPG4 gene to detect one or more mutations in the human SPG4 gene in the biological sample.

18. The method of claim 17, wherein the DNA in the sample is genomic DNA.

19. The method of claim 17, wherein the DNA in the sample is cDNA.

20. The method of claim 17, wherein the biological sample is an antenatal human biological sample.

21. The method of claim 17, wherein the biological sample comprises lymphoblasts.

22. The method of claim 17, wherein amplifying the DNA is performed by a method selected from the group consisting of: polymerase chain reaction, strand displacement amplification, transcription-based amplification system, self-sustained sequence replication, nucleic acid sequence based amplification, transcription mediated amplification, ligase chain reaction, repair chain reaction and cycling probe reaction.

23. The method of claim 17, which uses at least one primer comprising any of the following:

the complement of nucleotides 383–405 of SEQ ID NO:1;
the complement of nucleotides 10278–10303 of SEQ ID NO:1;
the complement of nucleotides 10262–10236 of SEQ ID NO:1;
nucleotides 33728–33753 of SEQ ID NO:1;
nucleotides 35800–35826 of SEQ ID NO:1;
nucleotides 45058–45083 of SEQ ID NO:1;
nucleotides 62007–62031 of SEQ ID NO:1;
nucleotides 91208–91231 of SEQ ID NO:1;
nucleotides 100783–100808 of SEQ ID NO:1;
nucleotides 9976–9994 of SEQ ID NO:1;
the complement of nucleotides 35802–35821 of SEQ ID NO:1;
nucleotides 10037–10055 of SEQ ID NO:1;
the complement of nucleotides 35751–35770 of SEQ ID NO:1;
nucleotides 10418–10437 of SEQ ID NO:1;
the complement of nucleotides 62373–62390 of SEQ ID NO:1;
nucleotides 61968–61987 of SEQ ID NO:1;
the complement of nucleotides 91202–91220 of SEQ ID NO:1;
nucleotides 62008–62027 of SEQ ID NO:1;
the complement of nucleotides 91182–91201 of SEQ ID NO:1;
nucleotides 83346–83365 of SEQ ID NO:1;
the complement of nucleotides 101044–101062 of SEQ ID NO:1;
the complement of nucleotides 9638–9657 of SEQ ID NO:1;
the complement of nucleotides 10666–10686 of SEQ ID NO:1;
nucleotides 9658–9677 of SEQ ID NO:1;
the complement of nucleotides 10615–10633 of SEQ ID NO:1;
nucleotides 33230–33249 of SEQ ID NO:1;
the complement of nucleotides 33832–33853 of SEQ ID NO:1;
nucleotides 33251–33269 of SEQ ID NO:1;
nucleotides 35065–35085 of SEQ ID NO:1;
the complement of nucleotides 35857–35876 of SEQ ID NO:1;
nucleotides 44934–44953 of SEQ ID NO:1;
the complement of nucleotides 45293–45312 of SEQ ID NO:1;
the complement of nucleotides 45169–45186 of SEQ ID NO:1;
nucleotides 60684–60702 of SEQ ID NO:1;
the complement of nucleotides 61494–61513 of SEQ ID NO:1;
nucleotides 60707–60725 of SEQ ID NO:1;
nucleotides 61660–61679 of SEQ ID NO:1;
the complement of nucleotides 62124–62143 of SEQ ID NO:1;
nucleotides 62267–62285 of SEQ ID NO:1;
the complement of nucleotides 62667–62686 of SEQ ID NO:1;
nucleotides 73071–73090 of SEQ ID NO:1;
the complement of nucleotides 73697–73717 of SEQ ID NO:1;
nucleotides 74168–74187 of SEQ ID NO:1;
the complement of nucleotides 75416–75435 of SEQ ID NO:1;
nucleotides 74553–74574 of SEQ ID NO:1;
nucleotides 82534–82553 of SEQ ID NO:1;
nucleotides 82582–82601 of SEQ ID NO:1;
nucleotides 83044–83062 of SEQ ID NO:1;
the complement of nucleotides 83594–83615 of SEQ ID NO:1;
nucleotides 87840–87859 of SEQ ID NO:1;
the complement of nucleotides 89181–89200 of SEQ ID NO:1;
the complement of nucleotides 88206–88225 of SEQ ID NO:1;
nucleotides 89181–89200 of SEQ ID NO:1;
the complement of nucleotides 90165–90183 of SEQ ID NO:1;
the complement of nucleotides 89833–89852 of SEQ ID NO:1;
nucleotides 90619–90638 of SEQ ID NO:1;
the complement of nucleotides 91675–91694 of SEQ ID NO:1;
the complement of nucleotides 91285–91302 of SEQ ID NO:1;
nucleotides 93216–93236 of SEQ ID NO:1;
the complement of nucleotides 94601–94619 of SEQ ID NO:1;
nucleotides 93340–93360 of SEQ ID NO:1;

nucleotides 100421–100439 of SEQ ID NO:1; and
the complement of nucleotides 100846–100865 of SEQ ID NO:1.

24. The method of claim 16, wherein detecting the presence or absence of a mutation in the human SPG4 gene comprises amplifying DNA of the biological sample obtained from the human, hybridizing the amplified product with a probe that hybridizes specifically with the DNA of the wild-type human SPG4 gene, applying a method to detect the presence of one or more mismatches in the hybridized DNA, wherein the detection of one or more mismatches indicates one or more mutations in the human SPG4 gene in the biological sample.

25. The method of claim 24, wherein the DNA in the sample is genomic DNA.

26. The method of claim 24, wherein the DNA in the sample is cDNA.

27. The method of claim 24, wherein the biological sample is an antenatal human biological sample.

28. The method of claim 24, wherein the biological sample comprises lymphoblasts.

29. The method of claim 24, wherein amplifying the DNA is performed by a method selected from the group consisting of: polymerase chain reaction, strand displacement amplification, transcription-based amplification system, self-sustained sequence replication, nucleic acid sequence based amplification, transcription mediated amplification, ligase chain reaction, repair chain reaction and cycling probe reaction.

30. The method of claim 24, which uses at least one probe comprising any of the following:
the complement of nucleotides 383–405 of SEQ ID NO:1;
the complement of nucleotides 10278–10303 of SEQ ID NO:1;
the complement of nucleotides 10262–10236 of SEQ ID NO:1;
nucleotides 33728–33753 of SEQ ID NO:1;
nucleotides 35800–35826 of SEQ ID NO:1;
nucleotides 45058–45083 of SEQ ID NO:1;
nucleotides 62007–62031 of SEQ ID NO:1;
nucleotides 91208–91231 of SEQ ID NO:1;
nucleotides 100783–100808 of SEQ ID NO:1;
nucleotides 9976–9994 of SEQ ID NO:1;
the complement of nucleotides 35802–35821 of SEQ ID NO:1;
nucleotides 10037–10055 of SEQ ID NO:1;
the complement of nucleotides 35751–35770 of SEQ ID NO:1;
nucleotides 10418–10437 of SEQ ID NO:1;
the complement of nucleotides 62373–62390 of SEQ ID NO:1;
nucleotides 61968–61987 of SEQ ID NO:1;
the complement of nucleotides 91202–91220 of SEQ ID NO:1;
nucleotides 62008–62027 of SEQ ID NO:1;
the complement of nucleotides 91182–91201 of SEQ ID NO:1;
nucleotides 83346–83365 of SEQ ID NO:1;
the complement of nucleotides 101044–101062 of SEQ ID NO:1;
the complement of nucleotides 9638–9657 of SEQ ID NO:1;
the complement of nucleotides 10666–10686 of SEQ ID NO:1;
nucleotides 9658–9677 of SEQ ID NO:1;
the complement of nucleotides 10615–10633 of SEQ ID NO:1;
nucleotides 33230–33249 of SEQ ID NO:1;
the complement of nucleotides 33832–33853 of SEQ ID NO:1;
nucleotides 33251–33269 of SEQ ID NO:1;
nucleotides 35065–35085 of SEQ ID NO:1;
the complement of nucleotides 35857–35876 of SEQ ID NO:1;
nucleotides 44934–44953 of SEQ ID NO:1;
the complement of nucleotides 45293–45312 of SEQ ID NO:1;
the complement of nucleotides 45169–45186 of SEQ ID NO:1;
nucleotides 60684–60702 of SEQ ID NO:1;
the complement of nucleotides 61494–61513 of SEQ ID NO:1;
nucleotides 60707–60725 of SEQ ID NO:1;
nucleotides 61660–61679 of SEQ ID NO:1;
the complement of nucleotides 62124–62143 of SEQ ID NO:1;
nucleotides 62267–62285 of SEQ ID NO:1;
the complement of nucleotides 62667–62686 of SEQ ID NO:1;
nucleotides 73071–73090 of SEQ ID NO:1;
the complement of nucleotides 73697–73717 of SEQ ID NO:1;
nucleotides 74168–74187 of SEQ ID NO:1;
the complement of nucleotides 75416–75435 of SEQ ID NO:1;
nucleotides 74553–74574 of SEQ ID NO:1;
nucleotides 82534–82553 of SEQ ID NO:1;
nucleotides 82582–82601 of SEQ ID NO:1;
nucleotides 83044–83062 of SEQ ID NO:1;
the complement of nucleotides 83594–83615 of SEQ ID NO:1;
nucleotides 87840–87859 of SEQ ID NO:1;
the complement of nucleotides 89181–89200 of SEQ ID NO:1;
the complement of nucleotides 88206–88225 of SEQ ID NO:1;
nucleotides 89181–89200 of SEQ ID NO:1;
the complement of nucleotides 90165–90183 of SEQ ID NO:1;
the complement of nucleotides 89833–89852 of SEQ ID NO:1;
nucleotides 90619–90638 of SEQ ID NO:1;
the complement of nucleotides 91675–91694 of SEQ ID NO:1;
the complement of nucleotides 91285–91302 of SEQ ID NO:1;
nucleotides 93216–93236 of SEQ ID NO:1;
the complement of nucleotides 94601–94619 of SEQ ID NO:1;
nucleotides 93340–93360 of SEQ ID NO:1;
nucleotides 100421–100439 of SEQ ID NO:1; and
the complement of nucleotides 100846–100865 of SEQ ID NO:1.

31. The method of claim 16, wherein the mutation is detected using at least one nucleic acid comprising any of the following:

the complement of nucleotides 383–405 of SEQ ID NO:1;
the complement of nucleotides 10278–10303 of SEQ ID NO:1;
the complement of nucleotides 10262–10236 of SEQ ID NO:1;
nucleotides 33728–33753 of SEQ ID NO:1;
nucleotides 35800–35826 of SEQ ID NO:1;
nucleotides 45058–45083 of SEQ ID NO:1;
nucleotides 62007–62031 of SEQ ID NO:1;
nucleotides 91208–91231 of SEQ ID NO:1;
nucleotides 100783–100808 of SEQ ID NO:1;
nucleotides 9976–9994 of SEQ ID NO:1;
the complement of nucleotides 35802–35821 of SEQ ID NO:1;
nucleotides 10037–10055 of SEQ ID NO:1;
the complement of nucleotides 35751–35770 of SEQ ID NO:1;
nucleotides 10418–10437 of SEQ ID NO:1;
the complement of nucleotides 62373–62390 of SEQ ID NO:1;
nucleotides 61968–61987 of SEQ ID NO:1;
the complement of nucleotides 91202–91220 of SEQ ID NO:1;
nucleotides 62008–62027 of SEQ ID NO:1;
the complement of nucleotides 91182–91201 of SEQ ID NO:1;
nucleotides 83346–83365 of SEQ ID NO:1;
the complement of nucleotides 101044–101062 of SEQ ID NO:1;
the complement of nucleotides 9638–9657 of SEQ ID NO:1;
the complement of nucleotides 10666–10686 of SEQ ID NO:1;
nucleotides 9658–9677 of SEQ ID NO:1;
the complement of nucleotides 10615–10633 of SEQ ID NO:1;
nucleotides 33230–33249 of SEQ ID NO:1;
the complement of nucleotides 33832–33853 of SEQ ID NO:1;
nucleotides 33251–33269 of SEQ ID NO:1;
nucleotides 35065–35085 of SEQ ID NO:1;
the complement of nucleotides 35857–35876 of SEQ ID NO:1;
nucleotides 44934–44953 of SEQ ID NO:1;
the complement of nucleotides 45293–45312 of SEQ ID NO:1;
the complement of nucleotides 45169–45186 of SEQ ID NO:1;
nucleotides 60684–60702 of SEQ ID NO:1;
the complement of nucleotides 61494–61513 of SEQ ID NO:1;
nucleotides 60707–60725 of SEQ ID NO:1;
nucleotides 61660–61679 of SEQ ID NO:1;
the complement of nucleotides 62124–62143 of SEQ ID NO:1;
nucleotides 62267–62285 of SEQ ID NO:1;
the complement of nucleotides 62667–62686 of SEQ ID NO:1;
nucleotides 73071–73090 of SEQ ID NO:1;
the complement of nucleotides 73697–73717 of SEQ ID NO:1;
nucleotides 74168–74187 of SEQ ID NO:1;
the complement of nucleotides 75416–75435 of SEQ ID NO:1;
nucleotides 74553–74574 of SEQ ID NO:1;
nucleotides 82534–82553 of SEQ ID NO:1;
nucleotides 82582–82601 of SEQ ID NO:1;
nucleotides 83044–83062 of SEQ ID NO:1;
the complement of nucleotides 83594–83615 of SEQ ID NO:1;
nucleotides 87840–87859 of SEQ ID NO:1;
the complement of nucleotides 89181–89200 of SEQ ID NO:1;
the complement of nucleotides 88206–88225 of SEQ ID NO:1;
nucleotides 89181–89200 of SEQ ID NO:1;
the complement of nucleotides 90165–90183 of SEQ ID NO:1;
the complement of nucleotides 89833–89852 of SEQ ID NO:1;
nucleotides 90619–90638 of SEQ ID NO:1;
the complement of nucleotides 91675–91694 of SEQ ID NO:1;
the complement of nucleotides 91285–91302 of SEQ ID NO:1;
nucleotides 93216–93236 of SEQ ID NO:1;
the complement of nucleotides 94601–94619 of SEQ ID NO:1;
nucleotides 93340–93360 of SEQ ID NO:1;
nucleotides 100421–100439 of SEQ ID NO:1; and
the complement of nucleotides 100846–100865 of SEQ ID NO:1.

* * * * *

UNITED STATES PATENT AND TRADEMARK OFFICE
CERTIFICATE OF CORRECTION

PATENT NO. : 6,924,126 B1  
DATED : August 2, 2005  
INVENTOR(S) : Jean Weissenbach et al.

Page 1 of 1

It is certified that error appears in the above-identified patent and that said Letters Patent is hereby corrected as shown below:

Column 27,  
Line 43, delete "YMEI⁻" and insert -- YMEI --.  
Line 63, delete "Mudne" and insert -- Murine --.

Signed and Sealed this

Seventh Day of March, 2006

JON W. DUDAS  
*Director of the United States Patent and Trademark Office*

SEQUENCE LISTING

```
<160> NUMBER OF SEQ ID NOS: 107

<210> SEQ ID NO 1
<211> LENGTH: 110000
<212> TYPE: DNA
<213> ORGANISM: Homo sapiens
<220> FEATURE:
<221> NAME/KEY: exon
<222> LOCATION: (9932)...(10471)
<221> NAME/KEY: intron
<222> LOCATION: (10472)...(33718)
<221> NAME/KEY: exon
<222> LOCATION: (33719)...(33805)
<221> NAME/KEY: intron
<222> LOCATION: (33806)...(35748)
<221> NAME/KEY: exon
<222> LOCATION: (35749)...(35832)
<221> NAME/KEY: intron
<222> LOCATION: (35833)...(45022)
<221> NAME/KEY: exon
<222> LOCATION: (45023)...(45118)
<221> NAME/KEY: intron
<222> LOCATION: (45119)...(60863)
<221> NAME/KEY: exon
<222> LOCATION: (60864)...(61051)
<221> NAME/KEY: intron
<222> LOCATION: (61052)...(61927)
<221> NAME/KEY: exon
<222> LOCATION: (61928)...(62061)
<221> NAME/KEY: intron
<222> LOCATION: (62062)...(62344)
<221> NAME/KEY: exon
<222> LOCATION: (62345)...(62438)
<221> NAME/KEY: intron
<222> LOCATION: (62439)...(73173)
<221> NAME/KEY: exon
<222> LOCATION: (73174)...(73248)
<221> NAME/KEY: intron
<222> LOCATION: (73249)...(74633)
<221> NAME/KEY: exon
<222> LOCATION: (74634)...(74705)
<221> NAME/KEY: intron
<222> LOCATION: (74706)...(82788)
<221> NAME/KEY: exon
<222> LOCATION: (82789)...(82864)
<221> NAME/KEY: intron
<222> LOCATION: (82865)...(83102)
<221> NAME/KEY: exon
<222> LOCATION: (83103)...(83194)
<221> NAME/KEY: intron
<222> LOCATION: (83195)...(83334)
<221> NAME/KEY: exon
<222> LOCATION: (83335)...(83414)
<221> NAME/KEY: intron
<222> LOCATION: (83415)...(88129)
<221> NAME/KEY: exon
<222> LOCATION: (88130)...(88172)
<221> NAME/KEY: intron
<222> LOCATION: (88173)...(89561)
<221> NAME/KEY: exon
<222> LOCATION: (89562)...(89641)
<221> NAME/KEY: intron
<222> LOCATION: (89642)...(91162)
<221> NAME/KEY: exon
<222> LOCATION: (91163)...(91233)
<221> NAME/KEY: intron
<222> LOCATION: (91234)...(93443)
```

```
<221> NAME/KEY: exon
<222> LOCATION: (93444)...(93484)
<221> NAME/KEY: intron
<222> LOCATION: (93485)...(100599)
<221> NAME/KEY: exon
<222> LOCATION: (100600)...(102009)

<400> SEQUENCE: 1
taactgactc tgctgtgttt ccttggcatt atagctaatc aaattgagca ggtcaggtaa      60
cagtttatac ttacacctac tatttcaaaa ccatgagctc attcacattt tcactgaagt     120
aacaaatcct ccataaacta gaaaatctca aactggtgac tgggagtttt ggttttgttt     180
ttttgttgtt ttattttatt ttattttatt ttctagatgg agtcttgctc tgttgcccag     240
gctggaatgc aatggcatga tctcagctca ctgcaacctc cacctttcgg gttcaagcaa     300
tcctcctgcc tcaatcttcc aagtagctgg gactacagga atgagctgcc gcacctggcc     360
tggtttgttt gttttaaat tttgaggcca ggtgcagtgg cccatatctg tgatcccagc      420
actttgggag accaaggcag gccgattact tgaggtcagg agttcaagac cagccaggcc     480
aacatggtaa aaccatgtcg ctactaaaaa cacaaaaatt aggccgggca cggtggctca     540
cgtctataat cccagcactt tgggaggcca aggtgagtgg atcacctgag gtcaggaggt     600
caagaccagc ctggcaaaca tggtgaaacc ccgtctctat aaaaatacaa aaattagcc      660
gggtgtggtg gcgggcacct gtaatcccag ctattgggga ggctgaggca ggagaatcgc     720
ttgaacctgg gaggtggagg ttgcagtgag tcgagatggt gccactgacc tccagcctgg     780
gcaataagag cgagacgcca tctcaaaaat atataaata ataaataaaa atacaaaaag      840
tagctaggct ttgtggcagg cacctgtagt cccagctact taggaggctg aggcaggaga     900
attgcttgaa cccaggaggc ggaggttgca gtgagccaag attgtgccac tgcgttccag     960
cctgggtgac agagcaagac tccttctcaa aaataaataa ataaataat aaataataa     1020
ataaataaaa ttttgagctg ggcatgaaag ctgaggcagg aggatccctt gagcccagca    1080
gtttgagacc ccagtgagct ataattctga cactgcactt cagcctggct gacagaggga    1140
gaccgtgtat ctaaaaagaa taaaataaca atgattttg agccaataac tcttagccaa     1200
tagatttcac ataaaaattt agaattctgg tttctcttga aaaattaaaa aaatctgaca    1260
atgttaagct tcacattcct gaaaggcaaa aatcagtgga agctagctgg gtgctgtggc    1320
tcacgcctat aaacccagtg ctttgggagg ctagggtaag tggattggtt gagtccagga    1380
gtttgagatc agcctggcca acacagtcaa accccatctc tacaaaacat acaaaaatta    1440
gctgggatat ggtggtgtgc acttgtggtc ccaactactc aggaggctga ggcaggagga    1500
ccacttgagc cctggaggtt gaggggggcag tgagccatga ttgtgccact gcactccagc    1560
ctggacgaca gagagacatt gtctcaaaaa gaaaaaaaa aatcagctca gtgggagctg    1620
agtaacagct gtcctgttca attacaggat gcaactcttt agcttctcat agtttccatc    1680
attcacatca tacatgcatt tttgcatgcc acacaaccca cacatggaac ccatatatgt    1740
tatatgcctg accactgttg ctattggaag ttttggccac tgcattaaac tataaactcc    1800
atcttattaa tcctgacacc ccacttattg cctgatatat tgtccgtttc ttaatatcta    1860
ttcatagaac aaatgaatga ataatatgtg ccacattgtg gactcaattc agggagatga    1920
ctaatcattc acaattatgt ttttccttct taatacagag attggataat aattccccaa    1980
ttgttacttc tctcatccct cccctccaac catatctttt catttgtttt tcttattta     2040
ggttttctgc ctttttcaaa atcagccatt tcctcactgg actctacatg tgccattttt    2100
```

-continued

```
tttttttttt ttttactaat ttttttagtt gaaaagaggt ccttaatatc tgtcattggt      2160
ccacacttga aatctagaat ctctcgaatt gaaggtctga agagttcctt agaaggcaag      2220
tagggccgaa atatccaaaa aaaactattt gatggtaggc actgtggtaa ataaatatgg      2280
gttaaagtga taaagtgacc gaatgtcctg gattagttag cacagtacct agctccttct      2340
ttttgtcctt gtgaaactgt ctcagattcc attcaagatt aagtgtcctg aaagttctta      2400
caagctgaaa actgggaggc tctcacactg taggtagaat ggctagcagg gttgggatct      2460
catctaggca cattgcagaa ccagggtaac accaaggcat tattttttt ctttctttac      2520 ttttcttctt ttttttaga gacagggtct cattatgtta cccaggctgg attccaattc      2580
ctgagctcaa gtgatcctcc tgagtagctg ggacttcagg tgtgcaccgc tgtgtctgaa      2640
ggcactgttt tttttgtttt tttttgttttt tttgacacaa atttaggaag atgttaattc     2700
acaacagtct tgagactgag atataattcc aaggagcaga agatgtgagt ttagagcact      2760
aaaaaatgag attccagtag agtcagaaat ctgaaatggc attacagata taagagacaa      2820
aaacaaaatg tattgagctc tgtcatgttg caggcatcat gatggaggtt ttagatgtac      2880
tctttcattt tgtaatttt atagaggaat taactagaat agcaacccca gtcccactaa      2940
ctctaaatcc catatttta ccatacaaaa aaagagcaaa agtgcagaaa agcacagtca      3000
atattaagta caaccagata gcagagactc agtaaatggg aggccggagg cccgaaaccc      3060
aacataatgc ccatgaatga aagcccatca cttgcgcttc agggctaac aatatactta      3120 tttcataatt aaaatagaaa cagactatgt aaaaatatta ttcttgagat cccagatttt      3180
taccttaaat tactgaggca gtaagtgtaa ttaactaata tgtgatgttg ggcaaataac      3240
agactcttag agccccaaat tctttatttt aaaaaactga ggccagatga ggtggcttac      3300
acatgtaatc ccagcactgg ggatgccaaa gcaggcagat cacttgagct tgagcttagg      3360
agtttgagat cagcctgggc aacacggtta agacctcatc tctaaacaaa atacaaaaat      3420
tagccaaaca tggtggtgtg cacctgtgtt cctggctact caggaggctg aggtggaagg      3480
atcgcttgag cccgagaggt tgagggtgca gtgagccatg atcttgccat tgcactctac      3540
actctagtct gggtgacaga gtgagactct gtcttgggg aaaacaaaag agatgataat      3600
gcttaactga agtagcaata ttttaaaaag gcactaaaag ttcatctgct tagttcagaa      3660
tatgggttcg ataaatatta gcaagtagta gtagtcatca tcatcactgt cactgctgtt      3720
ctctccttaa acttaagcat gtttttgtt ttttttgagac agtgtctcac tctgtcaccc      3780
aagctggagt tcagtggtgt gatcttggct cactccaacc tctgcctccc aggttcaagt      3840
gattctcctg tctcaccctc ccaagtagct gggaccacag acacgtacca caaccacacc      3900
cagctaattt ttcgtatttt tggtagaggt ggggtttcac catgttggcc aggctggtct      3960
tgaactcctg acctcaagtg atccacctgt ctcggcctcc caaagtgctg ggattacagg      4020
cgttagccac agcatccagc cttaagcatg ttaattaagt ttttataatt cagcaaaatg      4080
gttggaaaat gctgtcttaa atgagatgct taagctgccg tctgaacatg aggtagaagg      4140
aaattctaca cataatcatt gtgctaaatt acttgcaaag atggccacaa caattcctcc      4200
tatcctcata tatatgcccc tttgcaatgt gactttgcta cttctctatc aagatgtgga      4260
gcttattttc ccatatattg cactagagtt ggccttctga cttgctttga caatggaatg      4320
tagtacaaat gacactgtgc aactttggat tttaggtttc gagagaactt acaccttcca      4380
ctcacactct cttggaaacc agatgcaatg taaagaagtc agggctatcc tgctagagac      4440
atatgtccca gctaatagcc acaatcaacc tctgaacata tgaatgaggc tagctaggcc      4500
```

-continued

```
atacagccat tcggtcaagc catcagatga ctacatccac aggaatgatc cacaggcaag    4560
gccatcagaa gaaccatcca gctgaactta ccccaaattg ctgagtcaca agttgtgtg     4620 taaataaatg tctgctatct taagccagtg agttttggag tggtatatta catagcatca    4680
gaaatctaac acaatcatta tgtttgaatc attttttcaaa tttctcatat ttattaaatg   4740
agtaccataa gcaaggtgtc aggctggatg caaaaagtga ggcaaaatgt ataaagtgtg    4800
accactgcct tcagtaagtt tacaatctat atcaagaggt gatgaagtgt ttaaataatc    4860
atcctgcagg gcaatatagt ataagagcca cagagtaaca caaccatatt gtcataacaa    4920
ctgaaaaaca agatcatttc tgctggaggt gataatggaa taatttatca agaatataac    4980
agagctggac gcggtggctc acacctgtaa tcccagcact ttgggaggcc aaggaaggtg    5040
gatcacaagg tcaggagttc gagaccatcc tggctaacac gatgaacccg tctctactaa    5100
aaatacaaga aattagccgg gcgtggtggc acgcgtctgt agtcgcagct actcaggagg    5160
ctgaggcagg agaaccactt gaacatggga agcagaggtt gcattgagct gagatcgtgc    5220
catggcactc cagcctgggt gacagagtga gactcagtct caaaaaaaaa aaaaaaaaa     5280 aaaatataac attagaggta agtcttgaag gactttgaca gtggaagtag gaggcgaggc    5340
cattctaagt gaatgaaaaa tgacaggaga gtaattgtag tcctggaaaa gagcaaagta    5400
ggtacagacc aacagtctat attagctaga gtatagtgaa agtgcagagg aaatgtcgga    5460
gaaccattct ttattcaaaa actatcttcc tcatggccaa gcatagtggc tcatgcctgt    5520
aatcccagca ttttgggagg tcaaggtgag tggatcactt gagctcagga attcaagacc    5580
atctggggca acatagtgag acctcatctc aactaaaaaa caaaaaattc agacagatgc    5640
agtggctcac acctgtaatc ccagaacttt ggtaggctga ggcgggcgga tcacgaggtc    5700
aggagatcaa gaccctcctg gacaacatgg agaaacccca tctctattaa aaatacaaaa    5760
ttagctgggc atggtggcac atccctgtaa tcccagctac tcgggaggct gaggcaggag    5820
aatcgcttga accagggagt cggaggttgc agtgagccga gatcgcacca ctgcactcca    5880
gtctggcgac agagcgagac tccatcttaa aaataaata aattttaaaa aaaactaccc     5940
cagcatggtg gtgcatgcct gtagtcccag ttactcagga ggctgaggca agagggtggt    6000
ttgagccagg gaggtcaagg ctgcagtgag ctctgatggc gccactgtac tccagcttgg    6060
gtgacagagt gagaccttgt ctcaaaaaca aaacaaaaa caaaaaacca acaaatctcc     6120
ttgttagtat catggtgagt aaaaaataaa ataaaaatag aaataaactg aacatggtgg    6180
ctcatgcctg taatcctagc actttggaag gctgaagtgg gaggattgct tgagggctgg    6240
agttcaaaac tggcttgggc aacacggtga gagagacctt gtctctacaa aagaactttt    6300
aaaacaaaaa atagataatt taaaaaaatt aaaaaaaaca aaaataaaa aataatcaa      6360 gtatcaactt gattccaggc actgcttact actctagtgt tatactgtag atgtggaagc    6420
tgagtaactc atccaagatc accgaaagtg atggaacaca gatctaaatg caaccagtct    6480
gactccagga ccatttaacc attctactat tgggccctat cttggctaag ttagaaagta    6540
agttactttc tttagtggta aagactggag ggataacagg gaagatagtt atttaagaaa    6600
aaaaactggc atcaaactaa atatccatca atagttgaac agtaaaatag gttgtggtaa    6660
attcatataa tggaatacta tatagcagtg aaaatgtacc acagttatag aaatcaacag    6720
ggaggaattt caacacttaa ttattaagta ggtagccagg catagcggtt tatgcctgta    6780
atcccagcac tttgggagac caagacagga ggattacttg agcccagggg ttcgagatca    6840
```

| | | | | | |
|---|---|---|---|---|---|
| acctgggcaa | cagtgagact | ccatctctat | tttcttaaaa | taaaataaat | gaaattttaa | 6900 |
| aaattttgag | gagggaaagc | aaacaaggga | tacttgaaat | atgattacat | ttccataaag | 6960 |
| tcaaagtgag | gcaaaatcat | acaagacatt | gtttagaaat | acataaatac | actgcaaact | 7020 |
| aaaaatgaga | cactagaatg | attaatataa | aattcaggat | agtggcttcc | tctagaggaa | 7080 |
| gagacaagac | attgagatta | gggaggagct | cacagagtgc | ttcgaggagt | tggttacatt | 7140 |
| cattttcctt | aaatggaatg | ctgcttatta | tttttcttta | aattgtgcat | ttaagtaaca | 7200 |
| cacttcttgt | ttatatgata | tatgtataaa | tgtaattttt | ttttttgaga | tggagtttcg | 7260 |
| ctcttgttgc | ccaggctgga | gtgcaatggc | actatcttgg | ctcactgcaa | cctccacttc | 7320 |
| ctgggttcaa | gtgattctcc | tgcctcagcc | tcccgagtag | ctgggattac | aggcatgcgc | 7380 |
| caccatgccc | ggctagtttt | gtattttaa | tagagaaagg | gtttctccat | gttggtcagg | 7440 |
| ctggtctcga | actcccgacc | tcaggtgatc | cgcctgcctt | ggcctcccaa | agtgttggga | 7500 |
| ttacaggtgt | gagccaccgt | gccaggccct | gaatcagatt | taaagagggg | catttcatta | 7560 |
| aaaaaattt | tttgttgttt | gcttttgaga | cagagtctcg | ctctgtcgcc | caggctgcag | 7620 |
| tgcattggca | tgatcttggc | tcaccgcggc | ctcagcctcc | caggttcaag | tgattctcct | 7680 |
| gcctcagcct | cgcactagtt | gagattacag | gaatgcacca | ccaccacagg | aatgcacctg | 7740 |
| tctaactttt | gtattttag | tatagaggga | gttttgccat | gttagccagg | ctgctcttga | 7800 |
| actcctgacc | tccggtgatc | tgctcgcctc | ggctcccaaa | gttctgggat | tacaggcgtg | 7860 |
| agccaccaca | cccggccgaa | agagggcatt | tcagaatgag | ggtctagcat | aagcacagag | 7920 |
| aaggggggagc | aataagaggg | aaacagggag | taggtcattt | ttgcaatagc | ctgtgacatt | 7980 |
| tgtaggcag | tactggcggg | gaataattaa | gtaaaattgg | ctggtgctgt | ggctcatgcc | 8040 |
| tgtaatccca | gcactttggg | aggccgaggc | gggcaggttg | cttgagccca | ggaattcaag | 8100 |
| accaacctgg | gaaacatagc | aagaccctgt | ctcaacaaaa | aagtaaaaaa | attagctggg | 8160 |
| ggcgcgatgg | ggtggctcat | gcctgtaatc | ccaacacttt | ggaaggctga | ggcaggcgga | 8220 |
| ttgcttgagc | ccaggagttg | gagaccagcc | tgggcaacat | ggtgaaaccc | tggctctata | 8280 |
| aagaatacaa | aaattagtcg | ggcccagtgg | cgtgtgcctg | tgatcccagc | tactcgggag | 8340 |
| gctgaggtgg | aaggatcacc | tgagccaggg | aggtggaggt | tgcagtgagt | catgttgttt | 8400 |
| gcgccactgc | actccagcct | gggcaatgga | gtgaaaccct | gtccaaaaaa | taaaaaaata | 8460 |
| aagctgtggc | agaatgtgga | gattcttgga | agctggaagc | tctcatgggg | catttggaaa | 8520 |
| cctcacattg | taaataacgg | agtctttta | tcagtttggc | ttccttagtt | ttaggaaaca | 8580 |
| agaaataatt | atggctaact | caagtaaaaa | gagaaagaga | agagaaaaaa | gacgtggaga | 8640 |
| tagagagaga | gggagagaga | ggaaaagacg | aaaggaagga | aggggaaag | gagagaggaa | 8700 |
| gagagaaaca | gagaaacaga | ctgattagtg | tattggatag | attacataac | caagtgacca | 8760 |
| gtcaggaacc | cagcagctct | gggggagctc | aatgtgatgc | attgataaac | ccgctcttaa | 8820 |
| gagcactcgt | ttccagttac | tttctattcg | gtgggtctcc | agccaagatt | ccaggtccca | 8880 |
| ggagaatctg | actgacctag | tgtttgcttc | cgcctttgcg | gtctgggttc | tgtgcttgca | 8940 |
| gctcattaga | atacagggag | cagagacaag | caggtagttt | cccaaaggaa | gggatgctga | 9000 |
| gtagattaaa | aaaaagtgt | agattcttca | gtaaactatg | ggatggtaac | tatgcaaaac | 9060 |
| ctaagatttc | ccttattcaa | ataaattatc | tttcatatta | gacatctaaa | tatgcactaa | 9120 |
| tttagttaaa | cccctgggtt | agttgatctc | atcacactga | gctaacattt | ttgttgctgt | 9180 |
| tgtttgcagt | gacctgaagt | ttcttatctt | cacaattgct | ttcctctcaa | ataattccca | 9240 |

```
gattttaaat ttttatttta ttttttctgg agacggagtc tcgctctgtc gcccaggctg   9300
gagtgcagtg gcgcgatctc agctcacttg cagcctctgc ctcccgagtt caagcgattc   9360
tccggcctta gccttccaac cagctgggac tacaggcgcg cgcccccacg cccggctaat   9420
ttaattccca gattgatatc cattgcttct gagatgggcc aattatcctt cggagaagac   9480
ttaggtcgcc tggcagaaaa agatgaaaga atctaagaa aacgacgaca ctgagagagg    9540
agcctagcga accagcagag cgaccccaag ccgcaattcc cccttccgtg gatcgattac   9600
gaaggcttcc tggcaggagc tctccagggc tgccgacgtg agccgaactg cacattggga   9660
actgtagttg agtgggaaag ccgagaggcg ggggccgcac acgcgtacag gggccccggt   9720
caacaaagac gcgccgtgcg cgcgcgcgcc ggagaaaaac acgggaagac gtgcgcgtgc   9780
gcggccgccg ctgggagcca ccaggcggcg gagaggacag cgacaggaag ggaggggccc   9840
gagccaccga ctgcaggagg agaaggggtt gtgctcctgg ccgaggaagg agaaaggggc   9900
ggggccggcg ggcagcgtgc ggcagtgcgg agctcctgag accggcgggc acacgggggt   9960
ctgtggcccc cgccgtagca gtggctgccg ccgtcgcttg gttcccgtcg gtctgcggga  10020
ggcgggttat ggcggcggcg gcagtgagag ctgtgaatga attctccggg tggacgaggg  10080
aagaagaaag gctccggcgg cgccagcaac ccggtgcctc ccaggcctcc gcccccttgc  10140
ctggcccccg cccctcccgc cgccgggccg gcccctccgc ccgagtcgcc gcataagcgg  10200
aacctgtact atttctccta cccgctgttt gtaggcttcg cgctgctgcg tttggtcgcc  10260
ttccacctgg ggctcctctt cgtgtggctc tgccagcgct ctcccgcgc cctcatggca   10320 gccaagagga gctccggggc cgcgccagca cctgcctcgg cctcggcccc ggcgccggtg  10380
ccgggcggca aggccgagcg cgtccgagtc ttccacaaac aggccttcga gtacatctcc  10440
attgccctgc gcatcgatga ggatgagaaa ggtaactagg gggctggggg aggggcggc   10500 ggcgccggga agaaggcggt ggggtcgccg ggggagggca acacctgcgt ccctttctg   10560 cgggagggga cggtgcaccc ccggaattga tatgccccgg gagactgctt tcccgtaggt  10620
cggagcctca tcttctagta ttcttaaaac ctctccccct tcaggcact gtagctgtcg   10680 actttgtttc agacaccagc cttcccccac acttctgcat gacccaggtc actatgagac  10740
acccagacgt gttgatgaca gtgacatttg tcctagagtg accacactga tcctttctag  10800
cactgtgaag agtgtgcagc ttcctctgaa ccaaggtttc caaaggtttt tgatattgaa  10860
gaagcagtgc cgccttactg gcttttaatg aaagcagagt attgtagtgt cagaaaaaaa  10920
gaacaaatgg tgacaatttt gaaagaaata gctgcatatg actgcagttg aatttgcatc  10980
attttaatca agataatcat tttatcagta caacgattcc tgaatacttt ttcaatgaag  11040
ttatatttag cataaaactt ttccccctgt tgctttgatt ttaattaaaa cagtattcca  11100
aagtagcctt taatttccaa gttgaaatgt ttgatgaatg gattgcgtaa acttaaacat  11160
accactttac agtaaaacct aaaacaacta tgtatgtttc tgaatgaaag caaggatact  11220
acatctttcg ggtttctttt aagctaactt ttttttttt ttgagacgga atctcgccct   11280
gtcgcccaag ctggagtgca atggtgcagt ctcggctcac tgcaacctcc gactccctgg  11340
ttccagcgat tctcctgcct cagcctcccg agtagctggg attacaggca cgcaccacca  11400
cgcctggcta atttttgtat ttttagtaga gtagggattt caccatgttg gccaggatgg  11460
tctccatctc ctgacctcgt gatcgggtcg cctcggcctc ccaaagtgct ggtaatacag  11520
gcatgagcca ccgcgcctgg ccttaagcta acatttttta ttatatgtgc caggcattgt  11580
```

```
gctattagct ttgcatgtgt tatcttttttt cttttttaaaa aaaatagcaa ccatcccaga    11640
ccatgaaaag tgttatttaa tcctcacaat aactttgtga gatgaaggta ttattggtat    11700
cagcatttta gagatgaaga aaatgaggcc caaaagataa aggaggttat tccaaacctg    11760
tgctaataat gaaatttctt ttatggaaaa taagtgaaat taggagaagt ctaacttttta   11820 caattctccc cttttatcct tacttccagt atgctgagat cttgcttctc cctctgccaa    11880
aaacacccac ttttctacca cacctcaatt agatactcac ttgcattgtc cattagtgaa    11940
aacagaaaca atctgcactt cattcatagt gtctgtctct actgccaact ccaaaaactg    12000
ttctagaatt tcaatcttgt tgaaacctgt ttcctttgtg gggcctggga gtgggaagtg    12060
ggatataagg aaagaggcag ttattcattg ttttggacag taaggaaaga gtgacggtta    12120
agagaggtca aggaggtgt taacatttaa gaatactatg tgtttgtaga aggaaatttt      12180
ttgttaactg ctccattctt tttttttttt tttttgaga tggagtctcc ctgtgtcacc     12240
cagactggag tgcagtggcg tgatctcagc ttactgcaac ctctgcctcc cagacgcagg    12300
cgattctctt gcctcagtct cccgagtagc tggaaccaca ggtgcgccct atcacggctg    12360
gctaattttt tgtatttta gtagagatgg tgtttcacca tgttggccag actggtcacg     12420
aactcctgac ctcaggtgat tcgcctgcct cgaccttcca agtgcttgga ttacaggtgt    12480
cagccactgt gcccacccag caagctccat tctttatcac ctcttaagaa catccaggat    12540
cccttgggga gaattaaaac ggttgcaaag ttttagaata gaggaacatg tttaagcgta    12600
gatcattttt tgggccagtc atggtggctc acgcgtgtaa tcccaacact ttgggaggcc    12660
ggggcgggtg gatcatgagg tcaagagttt gagaccatcc tggccaacat ggtgaaatcc    12720
catctctact aaaaatacaa aaattagctg gcatggtga cacatgcctg tagtcccagc     12780
tactcaggag gctgaggcaa gagaagtgct tgaacctgga aggtggaggt tgcagtgagc    12840
cgagatcgtg ccactacact ccagcctggg cggcagagca agactccgtc ttgaaaaaaa    12900
aaagtaggtc atttttggct gggcacggtg gctcatgcct gtaattccag cactttggga    12960
ggctgaggtg ggtggattgc ttgagcccag gagtttgaga ccagcctggg caacatagtg    13020
aaaccctgtc tttgtgaaaa atacaaagat tagctaggcg cagtggcaaa tgcctgtagt    13080
cccagctact tggggggctg aggtaggagg atcacttgag ctcaggttgt tcaggctgca    13140
atgagctgag atcgtgcaac tgcactccga actgggtgac aggagtaaaa ctgtctcaaa    13200 aaaaaaaaa aaaaaaacca aaaaaaaaaa aactgttttta attgttttat ttaggaagag   13260
aaagtcagaa catgcaagga aattttttttt atttgtttat ttttgagacg gagtctcgct   13320
cagttgccca ggctggagtg caatggtatg atcttggctc actgcaacct ctgcctcccg    13380
gattcaagcg attctcctgc ctcagcctcc tgagcagctg ggattacagg tgtatgccac    13440
cacgcccagc taattttttgt gtttttagta gagatgggt tccaccatgt tggccaggct    13500
ggtttcgagc tcctgacctc aagtgaaccg ccctccttgg cctcccaaag tgctgggatt    13560
acaggtgtga gccgcggtga ccgaccacaa ggaaattta gttaacactg ttggttgatg     13620
ggagttggga ggtaggataa aaggagaaat taaggaaaac ctaggcatga aaataaaag     13680 acctgagct cttagatttg aagaaatagc agttccatgt gaggaataag tggaagaaat     13740
agaattcaga cctcaggtct caggctggtg acttaaatct ttcagtatca catatatgaa    13800
tatatctatt atacttaaat cctcctaaac attttttattt ttcagttgga tatattaaat   13860
atataaaaat aattatttaa tttatttag agacagtgtt tcactctctt acccaagctg     13920
gagtggaatg tgatcatagc tcactgcagc ctcaaggctc attcctaggc ttaagtgatc    13980
```

```
ctctttttttt tttttttgct agagatagga tcttgttatg ttagccaggc tggagaaatt   14040
tcaacaatat tttgaacaat aaaaaaaaaa taaattaggt tttattgtaa agtggtatgt   14100
ttaagtttac gccattctcc tgcgtaatgc atatttcata ctcttcctac tgataatgtt   14160
tctgttcaca acttttttctt tatattttga tttcttttct cttttctttt tttttttttt   14220
tgagacagag cctcgctttg tcgcccaggc tagagtgcag tggcgcgatc tcggctcact   14280
gctagctccg cctcccgggt tcacgccatt ctcctgcctc agcttcccga gtagctggga   14340
ctacaggcgc ccgccaccat gcccagctaa ttttttgtat ttttagtaga cgggggttt   14400 cactgtgtta gccaggatgg tctcgatctc ctgacctcgt gatccacccg cctcggcctc   14460
ccaaagtgct gggattacag gcgtgagcca ccgcgcccgg cacatatttt gatttctaat   14520
gtggacatca gaatgggctg ttgacagctc tttttttttt ttttgaggca gagtctcgct   14580
tcttcaccca ggctggagtg caatggcgcg atctcagctc actgcaacct ccacctccca   14640
ggttcaagcg attctcctgc ctcagcctcc ccagtaactg ggattacagg catgtgccac   14700
cccacaccca gccaattttt gtattttttag tagagacagc atttcaccat gttggccagg   14760
ctgttctcga actcctggcc tcaagtgatc cactcgcctt ggcctcacaa actgctagga   14820
ttacaggtgt gagccaccgt gcccagcctt gacaggtctt tagtttgatt ttagttcaac   14880
aactgatgcc gtaatatgcc aaattaaatt agttcagact gaaacggatt acttaaagat   14940
tcattttcct ttaaaaatga agtaaaactt tagccggatg tggtggcggg tgtgtgtaat   15000
cccagctact cgggagggtg aggcaggaga atcgcttgaa cccaggaggt ggaggttgca   15060
gtgagctgag atctcaccca ttgcactcct gcctgggtga aagagtgag actccatcaa   15120 aaaaaaaaaa aaaggctggg catggtggct caagccgggt gcagtgggcc atgcctgtta   15180
tcccagcact tgggaggca gaggcaggcg gatcacttgt agtcagaagt cgcgaccag   15240 cctggccaac atattagtga aacccgtct ctactaaaa tacaaaaatt agctgggcat   15300
agtggtgcac gcctgtagtc ccgggtactt gggacgctga cgcaggacaa ttgcttgaac   15360
tccagaggtg gagattgcgg tgggccaaga tcacgccact gcacgccagc ctgggcaaca   15420
gagcaagact ccatctctca aaaaaaaaaa aaaagaaaa ctgagtttat attgttatgg   15480
ttcttatcta tcttaaattt tttcttagg agattgaata ttttttgtact ttagtcttaa   15540 tccagtggtt gaaagagagt gcacttttga agtctgcctc ttggctgtcc ttgacaacac   15600
aaaccttagt tccaagagaa tgtaattctt cctctttctc agtgcttcaa aatatatatg   15660
atcaaataga aacgagttga ataggcagtc tcttcaaagg tttcctaact ctgtggttaa   15720
ctatcaagga gctggtaata tcatgcactg ccattccctt ggcaacatga cttatctttt   15780
tttttttttt ttcttttttg agacagagtc ttgctctgtc acccaggctg gagtgcagtg   15840
gcgagatctc agctcgctgc aagccccgcc tcccacgttc acgccatttt cctgcctcag   15900
cctcccaagt agctgggact acaggcgcct gccatcacac ctggctaatt tttttttgtat   15960 tttttagtag agacggggtt tcaccgtgtt agccagtacg gtctcgatct cctgtcctcg   16020
tgatccgccc accttggcct cccaaagtgt tgggattaca ggtgtgagcc actgcgcctg   16080
gcctacttat cttctaattt aactgaaaac caatttattt gattcagtga aatggcatca   16140
aactgtagta gtgttaattg aaatatttgg taccttgaaa tgttaaatgc caaattaaat   16200
ctcattttaa tgaaatctcg tgtaaatgtg ttttatatgg tgactatgtt tattctgaat   16260
tttattctta tggcatacta aaaaaaaaaa aaattttttt ttttttttgt aatggagtct   16320
```

-continued

```
tgctctgtca cccacgctgg agtgcagtgg cgcaatctcg gttcactgta acctccacct    16380
cccgggttca agcgattctc ctgcctcagt ctcccgagta gctggtacta caggcgtgca    16440
ccactatgcc tggctaatat ttttgtattt ttaggagaga cagggtttca ccatgttggt    16500
caggctgatc tcgaactcct gacctgaagt gatccgcctg cctcagcctc ccaaagtgct    16560
gggattacag gtatgaccca ctgcacccaa cccatactca aatttgacac tgaattttca    16620
taaaggcctt aatttatctg aaaccaaact atttcaaaag aggaatagca cagcaaattc    16680
tgttgactta atgagaggat atgtgaagtc tatttattaa agcaaatatt aattggaggc    16740
cagttaattt gtacagctct gcattttaga tatttgagaa atatttattt cctctccagt    16800
gagatgtgtt aaaacattag ttatgtgatt aacaaatatg tgtacatacg tatatatgta    16860
catacacatt ttgagacagg gccttggtct gttgttcagg ctggagtgca atgacaccat    16920
cttagctcat tgaagcttca gcctcgcagg ctcaatcgat ccacccacct cagcctccct    16980
agtagctggg tctacagaca tataccacca tgcttggctg atttttaat tttttgtaga    17040 gatggtgatc ttgccctgtt gactaagttg gtaaatattt taattgttga actttcttgg    17100
aagactgaaa acctgtgata gccatttat ataaggagaa gctgaagttc aaagagtaga    17160
ctcatagcag aaacaaaaat agaatttaag tgaatggact caaaatattg tacttttac    17220 tttatactgc aggttttat gttgtaatgc tggtaatgag ctccttggaa tatttggagg    17280
aaaagagaag gttgtaataa tggttctttg gatttactag aacatatcat gttctgcatg    17340
gctcctgtgg gtagacaagc cggaaatctc ctgggtaaca caatggtgga ggttctctag    17400
gtgacgtttg atttctcaag tacataggac taaacagaaa aggcctagta tgttatatga    17460
atgagagatc aagtttctca ggatattcta gggctaaagg atcaggcatc gaagacagaa    17520
attgtctaaa taaaatttt tctattcata gttttaaagg gctaaagggt caggcattga    17580
agacagaaat tgtctaagta aaatattttt ctgttcatag ttttaagctg tgtatatgtg    17640
catgtgtgta tttaaaataa cttcgtcaat gaaaagagtc aaactctgta aaatatttga    17700
agagatttat tctgagccaa atatgagtga ccagtggccc atgacacagc cccagtagat    17760
actaagaaca tctgtccaag gtggtcaggc tatagcttga ttttatacac tttagggaga    17820
cataagacgt cagttaaaca tgtaagatgt acattggttc catctggaaa ggcaggaaaa    17880
ctagaagttg gggaggcttc caggtcgtag gcagattcaa agattttctg attggcaatt    17940
ggtcaaaaga gcttatctaa agtcctggaa tccatagaag gggtgtctg gtttaaaata    18000 ataggttgta gctaccaagg ttttttattgt acagatgaag cctccaggta gcaggcttca    18060
gagagaatac attgtaaatg tttcttatga gactttaaaa ggtggcagac tcttaagtta    18120
attttctcct ggttcaggta aaagacttgg aaagggaaag gattctctac agaacgtaaa    18180
ttttccccac aagagaaagc tttgcagggc catttcagaa tatgtcaaag aaatataatt    18240
tagggtaaaa tacttcaatt tgttttattt atttatttat tttttgagac agagtctcgc    18300
tctgttgccc aggctggagt gcagtggcat gatctcggct cactgcaagc tccgcctcct    18360
gtgttcacgc cgttctcctg cctcagcctc ctgagtagct gggactacag gcgctggcca    18420
ccatgcccag ctatttttt tgtatttta gtagagacgg gatttcacca tgttggccag    18480
gatggtctcg atctcttgac ctcgtgattc acccgcctcg gcctcccaaa gtgctgggat    18540
tacaggcgtg agccactgtg cccggcctca aaatacttca atttctttca tggcctgcta    18600
tctgacgtga tgctgtacta gagtcaggct gggaatttgg cgtcttattg ctacaaaaca    18660
tcttaatatc tctgttttaa tgttaatgct gatcagttgt ccctgaattc caaagggaag    18720
```

-continued

```
agggtatatg agtcatgtcc aaccccccact tctcattatg gcctgaacta gttttttagg    18780
ttaactttgg aatgcctttg gcaaggggag ggtccatgag tcagttgggg gtcttagagt    18840 tttattttt  gcttaccggt ttataaaaag ttaatgaaaa ttatcatatt tcataattct    18900
atataattca atattgtact ttatttaaaa ctcacgtata aaatagctgt ccatatctgt    18960
tttcagaaga tgaggatgga gggtagaaat cagaagtgtc agatttggta attttcttac    19020
actgctgaaa acctatacct accactttga aaggattaat ttcagacttg ctttctttgg    19080
gcctaatgat tctactttga agtttctctg attaaactaa ggaataaaatc tgataaatgg    19140 acattcagat gataccatac ttttccaaaa gataacattg cttttgatta catatgcaat    19200
aaacatttca cattttttct caagattatt tactggcatc tgcaccaaag acacaaaaaa    19260
gcagccactg ttaaggactt tatcccttgt tctgttttta gctggtttgt tgttgtattt    19320
ttcctcatgt tgaatacagt taaaccctat taaactggat tccccatatt actgttagtt    19380
gtcctgatga caattaagga tagttagtaa atggatattg aatcatttta tttttttagt    19440
agtgatggcg tttcgctgtg ttggccaggt tggtctcgaa ctcctggcct caagtgatct    19500
gcctgtgttg gcccctcaaa gtgttaggat tacaggcgtg agccactgca cctggctgga    19560
tattgaatta ttgaagaagg atgttcccta acacttcctg cctctttttcc gctgtcttac    19620 tctctctgtt ccacccagta gtagttgggt ttttgatgtc tggcaaagta tagattgtct    19680
actcttctat attagttttc ttcactcttt tttttaaaaa tgttttaaa gcaagataga    19740 gacagggtct tgccgtattg cccaggctgg tcttgaactc ctgagctcaa gcaatcctcc    19800
cacctcaccc cataaagtgc ggagattaca ggcatgagcc accatgcctg gccagttttc    19860
ttcactcttg acctataata gtcctgcaaa gccagtgaag ctgttaatat gctgacgtag    19920
cctttttttc tctcgtttgt gaattattaa caatcgctga tcttacacat catatacaat    19980
aaaacatctt tgaacactgt cacatctcag cagctcattc tggttaatga ggaaagaaaa    20040
atgtcaaaat ctgtgatttt cttagaggtt attaaatgtt ttacagctat gtagatattc    20100
tgtagacttg ctgtacttac ttacataact tttctgctct tctgcagagg gagagaatta    20160
acttcataag tgggctttgt caatgccctc cagtcagcga tctccaggaa caaacttatc    20220
tatggttgag caagtggggt ttattaccca ctgtagccag ggagaacaca catatgtaat    20280
aaccatggta tgtcatagta aagggtgtta ggaagatagg atttgggctc gtttatttgg    20340
tgattttaag gagggtttaa agaagcaggg ttttgctctg atttggatgc taccaggagc    20400
tgcgaataat tctatgaata aatatcataa aacctatcta gaagaaaaga ctagagtgag    20460
gtctaaagct gtagtagtta aaaagcaaag gtcactcctt atctggaaaa ggggaatatt    20520
tggtatttca tggtttagac agtgttcagt gttcatgttt tgcctgtgtt tagacataat    20580
tgtagagtgg tcttgttcca ccgtggtcac agagtggcat tatttcatgc tgatattctg    20640
taagtgccag gtcaaatacc aaggtttagc tgatagtagt aggccagctc ctggatgtaa    20700
taagctgttt ttctctttct cagctttttt ttttgttgtt tttttttaa aatagagtct    20760 ggctctgtca cccaggctgg agttcagtgg gggcaatctc agctcactgc agcctctgcc    20820
tcctggattc aagcgactct cctgcctcag cctcccaact agctggaatt acaggcgcaa    20880
gtcaccacac ccggctaatt tttgtatttt tagtagagac ggggtttcac catgttgagc    20940
aggctggtct cgaactccgg acctcaagca atccatctgc ctcagcctcc caaagtgctg    21000
agattacagg catgagtcac tgcacctggc ctgtttctta gatttgaggg tcaacttta    21060
```

```
cccttttcga actgtggggc ttcttatgga aattgacatt taagtcctga ccatatagga      21120
tcttgggcaa gttacttaac tatgtatgct gagatgtttt tttaaatgct tagtgcttgc      21180
acataatagg tactcagtaa atgagaacta ttattataaa atcaatagta cttttaagat      21240
tacagctaga ggttatgtta gaacattgtt aactcttcgt actagtttct gttacacttt      21300
ttaggatgca gtagcagcat aaacgagata tggggaagaa cgagaggtat ttaaacagtg      21360
atataggccg ggcgtggtgg ctcacgcttg taatcccagc actttgggag gctgaggtgg      21420
gcagattacg aggtcaggag attgagacca tcctggctaa cacggtgaaa ccccatctct      21480
actaaaaata caaaaacaaa attagccggg cgtggtagtg ggcgcctgta atcccagcta      21540
tttgggaggc tgaggcagga gagtggcgag aacccaggag acagagcttg cagtgagccg      21600
agatcgcgcc actgcacccc agcctgggcc acagagcgag actctgtctc aaaaaaaaaa      21660
aaaaaaaaaa attaaaacaa aaatatttgt gttaattgtg atgacaaaaa aaaaaaaaga      21720
gatgaagtc  tctccctaac ctcactcctc atttagtgtc atggcttttt tcttttttt       21780
ttttttttt  ttgagacaaa gcctcactct gtcacccagg ctggactgca gtggtgcaat      21840
ctcagctcac tgcaggctct gcctcccaga ttcaagcaat tctcctgcct cagcctcaca      21900
agtagatggg actacaggca catggcacca tgcccagcta atttttttgtg tagttttag      21960
tagagacagg gtttcactat gttggccagg ctggtctcga actcctgagc tcaagtgatc      22020
cccctcctt  ggcctcccaa agtgctggga ttacaggcgt gagccctgct cccagactcc      22080
tggctttttt ttttttttt  aatgaaaaat tcaaatgct  cttttttttt tttttttttt      22140
tttgagacag agtctcgctc tgtcgcccag gctgaagtgc agtggtgtga tctcggctca      22200
ctgcaacctc tgcctcccag gttgaagtga ttctcctgcc tcagcctctc gaacagctga      22260
gattacaggt acgcgccacc acgcctggct aattttttgta ttttttaatag agatgggggtt    22320
ttgtcatgtt gtccaggcta gccttgaact cctcgcctcg tgtgatccac ctgccttggc      22380
ctcccaaagt gctaggatta taggcgtgag tcgctgcacc tggccacaga aattttttga      22440
agaagataaa taaggtgaca ttttttaaggg tcaaagaaaa tgtcaaaaac tagaatgatg     22500
tctttacata gggtttaaaa cttttccaaat taacagggaa aataattctt taccttgaaa     22560
ataaatgttt gctagtgaaa gcaaatacaa tcttttttact aaatgtttta ttaaattttt    22620
ttttcttgta gacacagggt cctactgtat tacccaggct ggtcttgaat gcctggcctc      22680
aagcaatcct cctacctcag tcttccaaag tgctgggact acagacatga gccatcacac      22740
tgggtctttt ttaccaaatt atagtagaaa gcacttttttc tctaatggtg aactatgaga    22800
gaattaatca ggggctatta gtaattcatc cctgaattaa tcagtgatta taatgctttg      22860
tggtccatgt agtttgctgg ggattaacac accatgaaag tctaccagga gattttttttt    22920
tttcttgag  aacagggggcc ataatcagta gtccttaaat gaaatggact attcccattt      22980
cattatatgt tgcctaggct ggactcgagc tccttggctt aagtgatctt cccacttcag      23040
actctcaagc agctgggact ataggtgtgt gccaccatac ctggcttaat tgagtgtttg      23100
ttttttgttt tttttttctga gacagagtct cgttgtgtcg cccaggctag agtgcagtgg    23160
cacaatctcg gctcactgca acctctgttt cccaggttca aacgattctc ctgcctcagc      23220
ctcccaagta gctgggatta caggcgcctg ccaccatgcc tggctaattt ttgtattttt      23280
agtagagatg gggtttcacc atcttggcca ggctgatctc gaactcttga cctcatgatc      23340
cacacacctt ggcctcccaa agtgctggga ttataggcgt gagccaccgc gcccggcttt      23400
aattgagatt tttagatatc tattactctg ctaatttttgt cacttgcaag ttgccatcag     23460
```

```
aaaattgtag gaaaatggat atatttgttc cttggaatgg tttgtgtgag aatacttaag   23520
gattaaatag ataagtaaaa ctggtgggct ttatataaca tagatgagca aatgtcagga   23580
acatacaact gtgcacacag ttcaggagaa ggaggattta agttaatcaa caaatttact   23640
aagtataata aagatactaa aagtagtgtt tccataccac tttattactt aaagtatcat   23700 catatacect atttatatg attttgcca caagtcagag ttaggtaaaa gaaatacttg    23760
cttttcaggt aaggagtttg acgcccagac agattaactg acttttccaa aatcatattg   23820
ctattaaatg gtggaacaag gacttaaatc tttgccttct aactcacata cttgcaaaca   23880
catatcctct cactctaccc caagctaccc atgttttgac ccttcttgtg gcaatctggg   23940
tctcactaat atttgaaaga aaacgtacag tagataattt gcaagttaat ctgttacgca   24000
tatctcttac ctctatttaa agatgaatat cagcatttct gttgtttcta cagtaacata   24060
ctaaaaaata atgcagtcca ggtgcagtgg ctcacgcgtg taatcctagc acttttggaa   24120
gttgaggcag gaggatcact tgaagccagg agttcgagac tagcctgggt atgcaagacc   24180
ccatttctgt tttttttttt tgtttgtttt gttttgtttt gttttgtttt tttgagacgg   24240
agtctcgctc tgtcgcccag gctggagtgc agtggcggga tctcggctca ctgcaagctc   24300
cgcctcccgg gttcacgcca ttctcctgcc tcagcctccc aagtagctgg gactacaggc   24360
gcccgccact acgcccggct aattttttgt attttttagta gagacggggt ttcaccgttt   24420
tagccgggat ggtctcgatc tcctgacctc gtgatcccca tttcttttc  actgcaacct   24480 ttgcctccca ggttcaagtg attgtcgtgc ctcagcctcc caagtagctt gggattacag   24540
gcatgtgcca ccatgcctgg ctaattttg tattttttgg tagagatgga gtttctggcc   24600
aagctggcca ggctggtctc gaacgcctag cctcaagtga tctaccctcc ttagcctccc   24660
aaagtgctgg gattacaggt gtgagccact gtgcccggcc ccatttctac aacaattaaa   24720
aaatattagc ccagtgtagt ggtgcatgtc tctagtccca gctactcaga aggctgaagt   24780
gaaaggattg cttgagccca gaatttcaag gctacagtga gctatgataa tggcattgca   24840
ctccagcttg ggtgacagag tgagaccctg tctctaaaaa atgaagtaaa atagtgcaca   24900
agtatagaac ttgaaaatct tccttaacct taccataagg gaaatgatta ctaataagtt   24960
tcttaacttt ttgtacttac ataaacataa atattcatca gagaaaaaaa tatgcaaaac   25020
aatttgcaat cttttcact taccatattt tggaattttt ttcatttcaa tatatttgat    25080
cttccttgtg tttttcagt ttgtttgttt ttgtcaccca ggttggagtg aagtggtaag    25140
aacatggctt attgcagcct caatctcctg ctcccattca gccctcaag tagctgggac     25200 tacaggtaca tgtcaccacg cccggctaat ttttattttt attttggtag agatgggtt    25260 tcaccatgtt gcccaggctg atcttgaatt cctgggctca agtgacccgc ccacctcagc   25320
ctcccgaagt gttgagagaa caggtgtgaa ccaccatgct ccacctctta gtctttacaa   25380
tctgcaaaac ctcataagtg gctaatagag gaatatagta aagcaaaggg ggatatcact   25440
gattagaact gtgtttttag gctgggtgcg gtggctcacg cctgtaatcg caacattttg   25500
ggaggctaag tgggagtatc acttgagccc gggagttcaa gaccagcctg gcaatatag    25560 tgagagaccc tgtctttaga aaaaattaa ccaggtgtgg tggtgcacac ctgtggtccc    25620
agctattcaa gaggctgagg tgggagaatc gcttaagcct aggaggcgga ggttgcagtg   25680
agatcatacc actgctctct agcatgggtg acagagcgag acccagtcta aaaaaaaaag   25740 tatttttcg tttttttcca actcatgtac acccgccacc ccaccctgc ttttttttt     25800
```

```
tctgacattg ggtcttgctc tgtcacccag gctagagtgc agtagcacaa tcaactcact    25860
gcagcctcct cttcctggac tcaagcagtc ctaccacctc agcctcccaa gtagctggga    25920
ccacaggtgt gcaccatcat gcctggctaa ttttttgtact ttttgtagag atagggtttc   25980
accatgtggt tcaccatctc taactcctgg gctcagtcag tccacttttg cctcggcatg    26040
agccactgtg tgcagcccac gttttttatt aatggatatt tggattgttt ccatctattg    26100
tgaataatgt ggctatgaac attggtctaa atatctgttt aagtcccggc tttcaatact    26160
tttggatata tacctaggag tagaattact gaattatatg gtaactttct gtttaaattt    26220
ttgaactgcc aacctgtttt ccatagggc tgcaccattt tgcattccca ccagcagtgt    26280
acaagggttc cagtttctcc acatttgtta tttttcattt tttaaaataa tagtcatcct    26340
aaagggtatg aagtggtatc tcgttgtgat tttgatttgc atgtattttt ctaatgactt    26400
atgatgctca gcattttgtc atgtacttat gtaccatttg tgtatcttct ttggaaaaat    26460
gtctattaat gttcttttcc catttttttaa ttgggttgtt tttatgttta tcaatttgt    26520 aaacatttta agctctgcag cataactact caaccctgtc acatggtaag attgacccag    26580
taaaacttta tgtacaaaaa taggcagctt actagattta atcttagtcc atagtttgct    26640
aaggcatgca ttagataatg tagttacact attggctaat aatttaaact acaagtggtt    26700
gtaagtttct gccacccaaa ttctttcttg atttgatgta gtctggttgg ttgaatttga    26760
gtgttatatg gggtcataga gttaaaagag aaatgtctat gagaaactag ggactgttgg    26820
gagctaatgt taaaggattt tggaggcctt ttgtgcactg gagaccattg gaagattgga    26880
ttttctgcta taaatgtatc taaaggataa tcagtgtaag ttatgggctg tagtttgcca    26940 accctacat taagggattg aaataatttg aatatgggtt tcagttcttg tatggtctgg    27000
ctcagttctt tttttttttt tttttttttt tttttttttg agatggagtc tcactctgtt    27060
gcccaagctg cagtgccatg gcacgatctc agctcgctgc aacctccgcc tcctggcttc    27120
aagtgattct cctgcctcag cctccagagt agctaggact acaggcacgt gccaccacat    27180
ctggctaatt tttttttttt tcaagacaga gtttcgctct tgtcacccag cctggagtgc    27240
aatggcacga tcttggctca ccgcagcctc cgcctcctgg gttcaagtga ttctcctgcc    27300
tcagcctccc aaatagctga ggcaacaggc gtgcgccacc acgcctagct aattttttctg    27360 tttttagtag agatgggggtt tcaccatctt ggccaggctg gtctcgaact cctgatctca    27420
tgatccaccc gcctcagcct cccaaagtgc tgggattaca ggcgtgagcc acctcacctg    27480
gcgttttttt gtgtgtgttt tcagtagaga tggggcttca ctgtattagc cagaatggtc    27540
ttgatctcct gacctcgtga ttcacctgcc tcagcctccc aaagtgctgg aattataggc    27600
atgagccacc acgcctggct gtggctcagt tcttaactgt tcattcattc agggtcccag    27660
ccaaaatctt ttgccacagc ttctcctggg catgctctga aattcatttt ttgtctgttt    27720
agttgcatga gtccactgaa agctttgctt attttctcca ccactttcag agttcacagt    27780
cacttcaagt agacgaggtc aggagatcga gaccatcctg gccaacatgg tgaaacccccg   27840 tctctactaa aaatacaaaa cttagctggg cgtggtagcg tgtgcctgta gtcccagcta    27900
ctcaggaggc tgaggcagga aaattgcttg aacccgagag gcagaggttg cagtaagccg    27960
agatcatacc atttcactcc agcctgggcg acagagtgag acactgtcaa aaaaaaaaa    28020 aaaaaaaaa aggaaagaaa agtgctccaa atgctgggct catctctgct ggcttctctc    28080
ctttttatat ttcgataatt tttaaaataa taaccatcct aatgggcttg atatggtccc    28140 tccttcta attttggtaa ttttcattgt tttggaaact cactaatccc ttcaaacaga    28200
```

-continued

```
tgttttaaa acttttttc tagttctctc tcttttttt tttttttttt tttttgagac    28260
agggtctctc tcagtggtgc gacctccctt actgcaacct ctcctcctg ggttcaagca    28320 gcgattctcc tgcctcagcc tcccaaatag ctgggagtac aggcacccac ccccacgccc    28380
agctaatgtt tgtatttta gtagagattg gtttcatca tgttggccag gctggtctcg    28440
aactcctgac cccaggtgat ccgcctgcct cagccttcca aagtgctggg attacagcca    28500
tgagccaccg cacctggctc tagttctctt ctaatcttac tatagtaatc aaaattttag    28560
tgctgatgtt ataatccaag cccaaatgga tattcttata cattaaatgt tggaatatca    28620
tgtttgttaa aaatcagatc tgctgggcac ggtggctcaa tgcctgttat cccagcactt    28680
tgggaggccg aggcaggtgg atccctgag atcaggagtt cgagaccagc ctgaccaaca    28740
tggagaaact ccgtctctac taaaaataca aaattagccg ggcgtggtgg cacgtgcctt    28800
tcatcccagc tactgggag gctgaggcag aagaattgct tgaacctgtg aggcggaggt    28860
tccagggagc tgagatcgtg ccattgtact ccagcctggg caacaagagc gaaattccat    28920
ctcaaaaaaa aaaatcaga tctgtcccta tggttttatc ttcactgcat gtcatatata    28980
aatggaagca tgtagtatgt agccttttgt gtctcgcttc tctcccttg cataatattt    29040 ttgagattta tcccttttcc tacatatgtc agtagtttgt ttcttttaa tgctgaatag    29100 tattccacgt gtggagatac cacaatttgt tactccattc actaaatgat ttgggttgtt    29160
tcctgttttt gttattgttg tgttgttgt ttaattaatt aattaatttt ttttttgaga    29220
tggagtcttg ctctgttgcc caggctagag tgcagtggcg caatcacagc tcactgcaac    29280
ctctgcctcc ccggttcaag tgattctcct gcctcagcct cccaagtagc tgtgattaca    29340
ggtgcccgcc accacaacca gctaattttt gtatttttag tagagatggg atttcaccat    29400
gttggccagg ctggtcttga actcttccct ccttggtctc ccaaaatgct gggattacag    29460
gtgtgagcca ccatgcccat cctcctgttt ttaaatttta tgaataaagg tactgtaaat    29520
tcatgtacag gtcttagaag tttgcatttt tcttgggtaa atatgtagaa gaagagattg    29580
ttgactcatg tggtaaatat atgtttaatg tcataagaaa ctaccaaact gttttttccaa    29640 ctgggtgcca ttttgtttcc taccagcaaa cataatgaaa ggtccattac cctttgtctc    29700
gtaatatttt ggtatttta tgttcttttg tttttttgcc attcaaaatt gggtgcattg    29760
ttgtatcttt ggattttaat ttgtacttcc ctaacaacta atgatgtgga gcatcttttt    29820
atacgcttac ttgccaatta tgtcttaatt cttttggcaat acttatattt gactctgcct    29880
actatatata tatatatata tatttttatg ctatatatag agtatatata tttttatact    29940
atatatattt atatatacta tatatattta tatatactat atatatatat atatatatat    30000
atattttttt tttttttga gatgaagtca tgctctgttg accaggctgg atgcagtggc    30060
atgatcttgg cttaccgcaa cctcaacctc tgcctcccag gttcaagtga ttctcctgcc    30120
tcagcttcct gagtagctgg gactacagac acatgccacc atgcccggct aattttgta    30180 tttttagtag aggtggagtt tcgccatgtt gtccaggctg tcttcaact cctgacctca    30240 ggtgatccac ccgcttcagc ctcccaaaag tgctgggatt acaggcatga cccaccgtgc    30300
ccagctggaa taagcaatct taaaaagcag tttgttgatt tctggtgaat agagaaaatg    30360
tgacaaacta tgactcaata gtttcatttc ttttttgttt gtttgtttgt ttttttgaga    30420
cagagtcttg ctctgtcacc caggctggcg tgcagtggct cactgcaagc tctgcttcct    30480
gggttcacgc cattctcctg cctcagcctc cggagtagct gggactacag gcgcccgcca    30540
```

```
ccatgcctgg ctaatttgtt ttttgtattt ttagtagaga cagggtttca ctgtgttagc    30600
caggatggtc tcgatctcct gacctcgtga tccacccgtc tcggcctccc aaagtgctgg    30660
gattacaggc atgagccacc gcccctggcc tactttattt tcttaagcat atatcttaaa    30720
gaaactgcag gtatgcatta ggggacaggt agaaaaatgt tacagcattg tttgaaatgt    30780
tgaaaaactg gaaacaacct caatatctta ataatagaaa aaatggttga ggctggctgt    30840
ggtggttcat gcctgtaatc ctagcacttt tggaggctga ggcgggcgga tcacctgagg    30900
tcgggagttt gagtccagcc tggccaacat ggtgaaaccc cgtctctact aaaaatacaa    30960
aaaattaggc aggtgtggtg gtgcacacct gtaatcccag ctacttggga ggctgaggca    31020
caagaatcac ttgagcctgg gaatggagg ttgtagtgag ccgagatcat gcctactgca     31080
ctccagcctg gcaatagag tgagactccg tctcaaaaaa aaaaaaaaa aaaaaaggg       31140 aaggagcatg ggaatgggaa gaggcactaa aaaggaact tcttttgtat ctgttacatt     31200
gtactcattt tgttttttaaa attttaagcc aaatatgaca ttgttatcac ttttgttgcc   31260
actcagaata caagtgctat tacactattt tctataattt tcccttttc aaactaaaaa     31320 acaaaaatac atgtaaacag gtgttttctt tatggaaaac aggaaggtga gcatccaaat    31380
aattttagtt aatttataac aaactcttaa taatttcttt ttcttcttct tctttttttt    31440 ttttttttt tgagtcaggg tcttgctctt ttgctcaggt tagagtgcaa tggtacaatc     31500
tggtacaatc acatcttagt gcaacttcta cctcttcagc tcaagtgacc tctctcctca    31560
gtcccccaag tagatgggac cacagatgtg tatccccaat catggttaat ttttaaattt    31620
tttggtagag ataaaatctc accatgttgc ccaagctggg cttgagctcc tgggctcaag    31680
cagtcctcct gccttggcct cccaaagtgc tgggattata ggcgtgagca aactgtgccc    31740
agtcttcata aacttttctt tacatgtcct tatcaagtac ttttgagca cctactgtca    31800 accagccgta gtatataata ctgataattc tataacataa gaaattgacc tgtttaaggg    31860
gatgaatatg gttagttatt ttcagggtga agaaacagaa gaatcgggga ggtagtacat    31920
agtcataagg agacggcatt tcttagtcac tttgtgtggt gtttataata agacttcatg    31980
tggccaggtg cggtggctcg tgagcgcctg taatcccagc actttgggag gccgaggtgg    32040
gaggatcaca caaggtcag gagatcgaga ctatcctgaa caacatggtg aaaccccgtc     32100
tctactaaaa atacaaaaat tagctgggtg tggtggcacg tgcctgtaac cccagctact    32160
cgggaggctg aggcaggaga atcgcttgaa ccagggagtc ggaggttgca gtgaaccaag    32220
atcgtgccac tgcactgcag cctgggctac agagagagac tccatctaaa taataaata    32280 aataaataaa taaatagact tcgtctgttt catcaagagt cattgtatta tattgatttt    32340
gaaatttcaa ataataataa ggaatagtat ggaatttttt gttgattaa atggggacat     32400 gaggccaggt gtggtcactc aggcttgtaa tcccagcact tcgggagacc agggcaggag    32460
gattacttga gcctaggagt tcaagaccag cctgggcaac atggcaagac cctatctcta    32520
caaaagaaat acacaaaaat tagctaagtg tggtggcaca tgcctgtagt cttagctact    32580
cgggaggcca agggaagagg atggatcact tgagcccagg agttggaggg tgcagtgagc    32640
taggattgtg cccctgcact ctagtgtggg tgacagcaag actctgttta aaaaaaaaa    32700 aaatgaggc cgggcgcggt ggctcacctc tgtaatctga gcactttgag aggccaaggc     32760
gggtggatca cctgagttca agatcagcct ggccaacatg gtgaaaccc cgtctttata     32820 cttaaattac aaagattagc tgggtgtgat ggtgcacacc tgtaacccca gctactccag    32880
aggctgagac agcagaatcg cttgaacccg ggaggggag gttgcaatga gccgagattg     32940
```

-continued

```
caccactgca ctccagccta ggtgacagag caagactctg tctcaaaaaa aaagaaaaa    33000 aagtctaaga agttaatttt cattcagaca aatgttcaaa aataatagaa ataaaacaaa    33060
aaattaattt tcaaatatgt gatttgagta taacgatcac tttacagaag ttattctaca    33120 tacttttga ttatgctgag tttttaggtc cttttaaagc ttaacttgta tcaggaatta     33180
atgttttaaa ctagttgttg ggttcaaaga aaatagaaat gtgttattaa atgccacact    33240
tgtaatctca tacagcagtt ctcatgatgc aatcaattgt taaataaaaa cttcctctag    33300
agaggaggta cccagcaatg aacacattat atcagatttg aatatgagat taaacaatgc    33360
tttttgtttc attgttattg aaatcatatt tgtattttc aaaagtatat atacttaaaa     33420
attcctaaat aaaatgtctt tctgtaatac agcattttag gttataagga tcaataccat    33480
gggctgataa gcaaaatagg actcacggcc ccaaaatgtt gataaacatc atgaccatat    33540
tccccataat ggagttacat atacacatta caatgataaa aatactaaga agttatatag    33600
taatgtttct cagacttgtt cacaaccctg tttttatgt attacctctc aaaagcatga    33660
tttgcaatat ttagtgtact cttcatacga tctatacaaa taattttta ttttaaagca    33720 ggacagaagg agcaagctgt ggaatggtat aagaaaggta ttgaagaact ggaaaagga    33780 atagctgtta tagttacagg acaaggtaag attgtatttg tttatagcca tcccaaatta    33840
tgatatattc acatgattgt ccagatttca gatctattta tttatttatt tatttttctt    33900
tctttctttt cttttctttt ctttttttt ttttttttg agacagggtc tttcctctgt      33960
tacccaggct ggagtgcagt gatgtgatca tagctcactg caacctcaaa cttctgggct    34020
caagtgatcc tcctgcctct gcttcccatg tagctgggac cacaggcgca cactaccata    34080
cttagctaat tattattatt attattatta ttattattac tagtttttga gacagagtct    34140
cgctcttttg cccaggctgt agtgcaatgg tgcaatctcg gctcactgca atctccgcct    34200
cccggattca ggctatttat tctcctgcct gagactcctg agtagctggg attacaggtg    34260
catgccaccg tgcccagcta attttttgtat ttttagtgaa gatggggttt tgccacgttg    34320
gccaggctgg tttcgaactc ctgatctcaa gtgatctgcc cacctcagcc tcccaaagtg    34380
gtgggagtac aggcatgagc cactgtgggc cacacttagc taattaaaaa aatttttttt    34440
gtagagacag ggtctcactg tgtttctgtg actgatctta aacttctggc ctcaagtgat    34500
cctcctgcct cagctttcca aagttgtggg attacaggca tgagccactg tacccagcca    34560
gattgtattt atcttaataa atgtatttgg gccaggcaca gtggctcatg cctgtaatcc    34620
cagcactttg ggaggccgag gtgggcgaat cacctgggat caggagttcg agaccagcct    34680
gatcaacatg gagaaaccct gtctctacta aaaattcaaa attagccagg cgtggtgtcg    34740
cgcacctgta attgcagcta cttgggaggc tgaggcagga gaattgcttg gacccaggag    34800
gcggaggttg tggtaagcca agatcgcgcc attgcactcc agcctgggca acaagagtga    34860
aactctgtct cagaaagaaa gaaaagcaaa acagtatttc atttaattaa aaatgccttg    34920
tattatacca gtaagagtaa aaaacaattt aattaaagta tgatatatgc tcttttcatc    34980
acttagaatt tgaattttaa tcttattgaa gaggctgttt tagttttatt tagatatggt    35040
tataacaaca atattaatat ctgtgaccaa attggtgcat gcatgggcaa tgaaaagcta    35100
tgttgtgact gcagcatggt ggatagcatt agtaagttag cattggttgt aaaatgaatc    35160
ccaatttcaa agattttgaa acgtggggaa aaaatatttt agaccccatg aaataagacc    35220
tgaaatctat gaaataccac agtaggttgg aaatcatcat gagaaactgt aactattttt    35280
```

```
ttttataggt attatatgta ttctttgaga cagggtctca ccctgttgcc caggctggaa   35340
tgctgtgatg tggtcacctc tcactgcaac atccacttcc tggggctgaa gtgatccttg   35400
caactcaccc tcccatgctc ggctaatttt tttttttttt tttttaagta gagaccagat   35460
ctctttatgt tgcccaggct ggtcttgaac tcctgggctc aagtgattct gctttgtctg   35520
cccagagtgc tgggattaca gaagtgagcc acaacacctg gcctaaagat agtattttta   35580
aaatttcttc tgttttcttt cttttgggta tacatttttct tcttttttttt aaaaaaaaat   35640
ttctgtataa agactgtgac tccccatgaa agtagtttgg gtgataattt atcgtgaaac   35700
aatattagtt gggaaatgta gatattttaa ttaattttttt tctttcaggt gaacagtgtg   35760
aaagagctag acgccttcaa gctaaaatga tgactaattt ggttatggcc aaggaccgct   35820
tacaacttct aggtatcaat taatgtataa tttgatgtgg gatgtattgg aaatgtgtgt   35880
tcaatgaaac tttaatttgt agaaagaaat agatcagtga ttgaaaatgt ggtccaggct   35940
ttttaacata aagaaaacgt ataacatata caaaaacaga agagcataat ggacttcttt   36000
ttttttttga gatggacgct tgctctgtca cccaggctgg agtgcagtgg cgtgatcttg   36060
gctcactgca agctctacct cccaggttca cgccattctc ctgcctcagc ctcctgagta   36120
gctgggacta caggcacccg ccaccacgcc ccgctaattt ttttgtagtt ttagtagaga   36180
cagggttttca ccatgttagc cagaatggtg tccatctcct gacctcgtga tccacccgcc   36240
tcggcctccc gaagtgctgg agttacaggc gtgagccaac gcgcccagcc gagcataatg   36300
aacttctaat tattcttctc tcagctttga taattatcac ctcactatca gtcttgattt   36360
atttatacca agggctagca aactgcagct gatgggccaa cccagctcac tgcctattac   36420
tataaataag gttttattgg cacacagcca ttcctttcct ttaggtattg tctatggctt   36480
tcatgctacg gtgacagaat tgaatagttg atacagagac aacactgccc tcaaaaccta   36540
acatatttac tgtctggccc tgagaaagcc tgccatcttc acttgacatc ccacttcact   36600
gtcccccaac ttcttattat tttgaaacaa attattgact tattttccat ttataaatat   36660
ttcatattat acctctaaaa gataaggatg tcaaaataaa atcacagaaa taccattatc   36720
acacctaaaa aataactcca aatttctttt aacattatcc aaaaaaactg acccccccaa   36780
aatgcaattt ccaaatttct aattttctca aaatttaata attttttacta ttttttaata   36840
atttgtttgt atcaggatct taaaaagatc cgtatgtctc tttttaatgta caggttcatc   36900
tgttttttcat tttcttccaa tttatttgtt gatgaaacca ggtctttgtc atgtaatatt   36960
tcctacagtc tgacttttgc tgcatgcatc tttttgtggta tgttttaaca tgttcttctt   37020
tcctcccacg ttaaatgata gttggatata gagccttgat cacattgaaa gttgattttt   37080
atttttttaat gattagacta cttcctaggt ggttgtgttt gtgtgttcat cattagttgt   37140
tccatcttgt gaggttagca gcagttaact atgactgatg tccagtgata ctttaattct   37200
gtcattcttt cagcattcat caactgtaat agaaactttt acttgtcttc tgtttgatgg   37260
cgtaggtttt aaatatatat taataagtta aatctaccac tcaaaaaaag tagaacaaaa   37320
cctactacat atgagtggct ctaccatacg ttggtggatg gaaatagtag atatttggta   37380
agcaggtaaa ccttatttat ttgtagccct gtgacttggg gtaagttatt ttgcatgtct   37440
gggtcttttt tatctaattt gtaatatgaa gctattatta ttattattat tattattatt   37500
attattatta ttattattat tattcgagat ggagtcttgc tttgttgccc aggctggagt   37560
gcagtggtgc aatctcggct caatgcaccc tccacctcct gggttcaaac tattctcgtg   37620
attcagtctc ccgagtagct aggattacag gggcctacca ccacacctaa tttttgtatt   37680
```

```
tttagtaggg acggggtttc accatgttgg ccaggctggt ctcaaactcc tgacatcaag   37740
tgatccatcc acctcagcct cccaaagtgc tgggataggc cgggcacggt ggctaacgcc   37800
tgtaatccca gcactttggg aggccgaggc gggtggatca cgaggtcagg agattgagac   37860
catcctggct aacacggtga aaccccgtct ctagtaaaaa aatacaaaaa actagccagg   37920
tgtggtggcg ggcacctgta gtcccagcta cttgggaggc tgaggcagga gaatggcatg   37980
aacccaggag gcggagcttg cagtgagccg agatcatgcc actgcactcc aggctgggca   38040
aaagagcgac actctgtctc aaaaaaataa aataaaataa atagataaat aataataata   38100
aagtgctggg attacaggca tgagccacca cgcccagctg aagctaatat tattagctaa   38160
taataatatc tcatatttt gaccattgaa ttattaaagg aacctaaacc atagtagtaa    38220
gtgctttaaa aatgttggtt tttatttatc tgtttacctg actgtcatca cctcctttgc   38280
ttaggtagaa agatatattc ataaacacat acatatacat tttattcatt ctttaattca   38340
tttactccta tatggtcatt gtgtttgtgg gattttgcc cgcacatagt taaaaatgca    38400
gccgttactg ctttcagatg agtaacaagg tagtgttccc tggcttctgt ggctgacagg   38460
atttgccttc ttcctttcta aatggaggtt attactgtgt cagatataat taaatagtgt   38520
attaaagttt gttgcaataa aataattgat ggttctaatt ggtactttct acgtgtttta   38580
tctttaaagc ttttcagtgt atatataaag tatatatcat acagaataaa tttgattgtg   38640
gagcattttg taacatcttt caaaattaat aagagttggt ttttatgttt tgtttgatgt   38700
tatgatatag gacattagaa gtattaatat caattagaga ctcatctttg aatgtgactt   38760
tgtactttct tatttgtgtt agtagaggag agaacaaaaa gaagatatgt aatgtaatat   38820
gaaactaggc atttaaagat ttaacgtttt ggatatttta aagttggtgt ctgttttcac   38880
cctcaaaaat gctattacct atttatgaaa tatctttaaa agtgtggagt ggtagatggg   38940
aaaggtgaca tcggctgggc gcggtggctc acacctataa tcccagcact ttgggaggcc   39000
aaggtgggcg gatcacctga ggtcaggagt tcacgaccag tctggtaaca tggtgaaacc   39060
taatctctac taaaaataca aaaaattagc caggctggtg gtacgcacct gtaatcccag   39120
ctactcagga ggctgagtca ggaggatggc ttgaacccag aaaatggagg ttgcattgag   39180
ccaagatggc accactgcac tccagactgg gtgacagaga gagactccgt ctcaaaaaaa   39240
aaaaaacgcc gggcactgtg gctcacacct gtaatcctag cactttggga gactgaggcg   39300
agcagatcac ttgaggtcag gagttcgaga ccagctgggt gcctgggcaa catagtgaaa   39360
ccccgtctct actaaaaata caaaaaaatt agccgggcgt agtggcgggc gcctgtagtc   39420
ccagctactt gggaggctga ggaaggagaa tggcgtgaac ccgggaggcg gagcttgcag   39480
tgagccgaga tcccgccact gcactccagc ctgggtgaca gagcgagact ccgtctcaaa   39540 aaaaaaaaa aaaaaaaaaa tagccgggca tggtggcggg cacctctaat ctcacctact   39600
tgggaggttg aggcatgaga attgctcgag cctgggaggc agaggttgca gtaagcagag   39660
accacaccac tgcactctag cctggatgac agagtgagac tttgtctcaa aacaaaaaca   39720
aacaaaccaa accacctctt gtccactcct aatctccctt actgtgtttc acttattttt   39780
ttcccatata tttgtcacct tctaataaac tgtgtaactt attttttatg tttattgtgt   39840
actatctgtc ttctccctgt tggaatataa actctatgga ggagggatcc ttgtctatat   39900
cccaagtgcc tacaacagtg tctagcacat gctagttacc gaataaatat ttgccaagtt   39960
aatgaagttg tttataaccc ttggcactat acctgataca gtgtagggac ttaataaatg   40020
```

```
aatgttaaat gaagctatct taaaaatata tatatatata taacagccag atacgccaat    40080
ttgccgacat caaaattaat cttttcatct attgcaggtt ttacagttaa gctttgctct    40140
aaggttcact atcactaaac caaaaataaa taatatggat ggtcttttcc cattttaac     40200 agagaggcta catcctctca aaccagtcag tattaggaat tcccaggatc attctctcca    40260
ttttccatcc taattagata cctatctggc accacatctc tgaaaagctc caattttaa     40320 ccagcacata ataaacaaat atgttactat taatacacgt ttgtacacaa gtcattttta    40380
ttgtcttagg tatatccact cccagacctt ctgagttatt gaaagacagg aatttgtgat    40440
gtcacctctt ttttctttt tttgagacgg agtcttgcct tatcacccag ccagagtgc      40500 aatggcgtga tctcggctca ctgcaacctc tgcctcccgg gttcaagcga ttatcctgcc    40560
tcatcctcct gagtagctgg gattacaggt ggccctagtt tgggtttttg gttttaaaca    40620
ggatggtctc ctctttgaga agttgccatg agttagccat gatgatacct gggacaataa    40680
tggtccacag agaagtaaga gccaatacaa cgccttaaga gaaagtacct ggtatgtttg    40740
tgaagcagca aagaggccaa tgtgttccag caaggagatt atagtagaga tgaagtcaga    40800
gaactcatgc ggagagggat tgtcacaaca cgcagggctg taaaggccac catgaggact    40860
tgagctttta ccgcctgtga atggggagc agttacaaag attttaaga aagcagccca      40920 gtgcagtggc tcatgcctat aatcccagct ctttgggagg ctgaggtggg tggatcacct    40980
gaggtcagga gttcgagacc agcctggcca acatggcgaa accttgtctt tactaaaaat    41040
agaaaaatta gctgcgtgtg gtggccatgc ttgtaatccc aaatactcgg gaggctgagg    41100
cagaagaatc acttgaaccc gggaggcgga ggttgcagtg agccgaggtt gcgccactgc    41160
cctccagcct gggcaacaaa gcgagactcc gtctcaaagc cagaaaaaaa gattttagg     41220 aaggaatga aatactctga cttaaatttt agaaggatca ctctggttgc tatgttgcat     41280
tatagactct aagggtagaa ccaggggagag caattaggac actgttacag taatctagga   41340
gaaaagtgat agaggcttgc accaggggtag tatcaggaga aatggtaaca agtggttgga   41400
ttatgattat agttgaaggt cgaacaacta gatttgctga tagattggat aaaatggtcc    41460
tctctttatg gatctcataa tacagtagga gaaacagaca cataaatagt catcactgca    41520
ggatgggtat tagaaatatt ttgcaagggt gtaaaaggtg ctaagaaagc tttcttgtgt    41580
gacaaagctg gttaaagaaa gaaaagaaag cttcctagaa gtgaaaccta aaatatacac    41640
ttagataaat gaataaaagt tatgaaagaa tgtgagggct gggcacagtg gctcatacct    41700
gtaatcctag cactttggga ggttgagtcg ggggtattgc ttgagtccag gagtttgaaa    41760
ccagcctgga cagcgtactg agaccccatg tctaaattta aaaaaaaaaa aaatagccag    41820
gagtggtgat gtgcacctgt agtcctagct acttacttgg gaggctgagg caggaggatt    41880
gcttgagctc aggaggtcga gactgcagtg agccatgagt acaccactgc actctagtct    41940
gggtgacaga gtgagaccct gtctcaaaga aaatgaaaag aaaaagaatt tgagaaaaga    42000
tatgtcagga aaatgtgatg acatgaacaa atactcaaag gcaagaaaag catggtgagt    42060 agggagggt acaggttgag acatgaagtt gggattgccg aggcgtaaga ggtataggca     42120
gatcatggat ggcctggttt gtcataggaa ggagcttggg ctcttatctg tgggcaatgg    42180
gaagccacta aagggtttta agtagaagag tgttatatgg taaggtttc ctctccagta     42240 gatcactcag atgactgtgg gggttggatg tgaggaggta aagcagcaaa gttactgctt    42300
taatttaaat cattgattaa tctgtacaat cctagtcatt ccaaaaagaa acattagtcc    42360
tttaacagaa gtgaattggg tctgggcgcg gtggctcacg cctgtaatcc cagtactttg    42420
```

```
ggaggccgag gcgggcagat cacctgaggt caggagtttg agacaagtct ggccaacatg   42480
gcaaaacctt gtatctacta aaattacaaa aattagctgg gcatgggggc acccacctgt   42540
aatcccagct attcgggagg ctgaggcagg agactctctt gaacccataa ggcagaggtt   42600
gcaatgagct gaggtcgcac cactgcgctc cagcctgggc gacagagtga gactccgtct   42660
ccaaaaaaaa gaaaaaatat tggagcagtt tcacagatgc tgtttactgt tatactgtat   42720
gtgtctatga ctcctcctcc aagaaaaaaa aaatgaattg gagcaggttc acagaagcaa   42780
tgtactgtta cactgtatgt gtctgtttct acacatataa atctgaattc tgtgtacacg   42840
aaaagaaatc ctatagcttt ttattcctag ctataaaaac taagaatata atttctttct   42900
ttttattaca taatgaatgg ttctgttaac tttttgttaa aatttcattg aggggagtat   42960
taattcacat ttatgtacgg atgtctacat ttacaaatca gtgtattttt tgatttatgc   43020
ttttactgag acaaagggtt tctgtctcag catggtcatt taaagagttt atcattgaga   43080
aaaatcagat gaccaacctg ttagctcaaa aaaaaaaaaa cctccaaggt atattgtatc   43140
agccagttct aggatacaaa agccatgcag tactttgtgt tttgtgccaa aaagggtagc   43200
tgctatttga cctgtcccaa aggcatgtgt ggttgtaccg taaaccaagc atggtacctg   43260
tttgtcaaac tttagaaatg aaagtttaag agagttaata tataggtgct gcattttta   43320 tgtattcatt gacttgctgg tacagaagaa aagaatcaat tatgattcag cacaatactc   43380
cacttgggga agagagtgca gcagtagttt agagtgtcag ggatcaaact gctaccttct   43440
tgggcttcag ttgctagact taagagaccc agatcttggg aggggttttt gttgttattt   43500 gatgtgggg taaggttgaa atactccctt ttaattgatt aatataaaaa ataggtaatg   43560
tagacgtatg tcacaaaatt ttaacaagtt tgagtgtgaa aagcatccat cccattctat   43620
gccctggcta cccatttccc ctccctagag gcggctgtta ttatcagttt ctctgggtcc   43680 ttttagagg taatcttttt gtatgcaact gtgcacatgt atgtttacac aaatggtagg   43740
gtattgtata tatatacagt tactgcagta tgcttatttg actttgcttt attgcttta   43800 ttttctgcct gacatatgtt aatgtggcca aatagggcat ttcccagaca atccttatag   43860
tttcattctg tgctacttta aatgctgttc tccttccctg aaatgtcctt tttttttttc   43920 ttttctttt tttttttga cagagtctc gctctgtca cccaggctgg agtgcagtgg   43980
cacaatctca gctcactgca acctccacct ccccggttta agccattccc ctgcctcagc   44040
ttcccgagta gttgggacta caggcgcgtg ccaccacgcc cggatacttt tttgtttgtt   44100
tgttttagta gagacagggt ttcactgtgt tagccaggat cgcctcaatc tcctgacctc   44160
ctgatctgcc tgcctcagcc tcccaaagtg ctgggattac agacgtgagc cactgcgcct   44220
ggctgtcctt tcttttaatc ttttcaaatt ctagccagtt catagcccac ttgctctgta   44280 aagcttttc agtgatcttt cttttgtacc atgcagtctt ttaaaaaatc tacagttta   44340 ttataagttg ctaattatat ttaataaata cctaaatggt agaaattgat tcatttttta   44400
atctccgtag tgccaggaac tgtggctcat gtctgtaatc cctgcacttt gggaggctaa   44460
ggcgggagga tcgcttaagg ccaggagctt gagcccagcc tgtggaacat attgagaccc   44520
cgtctctaca aaaataaat tagctgggca tagtggtgtc tgtatgtagt gtcaactact   44580
caggagactg aggcagaagg ataacttgag ctcagggagt tgaggccaca gtgagccatg   44640
atggtgccac tgtacttcag cctgggtgac agagcaagac caagaccgat aattatctcc   44700
atggtatttg ttttggacgt attagatatt cagtaaaatat tttctggtga tgatagtgat   44760
```

```
atctaactac ctcaggttac ctaacctgaa taaggcctat ttttaacata gccattcact    44820
tgttaatttc tgttattttc gtgacttcat ttttactaat tatattttaa aagataattt    44880
tatataaatg caaaaacttt ttatcatgta acaatctggt aacaccttga gtaatttgtc    44940
atttcacatg cacattttat ttgttcatta tctttttttct ttttgtttat tttttctgtt    45000
ttttaccttc tctgttgcat agagaagatg caaccagttt tgccattttc caagtcacaa    45060
acggacgtct ataatgacag tactaacttg gcatgccgca atggacatct ccagtcaggt    45120
gggtttaggt taactaacat aaaataataa agcttgcatg caaagtaaga gtcttactta    45180
acctgataat gttgatttga ttttataatg gtaggtttaa ttgttcatgt tttcacaggg    45240
ctgtgttgaa aatatagtac ctttatcatc atagtatata aacatgcaac aagtcaggta    45300
tagtcattct aaacttgctt tatttgcata ttttgcaacc tctggttttt cagattataa    45360
aatatgaagg tatacattcc cgtaagtgat taaaataatc tttttttctg ttgtggcttt    45420
tgtgttttta tatggatagc tatactgatt tttttcatga aatagtgttt tctaagacac    45480 atttttaattt tttatgtatc aattttttatt gcatatcaat tttcatttat agtatatgtg    45540
aatgtcttat agtacttgat agaagaaatt tgaaacttca catagtgagg agaaacatta    45600
cagtattatt tgctatggat taactctatc cttcataaac ttttggatat caacttctac    45660
agaagattaa atgtctttct gttttgtttt ctttgggtag gggactctcc atttcttagg    45720
ttctctgaca tctgagctag cttttttgttt aattaaaact ttttttttag ttgacagata    45780
atgtacctgt tcatggggta cacagtgatg ttttgataca tatagtatat ggtgattaga    45840
tcaaggtaat tatcatttcc atcatcccaa acatttatca ttccttgtgt tggaaacatt    45900
cagtattttc cttctagcat ttgaaatgat ataatatatt atattgttac ctataatcat    45960
cctgcagtga tgtagaacaa tggagcttac tctttctatc tagctatacc tttgtatcct    46020
ttccctaccc ttttcagcct ctagtatcct ctgttctact ttttattct atgagattaa    46080 cttttttaaaa ataatattct gtgtgtatat ataccacatt ttctttattc attcgtctgt    46140
tcttggacac ctaggttgat tctgtatctt ggctgttgtg aatagtgctg cagtaaacat    46200
ggggtgtaga tgtctgttcg atatgatgat tttctttcct ttggataaat tcccaatagt    46260
gggattggtg ggtcatatgg tagttctgtt tgtagttttt gaggaacctc catactcttc    46320
tccatagtag ctgtactagt ttagattccc aaaagtagcg tataagagtt cactttctac    46380
acatcctcac cagcatttgg tacttttttt gtcttttttga taatagccat cctaactggg    46440
gtaagatacc ttgttgtggt tttgatttgc atttccctca taattaacga tgttgagcat    46500
ttttccatat ctttgttttt gacggtccag ctagttttat tggttacttt tttttttttt    46560
ttttagcaat agtttcatgt gcagggctca aattatattt aatattactt ttttcaaatt    46620
ataccagaac aaccttaggt taggctataa acaactgcc ttcttttcct tttggcataa    46680
taattatata tatatttttta attacacttt acgttctagg gtgcatgtgc acaacatgca    46740
ggtttgttac atatgtatac aagtgccatg ttggtgtgcc gcacccatta acttgtcatt    46800
tacattaggt atatctccta atgctacccc tccctctcc cctcacccca cgacaggccc    46860
cattgtgtga tgttccccac cctgtgtcca agtgttctca ttgttcagtt cccatctgtg    46920
agtgagaaca tacggtgttt ggttttctgt ccttgcgata gtttgctcag aatgatggtt    46980
tccagcttca tccatgtccc tacaaaggac atgaactcat ccttttttgat ggctgcttag    47040 tattccatgg tgtatatgtg ccatattttc ttagtccagt ctatcattga tggacatttg    47100
cattgattcc aagtctttgc tattgtgaat agtgccacag taaacataca tgtgcatgtg    47160
```

```
tctttatagc agcatgattt ataatccttt gggtatatac ccagtaatgg gatggctggg   47220
tcaaatggta tttctagttc tagatccttg aggaatcgcc acactgtctt ccacaatggt   47280
tgaactagtt tacgttccca tcaacagtgt aaaagtgttc ctgtttctcc acatcctctc   47340
cagcacctgt tgtttcctga gttttaatg atcgccattc taactggtgt gagacggtat    47400
ctcattgtgg ttttgatttg catttctctg atggccagtg atgatgagca ttttttcatg   47460
tgtcttttgg ctgcataaat gtcttctttt gagaagcatc tgttcatata ctttgcccac   47520
tttttgatgg ggttgtttga ttttttttctt gtaaattttt ttaagttctt tgtagattct  47580
ggatatcagc cctttgtcag atgggtagat tgcaaaaatt ttctcccatt ctataggttg   47640
cctgttcact ctgatggtag tttcttttgc tgtgcagaaa ctctttagtt taattagatc   47700
ccatttgtca attttggctt tgttgccat tgcttttggt gttttaggca tgaagtcctt    47760
gcccatgcca gtgcccatgc cagtgtcctg aatggtattg cctagatttt cttctagggt   47820
ttttatagtt ttagaactaa catttaagtc tttaatccat cttgaattaa ttttttgtata 47880 aggtgtaagg aagggatcca gtttcagctt tgtacgtttg gctagccagt ttcccagca   47940 ccatttatta aataggaaat cctttcccca tttattgttt ttgtcaggtt tgtcaaagat   48000
cacatggttg tagatgtgtg gtattatttc tgagggctct gttctgttcc attggtctat   48060
atctctgttt tggtatcagt accatgctgt tttgattact gtaccttcgt agtatagttt   48120
gaagtcaggt agcacgatgc ctccagcttt gttcttttgg cttaggattg tcttggcaat   48180
gcaggctctt ttttggttcc atatgaactt taaagtagtt ttttccaatt ctgtgaagaa   48240
agtcatttgt agcttgatgg ggatggcatt gaatctataa attaccttgg gcagtgtggc   48300
cattttcatg atattgattc ttcctatcca taagcatgga atgttcttcc atttgtctgt   48360
gtcctctttt atttcattga gcagtggttt gtagttctcc ttgaagaggt ccttcacatc   48420
ccttgtaagt tggattccta ggtattttat tctctttgaa gcaattgtga atgggagttc   48480
actcatgatt tggctgtttg tctgttattg gtgtatagga atgcttgtga tttttgcaca   48540
ttgattttgt atcctgagac tttgctgaag ttgcttatca gcttaaggag attttgggct   48600
gagatgatgg ggttttctaa atatacaatc atgtcatctc caaacaggga caatttgact   48660
ttcttttcct aattggatac cctttatttc tttctcctgc ctgattgccc tggccagaac   48720
ttccaacact atgttgaaca ggagtggtga gagagggcat ccctgtcttg tgctagcttt   48780
caaagggaat gcttccagtt tttgcccatt cagtatgata ttggctgtgg gtttgtcata   48840
aatagctctt attattttga gatacatccc atcaatacct agtttattga gagttttag    48900 catgaagggc tgttgaattt tgtcaaaggc cttttctgca tctattgaga taatcatgtg   48960
gtttttgtct ttggttctgt ttatatgatg gattacgttt attgatttgc atatgttgaa   49020
ccagccttgc atcccaggga tgaagccaac ttgattgcgt tggataagct ttttgatgtg   49080
ctgctggatt cggtttgcca gtattttatt gaggattttt gcgttgatgt tcatcaggga   49140
tattggtcta aaattctctt tgttgtgtct ctgccaggct ttggtatcag gatgatgctg   49200
gcctcataaa atgagttagg gaggattccc tctttttcta ttgattggaa tcatttcaga   49260
aggaatggta ccagctcctc tttgtacctc tggtagaatt cagctgtgaa tccatctggt   49320
cctggacttt ttttggttag taggctatta attattgcct caatttcaga gcctgttatt   49380
ggtctattca gggattcagc ttcttcctgg tttagccttg ggaggctgta tgtgtccagg   49440
gatttatcca tttcttctag attttctagt ttatttgagt agaggtgttt atagtattct   49500
```

```
ctgatggtag tttgcatttc tgtggaatcg gtggtgatat cccctttatc atttcttatt   49560
gcatctattt gattcttctc tcttttcttc tttattagtc ttggtagcag tctatcagtt   49620
ttgttgatct tttcaaaaaa ccagctcctg gattcattga ttttttgaaa ggttttttgt   49680
gtctctatct ccttcatttc tgctctgatc ttagttattt cttgccttct gctagctttt   49740
gaaggtgttt gctcttgctt ctctagttct tttaatggtg atgttagggt gtcaattta   49800 gatctttcct gttttctctt gtgggcattt agtgctataa atttccctct acacactact   49860
ttaaatgtgt cccaaagatt ctgatatgtt gtgtctttgt tctcgttggt ttcaaagaac   49920
atctttattt ctgccttcat tttcttatat acccagtagt cattcaggag caggttgttc   49980
agtttccatg tagttgtgtg gttttgcgtg agtttcttaa tcctgagttc tagtttgatt   50040
gcactgtggc ctgagagaca gtttgttgta atttctgttc ttttacattt gctgaggagt   50100
gctttagttc caactatgtg gtcaattttg gataggtgt ggtgtggtgc tgagaagaat   50160
gtatattctg ttgatttggg gtttagagtt ctgtagatgt ctattaggtc cacttggtgc   50220
agagctgagt tcagttcctg gatctgtctt gttgatctgt ctaatattga cagtggggtg   50280
ttgaagtctc ccagtattat tgtgtgggag tctaagtctc tttgtaggtc tctagggact   50340
tgctttatga atctgggtgc tcctgtattg ggtgcatata tatttaggat agttagctct   50400
tcttgttgaa ttgatccctt tagcattata tgatggcctt cttttgtctct tttgatcttt   50460 gttggtttaa agtctgtttt atcagagagt tggattgcaa accctgcttt ttttgttttc   50520
catttgcttg gtagatcttc ctccatccct ttattttgag cctatgtgtg tctctgcacg   50580
tgagatgggt ttcctgaata cagcacactg atgggtcttg actcgttatc caatttgcca   50640
gtctgtgtct tttaattgga gcatttagcc catttccatt taaggttaat attgttatgt   50700
ttgaatttga tcctgtcatt atgatgttag ctggttattt tgctcgttag ttgatgcagt   50760
ttcttcctag cctcgatggt ctttacaatt tggcatgttt ttgcagtggc ttgtaccggt   50820
tgttcatttc catgttcagt gcttccttca ggagctcctg taagcaggcc tggtagttac   50880
aaaatctgtc agcatttgct tgtctttaaa ggattttatt tctccttcac ttatgaagct   50940
tagtttggct ggatatgaaa ctctgggttg aaaattcttt cctttaagaa tgttgaatat   51000
tggcccccac tctcttctgg tttttagagt ttctgccaag agatcagctg ttagtctgat   51060
gggcttccct ttgtgggtaa cccgaccttt ctctctggct gcccttaaca ttttttccta   51120
catttcaact ttggtgaatc tgacaattat gtgtcttgga gttgctcttc ttgagtagta   51180
tctttgtggc attctctgta tttcctgaat ttgaatgttg gcctgccttg ctaggttggg   51240
gaacttctcc tggataatat cctgcagagt gttttccaac ttggttccat tctcccgtc   51300 actttcaggt acacccgtca gacatagatt tggtcttttc acatagtcct atatttcttg   51360
gaggttctgt tcgtttcctt ttactctttt ttctctaaac ttctcttctg gcttcatttc   51420
attcatttga tcttcaatca ctgataccct ttcttccact tgatcgaatc ggctactgaa   51480
gctcatgcat gcatcacgta gttttcgtgc catggttttc agctccatca ggccatttaa   51540
ggtcttctcc atgctgttta ttctagttag ccatttgtct aatcttttt caaggttttt   51600 agcttctttg caatggtttc gaacatcctc ctttagctcg gagaactttg ttattaccca   51660
tcgtctgagg cctacttctg tcagcttgtc aaagtctttc tctgtctagc tttgttccgt   51720
tgctggtgag gagctgtgtt cctttggagg agaagaggcg ctctgaattt tagaatttc   51780 agcttttctg ctctggtttc tccccatctt tgtggcttta tctacctttg gtctttgatg   51840
atggtgacgt acagatgggg ttttggtgtg gatgtccttt ctgtttgtta attttccttc   51900
```

```
taacactcag gaccctcagc tgcaggtctg ttggagtttg ctggaggtcc actccagacc   51960
ctgtttgcct gggtatcacc agcggaggct gcagaacagc aaatgttgca gaacgacaaa   52020
tgttgctgtc tgatccttcc tctggaacct tcgtctgaca ggggtaccca ggtatatgag   52080
gcgtcagtca gcccgtatgg ggaggtgtct cccagttagg ctacttgggg atcagggacc   52140
cacttgagga ggcagtctgt ccgttcgccg atctcaaact ccatgctggg agaactacta   52200
ctctctttag agctgtcaga cagggacctt taagtctgta gaagttactg ctgcctttg    52260 ttcagctatc ccatgtcccc agaggtggag tctacagagg cagtcaggcc tccttgagct   52320
gtggtggact ccacccagtt caagcttcct agctgctttg tttacccact caagcctcag   52380
caatggcaga tgccccgcc tccagcctct tgccgccttt gcagttcgat ctcagactgc    52440
tgtgctagca gtgagcgagg ttccgttggc atggaccct ctgagccagg catgggatat    52500
aatctcctgg tgtgccgttt gctaagacca ttggaaaagc ccagtattag ggtgggagtc   52560
tccctatttt ccaggtacca tatgtcacgg cttcccttgg ctaggagagg gaattcccca   52620
accccttgcg cttcccaggt gaggcaatac cccgcccttc agctcacact atgtgggctg   52680
cacccactgt ctgacaatcc ccagtgagat gaacccagtt cctcagttgg aaatgcagaa   52740
atcagctgtc ttctgtgtcg ctcacactgg gagctgcaga ctggagctgt tcctatttgg   52800
ccatcttgga accctgcctt cttcattcat atgtaataca aaacttctaa ggttttagtg   52860
gagaagagat agagtaaaag gatttctata gacagaagaa acagttggtc atcaactctt   52920
tcccttgtgg cttcacatct cccctaagga cttcttatgt tggtttggtc ttacagtata   52980
gtcagtggca gtttccctct tcccattcct tcctctgtct gatttaaaat gctgtttcaa   53040
gtatcgatat aagtattttg cctgtttctt ttagcgtggc tgtgaagggc tgacattttc   53100
agaaggcact tactgaaaaa aaaaaaacaa agaaatgtaa gagtccatca catataaata   53160
gttaagtttc taaaatatgt atttgagatc ccagtaattc tactaggata aatagcaaaa   53220
attctccagc cctgaagagt tggtctgtct ttcctttcct tgttatcttg attctctttt   53280
atttcatttc acatgctaga ccccatcatg ttttcctgct gcattcccca ctccaccctc   53340
caaagcaatg ttctcttcct gcaacctgtt tgaaaaaatt gaactttgtc ttatttcata   53400
tccctagtac aagttgaata tccctaatat gaaatctgaa atccaaaatg ctctaaaatt   53460
cgactctttt tttttttgaga tgaagtcttc ctctgtcact caggctggag tgcggtggcg   53520
caatcttggc tcactgcaac ctccgcagcc tcccctaacc ccatccctgt gggttcaagc   53580
gattctccca cttcatcctc ccaagtagct gggactacag gcacctgcca ccacacccaa   53640 ctaattttt gtattttag tagagatgag gtttcaccat gttggtcaag ctagtctgag    53700
actcctgacc ttaagtgatc cacctgccct ggcctcccaa agtgttggga ttacagtcat   53760
gagccactgt gcctagccaa atatccaaaa cttttttgagc gctgacatga tgctcaaagg  53820
aaatactgga gtattttgca ttttggattt ttgggttaag gatgctgaac cagtaagtat   53880
aatgtaaaca ttgcaaaatg caaaaaaatg taaaaaccct aagcagttct ggtcccaagc   53940
atttcgcata agggatactc aacccataat cttttctttt ctgttttctg gttggaaggg   54000
catattggct ttatagctaa tttacacagc attgatgttt aatacacagt gagtccaagt   54060
agatcactca gacctattag tagttttatta gtgtcactca cttctggaac attctgtgat  54120
gttttacttg gatgagttct ttcacctctc ttgggaaata gtcataccaa agtctgctta   54180
ttactacaat gtgttatcta ttatacattg tccaatttc tactcaaaat tactagacag    54240
```

```
gcaaagaaaa agtaaagtat aacccttact caagaaaaaa aagcaatcag tagaaactgt    54300
gagtgggccc agatattgga tttagcagac aaagacttca aagcagctat tataatatgt    54360
ttaaagaatt gaaagaaaat atggtatcag ttaaacagga aatctaagta gatgatataa    54420
actagacaat aaaaataata ttctaaagtt gaaaagtgta gttactgaaa ttaaaaattt    54480
acagacaaca gcctcaacag cagattagag atagcaaaag aaagattcag tgactttgaa    54540
tgcaggtctg tagaaattac taaattgatg actctcacgt agcaactttc acccgtagtt    54600
tggtttcata tacaatgctt taactctttt tgctatttt tctcttactt tctgtgatgg     54660
aaacattttg tgctttgatt ttaatgggtg tatcacagtt atatacatct ttacaaactc    54720
atcaaattgt atactttatt tatatattta ttttttttg agatagggtc tgactctttc     54780
tcccaggctg gagtacagct gaattagtt gggactacag gtgggcacca ctgtgccagc     54840 taattttgt attttttgta gagatggggt ttccccatgt tggccagtct ggtctcaaac     54900
tcctgggctc aatcatttct gccgcctcag actcccagag tgttgggatt ataggtgtga    54960
gctactgtgc ctggctggta tagcttttt ttttttttt tttttttttg tgacagagtc      55020
tcactctgtc gcccagggtg gagtgcagtg gcgcgatctg ggctcactgc aacctctgcc    55080
tcccgggttc aacccattct cctgcctcag cctcctgagt agctgggact acagatgcgt    55140
gccaccatac ccagctgatt tttgtattct tagtagaaac agagtttcac catgttggcc    55200
aggatgatct cgatctcctg acctcgatcc acctgccttg gcctcccaca gtgctggcat    55260
tacaggcctg agccaccatg cctggctgtt ggtatacttt aaatggatgt aattcattgc    55320
agattatacc tcagtaaatt tttatttagt ttttgagact gagttgctct gttgcccagg    55380
ctggagtgca gtggcacgat tcagctcac tgcaacctct gcctcctggg tttaagcgat     55440
tttcctgtct cagcctcccc ggtagctgga attagaggtg tgtgccacca tgatcagatt    55500 attttttgtgt ttttagtaaa gatggggttt caccatgttg gccaggctgg tctcgaactc    55560
ctgacttcag gtgatccacc cgcctcggcc tctcaaagtg ctgggattac aggtgtgagc    55620
caccacgcct ggccttaatt tttaaatact gtaaggctta taaagaaaag aatattcccc    55680
ttctgtttct ttcctctcac gtagcaacct tcaccctag tttggtttca tatacagtgt     55740
tttaactctt tttgctattt tttttctctta ctttctacta tatttccaaa tacaatgctt    55800
ctataatgat tccttttttt tttctatcag ttttgataa tcattgactc cttatggtca     55860
aagaagactt aattcccttc tgtcactctt catatattaa ataactaat atatatattg     55920 tttagttttg atataactaa aaataactat atgtatatat aactatatat gtataagcta    55980
tctgtatata gttatatatg tatatgcaca tacatatata gttacatatg tatacacaca    56040
tacatatata gttacatatg tatatgcata tacatatata gttacatatc tatatgcata    56100
tacatatata gttacatatg tatatgcata cacatatata gttacatatg tatatgcata    56160
tacatatata gttacatatg tatatgtata tgtatataca tatatagtta tatatgtatt    56220
agttatatca aaataactat gtatatatag ctgtaaatgt atatataaac tatatgtata    56280
cagttatata tgtatttgta tatgtgtgta tacatatata gtttttttg tttttttt      56340 ttgtttttt tgtttttttt tggagatgga gtcttgccct gtccccagg ctggaatgca      56400 gtggtgctat cttggcttac cgcaacctct gcttcccagg ttcaagcaat tctcctgctt    56460
cagtctcccg agtacctggg attacaggca cgtggcacca cgccaggcta attttttgta    56520
tctttagtag aaatgggggtt tcaccatgtt ggccaggctg ttctcaaact cctgacctcg    56580
tgatccaccc gcctcggcct cccaaagtgc tgggattaca ggcgtgagca ccgcgcctgg    56640
```

```
tccctataca tatatagtta tatataccta tagttatttt tagttatatc aaaataacta    56700
tatgtatatg taactatata tatagtatat atagtatata tatactatat agtgtgtata    56760
tatagtatat atatactata tagtgtgtat atatagtata tatatagtgt atatatcgta    56820
tatacactat atactatata gtgtatatat agtatatgta gtatatatag tatatatagg    56880
atagtatata tagtatatat agtgtatata tactgtatat ataggtgtac atagtatact    56940
atatagtata catatagtac actgtatagt atatatagta tagtatatat agtatacata    57000
gtatactata tatagtatag tatacatagt atactatata gtatatagag tatatataca    57060
gtatactata tagtatatag agtatatata cagtatacta tatcgtgtgt atagagtata    57120
tatacagtat actatatcgt gtgtatagag tatatataca gtatactata tcgtgtgtat    57180
agagtatata tacagtatac tatatcgtgt gtatagagta tatatacagt atactatatc    57240
gtgtgtatag agtatatata cagtatacta tatcgtgtgt atagagtata tatacagtat    57300
actatatcgt gtgtatagag tatatataca gtatactata tagtgtgtat agagtatata    57360
tacagtatac tatatagtgt gtatagagta tatatacagt atactatata gtgtgtatag    57420
agtatatata cagtatacta tatagtgtgt atagcgtata tatacagtat actatatagt    57480
gtgtatagcg tatatataca gtatactata tagtgtgtat agcgtatata tacagtatac    57540
tgtatagtgt gtatagcgta tatatacagt atactgtata gtgtgtatag cgtatatata    57600
gtatactgta tagcgtatag agtatatata tagtatactg tatagtgtat agagtatata    57660
tatagtatac tgtatagtat atagagtata tatagttaca tatacatata gttattttta    57720
gtaatatcaa aaaccatag ctaagatttt tatgatttag caaaatattg tttaccccaa    57780
agccacgtat tatatattaa tgatatttt tccctttga gttttcttc cccacaggtt    57840
ttctgatctt ttttttgtt ctctaacttt atattatagg tatatactct tttctctgtt    57900
taatttgctt tttaactaga agacctcctt tagtagttct tttagtgaat atctgtggtt    57960
aaactcttag tctttccagt gtctgaaata ccctcatttt aatgtgacag gtcactttc    58020
tcacctcaac attttggaca tacctcattt ccaacaaaca tttgttactt ctgatagaga    58080
gtctgctgtc attctcatac ttgttccttg tggaaatgtc tatatataaa gtctcagaac    58140
tatatatttt taatatatat acatatttt atttatttaa aaatgtataa ttaagttagt    58200
agtagtagta gtagtagtag tagtagtagt agtagtagtt ttttttttt tagatggagc    58260
ctccatctcc cgggttcaag tgattctcct gcctcagcct cctgagtagc tgggattaca    58320
ggcacacacc accatgcctg gctaattttt gtattttgag tggagatggg gtttcaccat    58380
gttggccagg ctgatcttaa actcctgacc tcagatggac cacctgcttt ggcctcccaa    58440
agcgctagga ttacaggcat gaaccactgc gtctggcctt aagttattat tgactattga    58500
tgccctgttg ctctatcaag tagtaggtct tatttattct agaacctcgt tttaaggtat    58560
cctgaatgtg gctttttttt ttttttttcc taagacggag tctcactctg ttgcccaggc    58620
tggagtgcaa tggagtgatc ttggctcacc gcaatctctg cctccttggt tcaagcaatt    58680
ctcctgcctc agcctcctga gtagctgaga ttacaggcgc acgccaccac acctggctaa    58740
tttttgtgtt tttagtagag acggggtttc accacattgg tcaggcttgt ctcaaactcc    58800
tgaccttgtg atccgcccac cttggcctcc gaaagttctg ggattacagg cgtaagccac    58860
cacgcccagc ctaatgtgga ttttgttttt tttttaact tgaattttat ttatacttcc    58920
tgattttata atagttaact tgtagtaaaa gtaaactggt tgtctaaata aataagctga    58980
```

```
tttcctatac tagtttagag tctttagttt tcttaaaccg tattaagaga tttgattaca   59040
aaagtaaaat tgaggctttt gtctttttt ttggccactc taatttgctg actgacttaa   59100
catttgtctt cacagtaaac attgtaaata aacactgatg tttgttgcgt agtatgtaaa   59160
aatattattt aggagtggtg agatttaaac atttacaaac ctgtaatata tatagtacag   59220
caacactgga caaataacct tttcaactta atcagaggtg ttctataaat gttcatttgc   59280
atatatacag cccatataat acttagcata tgtaaaagca catctttata ctctttcaat   59340
taaaattgat tattattatt atttttttt tgagacagag tccctctcag tcacccaggc   59400
tggattgcag tggtgtgatc agggctcact gcaatcgggt agctggaact acagggatgt   59460
gccaccacgc ccagctattt ttgtattttt agtggagatg gggtttcacc atgttggcca   59520
ggctggtctt gaactccata cctcaggtga tctgcccgcc tcagcctccc aaatagctgg   59580
gataacaggc gtgagctact gcacccggcc taaaattgat tagttttaa daccctcttg     59640
gtgggaacag actttcatag tgtttatagt tataatagtt tggaatcaaa gtagtcgagt   59700
gctactttt tttcctctgt acatcctatc cctaatgcct ttactatatt tgtttctta    59760
tttgagagct ttatttgctt cataactttt tttttttt ttttttttg agacagagtt   59820
tcactctgtc acccaggctg gagtgcagta gtgcaatctc ggcttactgc aacctccgcc   59880
tcctgagttc aagtgattct cctgcctcag cctccgaagt agctgggatt ataggccccc   59940
accaccacgt ctgactgatt ttttgtattt ttagcagaga cgaggtttca ccatgttggc   60000
cagcctggtc ttgaactact gacatcaggt gatccgtcca cctcgatctc ccaaagtgct   60060
gggattacag gtgtgagcca tcgcgcccgg cgcttcataa cctttttata ttgtctttct   60120
gttccccaaa atgaagtagt ttcttcttaa aaatactgtt ttttgttttt ttgttttttt   60180
ttttatttga gatggaatct ctctctgtcg ccaggctgga gtgcagtggc acgatctcgg   60240
ctcacttcaa cctctgactc cgtggttcaa gcaattctcc tgcctcagcc tcccaggtag   60300
ctgggattac aggcacaaat actgttttta ataagaaaat tagaataggg acaggcacaa   60360
tggctcactc ttgtaatccc agcactttgg gaggccaagg tgggaggatt gcctgagccc   60420
aggagttcga gaccagccta ggcaacatag tgagtgagac cctgtttcta taaaaaaaat   60480
ttttaattag tccggtctgg tggtgcacaa ctgatgtccc agctacttgg gagtttgagg   60540
tgggaggatg gatcacttga gcccaggaag attaaggcca caatgagctg tgatcatgcc   60600
actgcactcc agcccaggcc acaggtttca aaaaagaga aaattagaat tatacgttag   60660
ggggaaaaa cctaataacc atattcctat ctacctagtg accaccccta tgaagatcct   60720
ggtacatgtt ctcattgaaa tcttattttg aaatatttt gaattaaaaa aatatattat   60780
taccttggtt ttacaaatgt ttgcttgtct ttatgttcag ctacaatttt ctaatcacaa   60840
tggttttact ttttccttgt cagaaagtgg agctgttcca aaaagaaaag acccttaac    60900
acacactagt aattcactgc ctcgttcaaa aacagttatg aaaactggat ctgcaggcct   60960
ttcaggccac catagagcac ctagttacag tggtttatcc atggtttctg gagtgaaaca   61020
gggatctggt cctgctccta ccactcataa ggtattctgg gacagtaact ttaattgctg   61080
tcttttgca aatagaaaaa ttttaagat actattcctg cttaagttga tcataagtac    61140
tttataatac tttagagaat ggataagttt ccataaagtt aaatttttt tttttttt   61200
tgagactctt gttttccagg ctggagtgca atggcgcgat ctcggctcat gcaacctcc    61260
gcctcccagg ttcaagcgat tctcctgcct cagcctccca gtagctggga ttacaggca    61320
tgcaccacca cgtcgagcta attttgtatt tttagtagag acggggtttc tccatgttgg   61380
```

```
tcaggctggt ctcaaactcc cgacctcagg tgatccgcct gcctcagcct cccaaagtac    61440
tgggattaca ggcgtgagcc accgtgccca agttaattt ttttttaaat ccacagggca    61500
acttgctata aaactttttt tggacctcat tagacattta ataccaagtt ttgcttaccc    61560
agtctgtttt atataatgct gtatatttca ttttaaattt attttttaaaa ttatttcaat    61620 ctttgtaaat gttttatacc agtaacatac ctagagtttt gtcatgattc taacaagggt    61680
taaaatttgt ttttattttg taaaaactaa atctctggat aaaatcctct ataactgact    61740
taatgccaaa tatagttctc tagtgaatac agttttacct tcaggtaaat aaatatacaa    61800
tttatggatt tttatacct ttttcctatt tttaaagctt gaattctgtg aacttttaagg    61860 ttaacttatt tatgaaaagt gtaaatgtta ggttgtattt tcatattaaa attttgtatc    61920
ctttaagggt actccgaaaa caaataggac aaataaacct tctacccta caactgctac    61980 tcgtaagaaa aaagacttga agaattttag gaatgtggac agcaaccttg ctaaccttat    62040
aatgaatgaa attgtggaca gtaagttttt gccatctaaa tgttttattt tatagttttt    62100
atattttaat tttacttata aaacatgtca ggagtgaaat agataataaa taccttgtct    62160
ggtttacata cttaattttt atgatagttt tcaattataa atgtagaaaa ccattgcttt    62220
actgatttaa ctatagttta acagttaaca ttaaaaataa ctatatgtca tagggcttag    62280
gcttcatctt gtaataactg ggccctgttt gtatcgtaga actaactgag gtcttgtttc    62340
ttagtggaac agctgttaaa tttgatgata tagctggtca agacttggca aaacaagcat    62400
tgcaagaaat tgttattctt ccttctctga ggcctgaggt aagaacttta tattatcatt    62460
tttctataat accatctgtt actgaatcca tagtagtagt agtagtaaag aaatatttga    62520
gctatactaa aataattaat tcatataagg taacaataga tttaatgttt taaaaaagat    62580
aaaacattaa caattgatgt tgagaagtta ttatagaata ggaaaatgga tatgagttcc    62640
taatttccaa tccttttata ttttttaggaa aagtgggtag tatgatataa ttttgtttg    62700 ttttggagac ggagtctcac tcattgtgtc gcccaggctg gagtgcagtg gcatgatctt    62760
agctcactgc aacctctgcg tcccagaatt caagtgattc tcctgcctca gcctcccaag    62820
tagctgggat tacaggcatg tgccactatg cccagctaat ttttgtaatt ttagtagaga    62880
tggggttttg ctatattggc caggctggtc tttcatacct gatgtcaagt tatccaccca    62940
tttcggcctc ccagagtgtt aggattacaa gtgtgagtca ctacatctgg ccaaattttg    63000
atatcaaggt gagagagatt taaaattaag ataaggtaca aaaattagcc tagtgtgggg    63060
gcgcacgctt gtagtcccaa ctactgggga ggctgtggca ggagaattgc ttgaaccagg    63120
aggcagaggt tgcagtgagc caagatggca ccactgcact ccatcctggg tgacagagcg    63180
agatgtcatc tcaaaaacaa aacaggccgg gtacggtagt tcacgcctgt aatcccagca    63240
ctttgggagg ctgaggcggg cagatcacga ggtcaagaga ttgagaccat cctggctaat    63300
atggtgaaac cctgtcttta ctaaaattac aaaaattagc tgggcttggt ggtgtgtaac    63360
cccagctact cggatgctg aggcaggaga atcgcttgaa cccgggaggc ggaggttgca    63420
gtgagccgag atcacgccac tgcactccag cctggcgaca gagcgagact ccgtctcaaa    63480
aaaataaata aaaatttaaa aagataaata cataaaaata aataaataat attaagagaa    63540
ggaaatcagg caggtagtgg cccctgacac aatgagtttt cccagaattg gattgcttgg    63600
aaatgccgct caaagagtgt ggtaaactcc atcgaaggct aaataccaac gtgacagtga    63660
taataaacaa gtactttatg ggaaagtttt ttttttaatt attttttaaaa agagagaaat    63720
```

```
tgtactggag aaaagaggaa ttcaggtaga ataattcttt ttttttttt ttttgagatg    63780 gaattttgct cctgttaccc aggctggagt gcagtggctt gatgttggct cactgcaacc    63840
tctgcctttg gggttcaagt gattctcatg cctcatcctc ctgagtagct gggtctatag    63900
gcatgcaccc caacacctgg ctaattttg tgtttttagt agagataggg ttttaccatt    63960
ttggccaggc tggtctcaaa ctcctggctt cagatgatcc gcccaccttg gcttcccaaa    64020
gtgctgggat tacaggcaga ggccactgtg cctggcatga agaacaattt ttaaaagaat    64080
gacttttaag gatattaagt catcaaagta gatagagcca ttaaatgatg ggtagaaacc    64140
taatcttcca tcccatattt tatgacttat taaggaagat aggcaatctt gcagttgata    64200
ataaatattt ggctttccat acttagcacc gttttgaatt tttccagttc acagatggta    64260
tatttagtgc tgttccaata atattgcaaa aaataaatct gaagactcac ttctgggtca    64320
cagttatttc actattaaca ttaaaatctt acggacctac ctgcaacatg tagtggaaat    64380
aagttgtgtg gcacgttgtg gtgggtgcat tattaaataa atgtgcaaag gttttatggc    64440
tgtctcaatt tttccatagt cttgagtcat tcacatactg cctttatggt gtttatcact    64500
tgtaagtgag taccaactgt actagaactt actgaatatt tttcaagtct attttactta    64560
ttactcattc taagtacata aaatcactgg tctgatatgc aagttaggtt ttcgctaata    64620
cccagtaaaa taattagata attattaaaa tagaaagcat ttgtcattat gtgaactgga    64680
tttatgtcat gtaccacctc aggtcacact ttgggaaacg tagcttacgt attgagctaa    64740
cattttgctg gagttatata agattagtaa atgctataga ctaaatattg aaaaaaaagc    64800
ttgcttaaag aggatttaca taattgtaga cctgaaaagg atcttagcag tcttctgatc    64860
gattcattga taaagaaact agtcctaaga gctaaaatga cttgctcaag attttagtta    64920
agtggtagac ctaggaaata cctttctaag attagagctg cctggttagt gctatagctg    64980
ccacctaatt cttacattta tttattaagg gacatgcttt ttacggtaga aaaatatatc    65040
taaaattgtg aaggtaatac caaggaaata tttaggctat gcaagaaaag tcattcagct    65100
tttgctttac ccaggcctat agagaacata tctaaaataa taagtaacat gtgaatttga    65160
atttaggcat atttttcatgg tagtgacata atgtgcaatt aagaagctat aataatgtaa    65220
aaatgccagt tgcaagttat ttcaaataaa gttgaataac ctgacctcag gaggggcaga    65280
aaccttagta aacttagcaa actgagacct aaggaagagc aagatctgtg gtagagccag    65340
gtctaaaggt ttatatcctg gtacaaactt gtctatacat caccacacct gccaaatgga    65400
actttttttc cttgtagttc agatttccaa gaaagggaat attattgtcc tagctcagcg    65460
tttcacaata gactcacaaa atgaatcttg ttaagcctat gaatgggtaa gacttatccc    65520
ataacacgcc tctattgtgt aaaaaaatca gctttattcc taattccctg tagtaggaag    65580
cttgcataga ccacaataga gacattgtta gattatatca agaaggtgag tggcaggcat    65640
tcttgagtat actggaattt ttatttcatt gtagaaacac agaatcataa ttagtcatct    65700
aaaactggtt ttaaggagat aatactaaag atactcactt gaggtagatt gttctcagaa    65760
ttacttaaaa taagtgcttt aaatcttgct cattcatgaa gccatagccc tggaaggaga    65820
tattgaaaaa cttctccatc ttccttcaat cccataggac catgttttta attgtagttt    65880
aacattaaac ataattttg aaagtagcca atattaatct ttgacaaaaa actcaaacta    65940
aatagcagaa aatagaacat gccctctcct ctcgcccaaa agtaagacta cattttaaag    66000
tatatcacag tgatctgtct aaatattttt ctcaaatatt ttactaagaa agcgtatatt    66060
cttctgtcct tatttcatag atctcttctg tatcctgtgc agcttgtcta tcatttcgag    66120
```

```
cttttatatt tcttattttg ttctcttgct gcttaaatgt gattctttga gatttataga    66180
agaatgtgat tgttctccag ttttaaaaag ctcttctcta tctactaaaa tttccatgaa    66240
tttctttctt tctttttttt tttttgattg agacagtctc gctgtgttct ccagcgtggc    66300
cttaggctta agtgatcctc ctgtctcagc ctcccaagta gctgagatta cagaaatttc    66360
catgaatttc caaatatgat gttatctttc ataaagctt aaacataagc ctttcttctt    66420
tcaaaaatgt tagaacttac ctctttaaat aatcttataa agccatttct taattttgt    66480 tacctttcg aatctattaa cttgcatatc atagtaaatg aacccttagc tccatcatac    66540
cacacacctt ctactcctgt cctcccactt tttctcaccc aggctggagt acagtgaata    66600
tttagtgctt ttaaatatta ttcattacca agccaagtag cgtactattt tttccttgta    66660 cagcctttt ttcccctaaa taattgtgtt attttttcat ttgcttcatt ttcatcttat    66720
cgattgataa ttcttctgtt ccatttcagt ctaatttcca catggccaaa ccaatctaaa    66780
aacctgttaa ctcaggtctt tttttttttt tttttccca gaataccttt tcctggaacc    66840
accttcttct tttcattcga gaccaaatgc tttccatgcc tgtgtcaaag tggttgttct    66900
ctaatctgtc ttcactacca tcataatttc cttttccttt tttcctttct ttattatgta    66960
tctcctgtct tttaaattcc atattttcca ctttcatgat ttattttctc attttgatgg    67020
ctacatcttt cagtaactga gaaaaggttg tgtgagggaa tatttgaga tgctgtagtt    67080 ttgaaaatat ctttattctg ctgtcttctc attaataatt tgactggatg tcaagattta    67140
agttggaaac tattttccat gagtattttg aaggcattat ctattgtctt ctagcttcca    67200
gtgctgcttt gtattagaga cagaagatca ggaatcagga tagcattgga cttcttattt    67260
ctatttccca aagcttttg gatcttctct ttattcttat cttctgatat tttataatga    67320
tatgcttgat gcatttactt tttcttttct tcttccctct tgtacatttc tttctttttt    67380
taggtggggg caggggggaa ggagtctcac tcttctcacc caggctagag tgcagtggtg    67440
caacctcagc tcactgcaac ctccacctct ggggttcaag cgattctcct gcctcagcct    67500
cccgagtagc tgggattaca ggcatctgcc accacgccca gctaattttt gtatttttag    67560
tagagacggg gtttcaggct ggtcttgaac tcctgacctc aggtgatccg ccctcctcag    67620
cctcccaaag tgctgggatt agaggcatga gccactgcgc ccagcccctc ttggacctt    67680 ctagatattc atccttcaat tctgagaaag gttctataat tctttaattt aaaaaaagtt    67740
tttttgtttc atctttctca cttttttttt tttttttttt ttttaagaca cagtcttgct    67800
ctgtcaccca ggctggagtg cagtggtgcg atctcagctc actgcgccct tcgcctcctg    67860
ggttcgagtg attctcctgc ctcagcctcc caagcagctg ggattacagg tgcccaccac    67920
caccatgccc ggctaattgt tgtatttta gtagagacgg agtttcacca tgttggccag    67980
gctggtttca aactcctgac ctcaggtgat ccacctgctt tggcctccca gagtgctggg    68040
attacaggca tgagccaccg tgcccagccc tattctgatt tcatagatgc agtgtctttt    68100
atgtctctga gaggttttgt caagttttct tttgtttact ttattatctg tttcttcaag    68160
attcctcctc ttttctttt gccttaagct ttttcatatt ggaagcttct ctcaaatgtc    68220
tggttattct ggttgtccac ttatattacg tggaacaata aaaagttga ttaggactct    68280 gtgctgtaag taagtaaatt gttgatagtg agagcccatt aatcacagga tgatcaagca    68340
gcaagcctac tgtttatttg ggttctccca aatggctata gctgtcagtc ttttttttct    68400
ggggttattt ggcttctcta gaaagaatt ttctagtctc ttgtttggag aatacaagct    68460
```

```
tgactattgg tgttccagaa aatgggtggg aggagacgac tttgttttct gttaggttga    68520
gccatgtgaa attactaggt tttgttttgt tttctgtttt gttttgagac agagtctcac    68580
tctgttgccc aggctggagt gccttagcat gatcttggct cactgcaacc tctgcctccc    68640
aggttcaagc aattctcatg cctcagcctc ccaagtagct gggattatag gcatgcacca    68700
ccacgcctgg ctaattttg tatttttagt agagacgggg ttttgccatg ttgaccagtc     68760
tagtctcgaa ctcctgacct caggtgatcc acctgccttg gcctcccaaa gtgctgggat    68820
tacaggtatg agccaccaca cctgggctga aattactgtt tttataggtc aaaaacagtt    68880
gagggatagg catggtggct cccacctata atcccagcac tttcagaggc caaggcagga    68940
agattgcttg agtccaggag ttcgacacca gcctgggcaa tgtagtgaaa ccccatctat    69000
atttaaaaaa aaaaaataga tgaatatctt tgtttgcaga taacatgatt gcatatgtag    69060
aaaatcccaa agaaccaaca aaagagctc ctagaactaa taagtgatta tgacaaggtg     69120
tagaatacaa agttaatata caaagtcaca ttgcttttt atctaccagc agtgaacaac     69180
tggaatttga aattaaaaca caatactgct gggtgcagtg gctcacacct gtaatcccag    69240
cactttggga ggccgaggtg ggcagatcac ctgatgtcag gggttcaaga ccagcctgac    69300
caatatggtg aaaccccatc tctactaaaa atacaaaaat tagctgggca tggtggcggg    69360
tgcctgtaat ctcagctact caggaggctg aggcaggaga atcgcttgaa cccaggaggc    69420
agaggttgca gtgagccaag atcgcgccat tgcactccag cctgggggac agagcaagac    69480
tccgtctcaa aaaaaaaac acaataccct tcatattaac actaataaaa tgaaatatgt     69540
gtagttctaa caaagtttgt tgtagaagat ctatatgaga agaattatag cactcatgaa    69600
agaaatcaaa gatctaagta aactgagaga tattccatgt aaatggacag ggagactaaa    69660
tattattgag atgtcagttc ttcccaagtt catatatcga ttcagtgcag tcccagtcaa    69720
accccagcca gttattttgt ggatactggc aaactaaagt ttatatgaaa aggcaaaaga    69780
cctagaacag ccaacacagt attgaagaag aaaaaagtca gaggactgaa actacccaat    69840
ttcaagactt actgtaaagc tacattaatc aagacagcat gtcattggca aaagaataga    69900
caaataaatc agtagaattg gacagagagc ctagaaatca acccacacag ataaagtcaa    69960
ctgatctttg gcaaagggac aaagacaatt cagtggagaa aagatagcct tttcaacaaa    70020
tggtatagga caactggaca tccacatgca aaaagttaa tctagacaca gacctgacaa     70080 cttttcacaaa aataaatgga tcatagacct aaatgtaaca tgcgaactga aacttctaga    70140
ggataacata ggagaaaatc taggataaca tgagaaaaat ttttggtttg gcagtgactt    70200
cttaggtaca ataccaaaac atgatccttg aaaaaaaaaa tcagtatgtt gaactttgtt    70260
taaattataa acttctgctc tgtgtaagat gctgttagga gaatgaaaag acatgcagca    70320
gagtgggaga cttacaaaa ttcattatct gatgaaggac cagtatccaa aatatacaaa     70380 gaactttaa aactcaacaa taagaaaata tacaacccag ttaataaatg ggcaaaatat     70440
ctgaacagac acctcaccaa ggaagataga tagatgacaa caagcatatg aatatatgct    70500
caacatcatg tcgttaggga aattgcgcat taaaacaaca acaagatacc ctgccatccc    70560
tattagaatg gctgaaatct aaaacactga caacaccaaa ttctggcagg gatgtggagc    70620
agcagaaact ttaattcatt gctgatggaa atctaaaatg gtagaaccat tttgaaggt    70680 agttggacag ttttttacag aactaaagac agtttgacag tttcttacaa aactcttacc    70740
atatggtcca gcagtcttac tccttagtat ttacccaaat aagtttaaaa tgtacatcca    70800
ataaaaaaaa ctgcacatga atatttctag cagcattatt catagttgcc aaaacttgga    70860
```

```
agcagtcaag gcatccataa gtaggggaat ggataaacag actttggtat atcatgtaat   70920
ggagtattat tcagcaataa aaagaaatga tctatcaagc cacaaaaata tatggaggaa   70980
ccataaatgc atattgctaa atgaaagaag ccagtctgaa gaggctacac tataggattc   71040
tgactatatg atgttttgga aaaggcaaaa ctatggaaac agtaaataga tcagtggttg   71100
ccaagggaga cagggagaga tgaataggtg gagcacagtg gattttaag gcagtgaaac    71160 tgttctttat gataatccaa tggtggatac atgtcattat acctttgtca aacccacag    71220 aatataaaac ataagagtga accctaatgt aaaatatgga cttcagttaa taataatata   71280
tgaatatttt ttcattagtt ctaacaagtg tactacacta atacaagata ttcagagtag   71340
gggaaattgg aaaggaatga gaggttatat gggaactctg tactttctgc tcaattttct   71400
gtaaacctaa aatcactaaa aaaaagttt attttattt ttattttttt ttaattttta    71460
attttttgag atggagtttc actcttgttg cccaggctgg aatacaatgg cacgatctcg   71520
gctcactgaa acctccgcct ccagggttca agcgattctc atgcctcaac ctcccgagta   71580
gctgagatta caggcatgtg ccaccacgcc cagctaattt tgcagtttta gtagagacag   71640
ggtttctcca tgttggtcag gctggtcttg aactcctgat ctcagggat ctgcccgcct    71700 cggcctccca aagtgctgtg attataggcg tgagcagctg cgcccagcag gttttttttt   71760
ttaagttgga tattagccat ttcatatgat tcaacttaaa agtacataca ccttcactgt   71820
tattaaagtg taggtgagat gttttcagtc tggagctcta cccttgattc ctgccatgcc   71880
tagtgtccct gaatctggag actctgactt atttctttag agaacgaaac tcctgccttc   71940
tgctttggtg gtgattggta cctgcttgac tgcctttggt ggggagttcc tcataccaac   72000
tttcaatcag ttcctgtgtt tgtttgtttg tttgttttg agacggagtt ttgctctgtc    72060
gcccgggttg gagtgcagtg gcgcaatctt ggctcaatac acgctccgcc tcccgggttc   72120
acgccatttt cctgcctcag cctcctgagt agctgggacg acaggcaccc gccaccacgc   72180
ccggctaatt ttttgtatt tttagtagag acggggtttc atcgtgttag ccaggatggt    72240
ctcgatctcc tgacctcgtg atccgcccgc cttggcctcc caaagtgctg ggattacagg   72300
cgtgacgact gtaagccacc gtgcccggcc agttcctctg ttttgactg cctgccttac    72360 tactgctttc tgtggtgcct gataacatcc aattcctgaa ccttcctggg attttgttc    72420 acgtcagcgt gcttcttgca tttaggtatc ccttcacaag taggcattta ggttttaagc   72480
tctgctaagt gatttaccac actttatcag ttctccattt tgtggaattc attgtgttaa   72540
tctccttttc tatttttgtt tggaagattc atatatttt tattcattta gtattttttg    72600
gtgggatttc taagtagaga acatgcctg tgttcaatat gtcttgttta agcagtctgc    72660
tttcattttt accaccgagg agttggtttt atttcttttt tttttttttt tttttttt     72720 ttttgagaca gggtctcact tgtcagcca ggctggagta cagtggcaca atcaaagctc    72780
actgcaccct tggcctccca agctcaagtg atcctcccac ctcagcctcc tgaatagctg   72840
ggagctcagg tgatccagca cacccagcta atttttttt ttttaattt tttgtagaag     72900 cagagttccc ctatgttgcc caagctggtc ttgaactctt gggctcatgt aatcctcctg   72960
tctttgcccc ctaaagtctg ggattacagg tgtgagccac cacacccagc tgttttaat    73020 tattacatta atttatgatt atgtgtttcc tttaaagcta tgggcagctc tgtttgggaa   73080
gatgctactg aaaaaaggat gcttttaga tggcaaagag tacttaaaat gtctctagaa    73140
tcatagttgt aaactaaagt atatatttt tagttgttca cagggcttag agctcctgcc    73200
```

```
agagggctgt tactctttgg tccacctggg aatgggaaga caatgctggt aagggttctc    73260
ttcaaatttg agttttctgt tgagatattt gggataatat gaaaaaaaga aactttatct    73320
tgtccttgag tctattattt acgacttgct ttttgctatt gtacactttt gtttttttg     73380 tttgtttgtt ttgttttgtt ttgagtgatc tgggctcacc gcaacctccg cctcctgggt    73440
tcaagcgatt ttcatgcctc agcctcccaa gtagctggga ttacaggcac acgccaccac    73500
acctgtctag gttttttatt tttggcagag acaggatttc gccatgttgg ccaggctggt    73560
gtcgaactcc tgacctcaag cagtcctcct acctgggcct cctaaagtga tgggattaca    73620
ggcatgagcc actgcacctg gctgatacac ttttaagttt ttcagctact tttcaatgta    73680
gaagtagatg gaaaaccatg tacgttatct tcagtagtgt gttttggtt ggttaaattt      73740 gacagtatga ttgtcattat tttttgtaaa ttaaattttt acctggaaga gcttacctta    73800
ctatattgag tatctttcta acccctgatt tttgcttcta ctatcataat aactttattt    73860
aagtaatcag tatgttatag cttttttttt tttttaagta ttcttttgcc agaagtttt     73920 atcaggctct ggatacctct ttcctctgca tagtcctcct ggatggaaga aacaaagagg    73980
gaaagagtaa cttttcctta gatgtttgtc tttctcaaag cagttatctt tgtatatcta    74040
agaagagagg agaataacac tgtctctctt tttttttaaa tctctctcta ctcattctct    74100
ctcaggagga gagtagaaag aagcacagct cttcctataa cctgtcctta ttactgagaa    74160
aggaacacat tgattgccat gtattgggga ttgtattata ccttacattt ttattttat    74220 ttttattaa tttttttttt tagacagtct tactctatca cccaagctgg agtgcagtga    74280
tgtgatctcg gctcactacc atctcttcct tctgggttca agcaattctg ccacgtcagc    74340
ttcctgagta gctgggatta caggcatgcg ccaccacgcc tgactaattt ttgtattttt    74400
attagagatg ggatttcacc atgttggcca ggctggtctc aaactcttgg cctcaagtga    74460
tgcgcctgcc tcggcctccg aaagtgctgg gattacaggc atgagccacc acacctggcc    74520
tcatagctta catttttaga gaatcttttc tagtacttaa atcggtaaat atggttatct    74580
tttaaatgta atatattgaa ctaatttaat atttgctctt gtgattttta aaggctaaag    74640
cagtagctgc agaatcgaat gcaaccttct ttaatataag tgctgcaagt ttaacttcaa    74700
aatacgtgag tgctctgttt ccaatattgt cgtatttaa gttactgtct aaatgttact     74760
gtgttaactg taaatggtaa tatttcatga aaatattttt ctaggagctt atctattgta    74820
tctattattt acatatgatg aatatctatc ttcagagtag aaagttatgt acatttgtgt    74880
tgtcaaatac tgtattagtt tactggggcc atgtaataaa ataccgtaaa ctggctggct    74940
taaacatcag caatttattg tctcacagtt gtggaaggta gaagtctaag atcagtcaaa    75000
atgttggcag ggttgcttcc tcctgagggc tgtgagggaa aatgtatgtt gtgtgcctct    75060
ctcctggctt ctggtggctt gctggcaatc ttttgtattc cttggcttgt agatgcatcc    75120
ctcctatctc tgtctttatc tttatgtggc attctccctg tgtctgtcac catgtccaaa    75180
tttcccctgt ggattaggac ccaccctaat gatctcaatt taagtttgtc atcagcaaca    75240
attctatgtc caaataatgt cacattcata ggtactaggg ataggacttc aacacgtttt    75300
tggagaacac agttcaaccc attaacaaat actatcactt tccacttaag cttcaagtaa    75360
agtggatttt atctcaagga gccaccagat aggaacacag atctgatggc ataaactgag    75420
tatttctggc cttctgattc tgatctaaaa tatgacagaa gattttccct gttttaattt    75480
tttttttttt tttataatag agacacagtc tcgctatgtt gccaggctac tttcaaattc    75540
ctgggcttaa gcaatcctcc tgcctcggac tctcaaagtg ctggaattac aagtgtgagc    75600
```

```
caccacacct ggccagtaga ttttccctgc tttcttttga ttgtttataa ttttgttttc   75660
tttttccatt caccctctgc tgaccctata gtattattca aagaagtgtt cagtctagtt   75720
ttggggtagg gcaagcataa ctacagtgct taaagagagt aatttgtctg gtgtgcagaa   75780
ctagtgtgta aatataactg gtgcattgca aaactgtgaa gtagtttctg tcaaaccttagaa   75840 cactgctttg tctttctccc tctctcccct tctcttggtt gccccctccc cctcccaatg   75900
ataccttagt ctctgcttgc ctttatcaaa acctttatga ttggccgggc acagtggccc   75960
atgcctataa tcctagcatt tgggaggct gaggcaggaa gatcacctga gcccagaagt    76020
tggagaccag cctaggcaac atggtgaaac cccatctctt ccaaaaataa aaatagagc    76080 caggtgtggt ggcatgcacc tgtagtccca gctactcagg aagctgaggc gagaggatct   76140
cttgagcctg agaggttgag gctgcagtga actgtgatca tgccactgca ctccagcctg   76200
agtgacagtg tgagaccctg tctcaaagaa acaaaacaag gggggcatg  gtggctaact   76260 cctgtaatcc cagtactttg ggagactgag gcaggaggat tgcttgaggc caggagttca   76320
ataccaccct gggcaacata gtgagacccc catctctaca aaaataaaa aatttagctg    76380 gacatgccag cgaatacgtg gtcccagcaa atcaggaggc tgaggtggga ggatcacttg   76440
agtcaaggag gttgagttg cagtgagcca cgatcatgcc aatgcattcc aacctgggcg   76500
tcagagcaag accacgtctc aaaaacaaaa caaaacaaac ttttatggtt gaaagtgttt   76560
tggcaaacat acttaaactg aaatgtgaat ctctgatgaa agaacatgtt acctgtaaaa   76620
gtttgaagtg tcagcatttg ttgcaccgaa atccagaggt gaggccaggt gtggtggctc   76680
acgcctgtaa tcccagcact ttgggaagcc aaggctggca gatcacctga ggtcaggagt   76740
tcaaaaccag cctggccaac attgcaaaac cccgtctcga ctaaaaatac aaaaattagc   76800
cagacttggt ggtgtgcgcc tgtaatccca gctattcggg aggctgagac acgagaattg   76860
ctcgaaccca ggaggcagag gttgcagtga gccgagatgg caccactgca ctccagcctg   76920
ggcaactgag tgagactctg tctcaaaaaa aaaaaaaaa aaaatccag aggtgaatcc    76980 agaggtgatc accacatgat atccagatag cctctttcca tgagaggctc aaaggataat   77040
tttactgtct acagttttgc agcgagagaa acttgatttt atcagtacac caagagcaga   77100
tctatgtctt cggaacagac atgagatcag aattgtctag ctgctatgaa cagcatgttc   77160
tctccctgta cctatagaca tgtatgggaa acttatttgt aaggttgtat aatgagcagt   77220
gagttaaagc aaacttgaca tgttgaccat agttgttatg gcattggact aaagtagcct   77280
ccatcactat gatagagata gccttggtgt tggacccata gttttttgaag tctgtttgct   77340 aagactccct cttccttagg cagttcttca aatattatta tgcttttttcc tgtcatggga   77400 ttcctcttca tggagtttcc tttctcagga acactatctt ctcctggtta atttgtactt   77460
attcttcaga taccagttga aatgttacaa ccttccctga ccctccaaac tattcccgt     77520 tattattctc ctagcaccac ttgcacctca ttttcatact cactggagtt gcaattcata   77580
ttcattgata ggattatttt aattgtatct gatatcactg tcacctccac tagaagatgg   77640
tctccatgcg ggcagagact atcaccatgt gttcttcact tcaattttca gtagttggct   77700
gtgagtaggt attgaataaa tatttgtgga gtaatcataa tgaggtatag atattattct   77760
catagctcta ttttattaat tagggaatta cagaattcag tgatctgctc aggatctcat   77820
aaccaggaag tgggaaacta ggatttgagc tccagtgagt gtggcctttc attaaaaata   77880
ttacagcaac cattctcttt tttttttttt ttttttttga gatggagtct tgctctggag   77940
```

```
tgcagtggcg tgatctcggc tcactgcagc ctctgcctcc cgggttcaag tgatcccect     78000 gccttagcct gctgagtagc tgggactaca ggcacccgcc acgacacttg gctaattttt     78060 gtatttagt agagacgggg tttcaccatg ttggccagga tggtctcgat ctcctgacct     78120
tgtgatccgc ccgcatctac ctcccaaagt gctggattat aggcgtaagc caccacaccc     78180
ggcctacagc aaccattctc ttttatccat acttttttca agagtactgt ttcatcttca     78240
tgttttcaga aacaacatag cattcatgat cttaaccccc aattctgata ctgcctgaat     78300
atcttgaagt aagtttactt ttaagaaagt tgaggctagg tgtggtggct catgcctgta     78360
atcccagcac tttgggaggc caaggcaggt ggatcacttg agctcaggag ttcaagacca     78420
ggctgggcaa catggcgaaa ccctgtctct accagaaata caaaaaatta gtcgggcgtg     78480
gtggcgtgtg cctgtggtcc cagccacttg ggagactgaa gtgggaggat ttcttgagct     78540
tgggaggtgg agtttgctgt gagccgagag atcatgccac tgtactccag cctgggtggc     78600
agagtgagat cccatctcaa aaaagaaaa gaaaagaaa attgaaatgt ctagtctatc     78660
attttgtcag ttctatctaa tacaattttt tccttatgtc taactgaaat ctgcttttc     78720 taattttac atacttgatt taacaaaact caatctttt ttttttttat gagacagcct     78780
ttcaaatata taggaactta atgttatatc tgcttccctc cagtccccag aatagttact     78840
attttagttg tctttctatg gtctcatgcc agtttgtcag tatgcctaga taagaactga     78900
atattttacc tcagatgtga cctgactttg aagacttaaa aaggaagcat tgtgccaggc     78960
gcagtggctc acacctgtga tcccagcact tgggaggcc gaggtgggca ggtcaggagt     79020
ttgagaccag cctgattaac atggagaaac cccatgtttc tctactaaat acaaatctct     79080
actaaatact aaatactaaa tctctactaa aaatacaaaa gatgagctgg gcattgtggc     79140
acatgcctgt aatcccagct actcgggagg ctgaggcagg agaatcactt gagcccagga     79200
ggcggaggtt gcggtgagcc gagattgcgc cattccactc cagcctgggc aacaaaagtg     79260
aaactccatc tcaaaaaaaa aaagcagcag cattgtgtaa tattatgtag atgttgtgtc     79320
tcatgatcta tcctgagaaa gcttttggga ggaactgcat catagtcatg acaacatttt     79380
gtgttattaa aatatctaga ttattttcca caaaaaatca gttacatatg tatcttaaca     79440
tgttgtatta ttgtttaacc ttgtttattg aataactaac atgtagaaaa gtatttatag     79500
cataagtata cagctgtata cagctcagtg gattaccaca aagcgaatat actttcataa     79560
tcaccaccca ggtcaagaaa taaattgtta cctgtggccc taaatccct ccaggcactc     79620 caccatcttt atccactcac tcctctccct caaaaccact agactactaa catcatagac     79680
aaagctagca tgcctttgaa ctttatataa atctaatgat gtaggatttt gtgtgtatgt     79740
gtatttggct tctttcatca gcattgtatt tgtgagattt atccagattg ttgcaagtag     79800
ttgtagttgt gctttttac acagatttaa ttttatatt tttcttatat gttcgaacag     79860
ttaacctgct tatctattat taaaaaaaaa aaacgaaca ttcacatagt tcttaccagt     79920
ttacagtgtt ttttccacac cgtcttcaaa atgtaaagtt tggtcttcaa tacatcagta     79980
tgctgctaga tttaaatact agggaaaaaa aaatcagaga agttaataat attaactgtc     80040
acctccacta gaagatggtc tccatgtgga cagtaatatt tctcttgtat tatctgtgct     80100
aagtaaaatc ttctgtaagt ttcttttaaat atttaataa atcatagtac ttaaaatgtt     80160
ctcaatattc taaagtagtt aaaagtaact ataaatagt acctgtttt ctgatcacat     80220 tttacttcct atgtgaaatt ttacaagtcg ttactctatt tatttattga tttattttt     80280 aagacagggt ctgttctgtc gcccaggctg gagtacagtg gcgtgatcat ggctcactgc     80340
```

```
agcctcagcc tcctgggctc aagtgatcct cccaccttag catcccaagt agctgggact   80400
ataggcacat gccaccatgc ccagctaatt ttaaaaaatt ctgggggggcc gaatgcggtg   80460 gctcacacct gtaatcccag cactttggga ggccgaggca ggcgaatcac aaggtcagga   80520
gttcgagacc agcctggcta acatggtgaa accctgtctc tactaaaaat acaaaaaatt   80580 agcgggtgt ggtggcaggc gcctgtaatc ccacttactc aggaggctga ggcaggagag   80640
ttgcttgaac ctggaggca gagattgcag tgagccgaga ctccatctca aaaaaaaaa   80700 atttttttt gtagtgacaa ggtgtcactg tgttgccagg gctggtctca aacttctggg   80760
ctcaagtgat cctcccattt cggcctccca aagtgctagg atcacaggca tgagtcactg   80820
tgcctggtct tcaagttgtt attaaagcat gtttacccac attatgcaca tggtataatg   80880
gaaagtattg ttgtggaagt taggagatag ggattctagc ctagcttttt atttttttgg   80940
gacaaggtct cacttttcg ccccaggccg aagtgcagtt gtgcgatctc ggctcactgc   81000
aacctccaac tctcaggttc aagcaattct cccacgtcag cctcccgagt agctgggatt   81060
acaggcatgc gccaccacgc ccggctaatt tttgtagttt tagtagacac agggtttcac   81120
catgttggcc aggctggtct tgaactcccg acctcaggtg atccaccccac cttggcctcc   81180 caaagtgctg ggattacagg catgagccac cgcacccggc ctctagcgta acttttacat   81240
cctgaactga ccttaagaaa gtaaacttt aggcctgttt catctgtaaa atgttaatgt   81300
cataggagat gatcttttga gatttctttc agctctgata attttgtgtg tgtgtgtgtg   81360
tgtgtgtgtg tgtgagatgg agtcttgctc tgtcgcccgg gctggagtgc agtggtacca   81420
tctcggctca ctgcaagctc cacctcctgg gttcacgcca ttctcctgcc tcagcctccc   81480
gagtagctgg gactacaggc gcctgccacc acgcctggct aatttttgt attttagta    81540 gagacgaggt ttcaccgtgt tagccaggat ggtctcgatc tcctgacctc gtgatccgcc   81600
cgcctcagcc tcccaaagtg ctgggattac aggtctgagc cgccgcgccc ggcctagaat   81660
atttgtttcg attattctaa atctggtgac atttcttttg tttttaagtt aaatcttcag   81720
taaaaagaat aaatgccacc tagaggacag aaaaatttt acagtagatt atcacagacc   81780
tcatgactca ttactttggt gtataaaatg gcctttgtat ggtgtcagca cctgggaatg   81840
tctcaagggg tgttcattga ccttctggac tatctggaaa tattttgata tttattggct   81900
gggcgcggtg gctcatgcct gtaattccag cacctcggga ggccaagtta ggtggatcac   81960
ttgaggtcag gagtttgaga tcagcctggc caactaagtt agttgactat tgtgaaatt   82020 tccctctcca aataggaaag ataggattgg aaacattatt cagaaggaag aagttttaaa   82080
gaagggcagg cttaaagact atctaatgaa tttaccaata tggtaaaacc ccatcttac   82140 taaaaataca aaaattagcc aggcgtggtg gtgggcgcct gtaatcccag ctacctggga   82200
tgttgaggga tgagaatcac ttgaacccag gaggcaaaag tcacagtgag ccgagattgc   82260
accactgcac tccagactgg gctatagagc aaaactctgt ctcaaaaaaa aaaaggaaaa   82320 aaaaaaaga aattttgata tttatgtgag aatgactttt cacggtgttc ttaatagcgc   82380
aagttttgtt taggagagca cattccaact tacttgcttc tataaatata ccgtgtaatc   82440
tagggcttaa agaatatgta caatgtcttt ttctctcccc tagtcttccc cttttctcac   82500
tagttatatc cttgactgaa gagctatttc attctcaagt cttaggaatg cagggtgaag   82560
caaaacagat gaattttaa agcacttaac caggctgtat gaaatcacag tctgttgtct   82620
aaaattgtaa gggacggtta gtagtactct cccctttctc aaaccaaatc tttggttgtt   82680
```

```
ttaaggaagg gaaattaaat tcctgtgtgc tagattttca acataaaatt taaaaaactg   82740
gaataatgtt gcattttatg tgtataacag tataatgctt tgttttaggt gggagaagga   82800
gagaaattgg tgagggctct ttttgctgtg gctcgagaac ttcaaccttc tataatttt    82860 ataggtaaga acatattttc caactaagtt attgactatt tgtgaaattt ccctctccaa   82920
ataggaaaga tacgattgga aacattattc agaaggaaga agttttaaag aagggcaagc   82980
ttaaagacta tctaatgaat ttagtaggac ccactatatt aataagtagt aaactagatt   83040
aatctcagat gactcacata gcttggtctt taattaaagt cttatacttg tatttcctct   83100
agatgaagtt gatagccttt tgtgtgaaag aagagaaggg gagcacgatg ctagtagacg   83160
cctaaaaact gaatttctaa tagaatttga tggtgtaagt gttgattatg atattttaa    83220 tgtggcagca ttttagtata ttttcctatt aaatggccaa ggttaaaaat acaaatatct   83280
ttatatttgt tattactttt ctaaatgaat tgaaaaaga ttttttgctt gtaggtacag    83340
tctgctggag atgacagagt acttgtaatg ggtgcaacta ataggccaca agagcttgat   83400
gaggctgttc tcaggtaggg agatttatat ggaaatacat gcatttatta cagacaatat   83460
ttactcatgt gtccatctta catattttt ccttactctc agttttaaga ctaaattcac    83520
tattttcttc cagtactatc tctagcctct tgttaccaac tacataagga ttttgaggtc   83580
aacagcttga tatcaggaga attagtctag taaggttta gttacggttt taggcaaatt    83640
ggtcagttct tctgggttgc attaaattat ctttaaactt gaaaattgat tcttaccgtc   83700
ttttattggg cttcatgaga aaataatcaa atcagggttc atggaaaatg tgttttctgt   83760
tcttgtgtgt ttgagcagtt tattcccttc atactggaag gacggtttgg gtcagcataa   83820
aattcttggg catcctttcc caaggaattt acaatattgc tccattgttt ctagattggc   83880
tgtagtagtg taaagtctg aatccaaatt gattttttca aatttgtaaa ataacttgat    83940 tttttctct ctttactgga tgggttacgt gggtatattg cacccaggta gtgagcatag    84000
ggtgcagtag gtagtttttc aacccacacc tcactgcttt cttcccccat gtagtagtcc   84060
gcagtgtgta ttgttcccat gtttatgtcc atgtgtactc aattttagc tccccactta    84120 tgagaacatg agctatttgg tttactgttc ccacattaat tggcgtagta ttaaggcctc   84180
cacctccatc catgttgctg caaaggacat tatttcattc ttttttatgg ctgcgtagta   84240
catagtattc catggtgtgt acgtaccaca ttttctttat ccagtccacc attgatggac   84300
acttagattg attctatgtc tgctgtcatg aatagtacag caataaacat gaaatgcatg   84360 tcttttggt ataatgatct attttccttt gggtatatac ccagtaatgg gatttcaggg    84420
tcaaaggtag atttgtttta tgtttttga gaaatcttca aactgctttc tacaatgact    84480
gaactttaca ttcctaccag cagtacatac gctccacaac ctcaccaaca tctgttattt   84540
ttttactttt tcccgccaat ctgtagacaa tatgggattt tttttgccat tttattaata   84600
gccattctga ctggtgtgag atatctcatt gtgattttga tttgcatttt tctgatggtt   84660
agtgatgatg agcatttttt catgtttgtt gtcccctcgt atgtcttttg agaagtgtct   84720
attcatttcc ttttttaccca ttttttaata gggttgtgtg ttttagctt gttcaattgt    84780 ttgaattcct tatagattct ggatatcaga ccattgttag atgcagttct gtagattgtc   84840
tgtttactct gttgatggtt cttttgctg tgcagaagct ctttagttta attaggtccc    84900
acttgtcaat ttttattttt gttgcaattg tgtttgggga cttagccaaa atttctttct   84960
gaggctgatg tcaagaagtg tatttcctag ttttcttcta gcatttttat actttgagat   85020
cttacattta aatctttaat ccaccttgag ttaattttg tatatggtga aaagtaaggg    85080
```

-continued

```
tccagtttca ttttttctaca tatggctagc cagtaatccc catgccattt attgaatagg    85140
gagtccttttt cctcattgct tgtttttgtc agtcttatca aagatcagat ggttataggt    85200
gtgtggcttt atttctcaat tttctgtcct gttcctttgg tttgtgtgtc tgtttttata    85260
ccagaattat gctgtttggg ctgctgtgta gttcggttta aagtcaggta acgtgatact    85320
tacagctttg ttcttttttgc ttaggattgc tttgtctatt tggactcttt ttttgcttcc    85380
atatgaattt tagaatattt ttttctaatt ttgtgaaaaa caacattgat agtttgatag    85440
aaataccatt gaatctgtaa attgcttttgg gcagtatagt cattttacga ccagataaat   85500
caggcaagag aaggaaacaa aaggcatcca aataggaaaa gaagtcatca tactctcact    85560
cttcactggc aatatgattc tactttttga aaaccctaaa aattccgtca aaaggctact   85620
agaactgata aatgatttta ccccaagatt caggatacaa aatcagtgta caaaaaatta    85680
gtaccatttc tatacgctaa taatgtccag gctaagagtc aaatcaagaa cacagtccca    85740
tttacaatag ccacaaagaa aatgaaataa tggctgggca cagtggctca tgcctgtaat    85800
cccagcactt tgggaggctg aggcaggtgg atcacctgag gtcaggagtt cgagaccagc    85860
ctgaccaaca tggtgaaacc ccgtctctac taaaaataca aaaaattagc caggcgtggt    85920
ggtgggcgcc tgtaatccca tctgctcggg aggctgaggc aggagaattg cttgaaccca    85980
ggaggcatag gttgcagtga gccgagatcg tgccactgca ctgcagcctg ggtgtgaaag    86040
agcaagaatc cgtttccaaa attaaaaaaa aaaaagaaa aaaaaaaga caatggagta    86100
cctaggaata cggctgatga aggaggtgaa agaatctgta tgaggagaag tgtaaagcac   86160
tgctaaaata aatcagaggt gacacaaata aatggaaaaa cactccatgc tcatggattg    86220
gaagaatcaa tatcgttaaa atgggaaatt tatcttaatt ttttttcccta gttcattttt    86280
ctgttttctt ttgcacataa attatgtgtt atgttgcgtc cttttgtttt ccctatctgt    86340
aattttcttc ttcatccttt taaactctta ggtcttttttg ttttgttctg ttttcccaag    86400
cctgttgcct ttatttctta ctgggttagt atctaatctc ctttctgcta tatcttttgt    86460
aactcttctt tccttggtgg ttttttttattc attacttttcc tgacatctgt tattctactt   86520
ttcatcttct gttttatttc tttgagcatc tgtatgttat ttccataagc tcttacattt    86580
cactgggctc ttgtttcata gaaacaattt ttttggcaag acagaccac ttgaggccag    86640
gagtttgaga ccagcctggc caacatagta caaccctgtc tctgctaaaa atacaaaaaa    86700
ttagctgggt gtggtcacac acacctgtaa tcccagctac tcaggaggct gataatcgct    86760
tgaacccagg aggcagaggt tgcagtgagc caagacggcg gcactgtact ctagcctggg    86820
ggacagagca aggctctgtc tcaaaaaaaa aagaaaaaaa tttttttggtc aggcgtcatg    86880
gtgggtcaca cctgtaatcc cagcactttg ggaggccaga tcacttgagg ccgggaattc    86940
cagaccagcc tcgccaacgt ggcaaaaccc catatctata aaaaaaactt aaggataaaa    87000
aaaattaaat ttttaaaaaa ttaaattatt ttatttcgtg gaaagatact tggtcataat    87060
tttagtttgc tctatggcaa aatcttctca tgcatgttct tcattttatc tagtttatgt    87120
ttattgtgtt ttgtttgctc ttttttgggg gcaggttttg ttgttgttgt ttttttttt    87180
tttttttaa atgagccctg tcctggtttt ccttttttg cttattattt ttcttttgaat    87240
aaaggagtt ttccttggaaa acctagttttt ggaaggatat tgtaggggaa gggataggta   87300
tcttgagtag tccatgtata cactaaacta gcatgcagcc tccctcactt acagtgaagc    87360
cctacctaat aatgaagtat atgtgtatgt aaataagaga tagggttgat ttattcttct    87420
```

```
actaaaaaat attggtcact gcaagacatt gtcttcccgc cagactgtta gatgccttct     87480
tataaagata attcgtctta gagtttcttt gttcattctc accttccttg ccattcctat     87540
gctatcaatt agggtttata tggtctgcag agccaggctt catatgcttg tttaaatgtg     87600
gagggactgg ccttattacc ctttagggtg tgctatctct ttttgggagg aaaactgtac     87660
tctgacagtc atgtccatga tctttagcgg cagatccttt gtgtgtcttc ctttgtcagt     87720
gtaattttca ctgccctagg cagttcacct ttatgtattt tagttccata aatgttacct     87780
agtttgttga tgaagtgtat gtttctgttt ctattatcct tgctgatttt agtttttttc     87840
agattcaaga agacagatct acttatatca gatattttgt ttgttttaaa gcattactgc     87900
tattaaaaac atatacatac ataaatgatt aattctaaca ataccgaatt aaggatttta     87960
aacattaact agagttttaa aagagtaaca aaaatatttt tacattgata actaccaaaa     88020
tgcattccag tgccttgaat attatatttt aaaagctttt cctgtcattt gctgtttcag     88080
ctttaaattc aaaattatat ttctaaaagt gctggatttt ttttttttagg cgtttcatca     88140
aacgggtata tgtgtcttta ccaaatgagg aggtatgtat ctgtgtttga atttttttg      88200
ttttagagca gaaacaagaa ctaccatctt gacaatatta agtcttccaa tccatggtac     88260
agctactttg gaaaacagtt tagtggtttc ttaaaaagat gtacataagc ttactgtcag     88320
agccagcaat ttcactccta agaatttacc ccagagaaac aaaaatgtat gtccacacaa     88380
agacttgtac aagaattttt atagcagcaa tattaataat agccagaact acaaatgatc     88440
taaaatgttt attttggtga ataaacaaat gtggtatatt catttaatgg atactgttat     88500
ccattataca tgctgcatac tcacttcata tattaagttt tatgaatgaa actccaaaac     88560
attataagtg aaagaagcaa gatgatatat gtcgcatatc ataggattct gtttatatgc     88620
agaaaacgca aatttatttt ttatttattt atttttttga gatggagtct tgctctgtcg     88680
ctcaggctgg agtgcagtgg cgtgatctcg gctcactgca accttcacct cctgggttca     88740
agtgattctc ctgcctcagc ctcctgagta gctgggactg caggcatgtg ccaccaggcc     88800
tggctaatttt tttgtgtttt tagtagagac gggtttcact gtgttagcca ggatggtgtg     88860
atccgccctc ctcagcctcc caaagtgctg ggattacagg catgagtcac cgtgcccggc     88920
cagaaatcga aaatttctag aaacgtaaag cagatcagtg ggttgtcagg gtgagagttg     88980
ggaatgagga ttaactgcaa acaggtatga gtgaactaaa aagtgttcta aaactggatt     89040
gtggtgatga ttgcacatct ataaatgtat taaaactcat tgaattatat acttacaatg     89100
ggtgaaattc atagtagatg aattcatacc tctataaaac tggttttttg cagcaaaata     89160
tttattgcta tgttttattt caagtgtggt gaattattgc tatgttttta tccaggtgtg     89220
gtgtctcacg cctataatcc caacactttg ggaggctgag gtgggaggat cgcttgagcc     89280
aggaattcaa gaccagcctg ggcaacatag ggagaccctg tctctacaaa aactttttta     89340
gaaattaacc aggcatggtg gcacgtgcct ttggtcccag ttactcggga ggctgagatg     89400
ggaggattgc ttgaacccag gatatcgagg ctatagtgag ctatgattgt gccctgcact     89460
ccagcctggg taacagcaca agaccctgtc tcaatataaa aaaagaaaag aatcattaat     89520
tctgaaatta gactgaatga tcattttta atattttca gacaagacta cttttgctta     89580
aaaatctgtt atgtaaacaa ggaagtccat tgacccaaaa agaactagca caacttgcta     89640
ggtgagtaat ttggatttgg tttatcttac agcttttatt tattttttgt aaataattct     89700
tttttttagtt atttaaagta atcttaagta tgaaatgagt aattcattga tcagaagact     89760
ttctctcatc ctctacctcc tttgcctttt tcttacctct tgttcttata tatatatgtg     89820
```

```
gaatctaaat tcactggct atgtcctttg caagacgtga tctaatgatg atagtatatt    89880
cttttttataa atttattaaa acctgtaagt ggtattaaag taatttaaac atttacacct   89940
taggcaacat ggtaaaaccc catctctaca aaaaataaaa tgagtcagga atggtggcac    90000
atacctgtag tcccagctac ttgggaggtt gatgtgggag gatcgcttca gcccgggagg   90060
tggaggttga gcaacagagt gagaccctgt ctcaaaaaaa attttaaaca tttcatattg    90120
cacactaaca cagatatttt tatataaact tgttcttggc atatgctgaa tacttttcag    90180
ctcttttaat aattttaatt atttgataat tttaataatt ttaatttcag ctatttgaat    90240
aatcttaaac tttatgaaca gtgtgaagta gaaactgagt ataggagatg cgctcatgaa    90300
ttttattccc tgaaaatgt cataaagtaa tataaagtat tcaatgagta tgtgagtatt     90360
gaataatttt aacaagaact ctgagttccc agatacctat gacaaaagaa caaattactt    90420
ggaagtctct tctactccag acctttctgt ctatcccctt atttaaaaaa atgtacattg    90480
attgtccctt atcccatcaa gagagtgttc tttgccaaga taaacgctaa ttagagaagt    90540
aattgtgttt atgtgtcagt tggccaccag tagtttgtag atgttaccct tccaggtgac    90600
atgtttacaa tttaatgaag cctctggaga tagtatgcct taatctaaag gaatggttct    90660
aatgattaaa atttgaggca ttactacatt tgttttcagc aaatgggcct ttctattccc    90720
ttaaaatcaa accctcataa ctatgggttt gctgacaaag ggaaactagt ttttactctt    90780
attatatgga gatttaaaat ctgcagagat gaaaataatt tgctgtttca gctgggtgcg    90840
gtggctcatg cctgtaatct cactactttg ggaggctgtg gcgggtggat cacctgaggt    90900
caggagttcg agaccagcct gaccaacatg gcgaaacgcc atctatacta aatacaaaaa    90960
aaaaattagc caggtgcggt ggcgcatgcc tataatccca gctacctgag aggctgaggt    91020
aggagaatcg ctccaggagg tggagatcac agtgagctga gatcatgcca ttgcactcca    91080
gcctgggcaa caagagcaaa actccatctc aaaaaaaagc gggagggaa ataatttgct     91140
gtttcttcct tcccttcctc agaatgactg atggatactc aggaagtgac ctaacagctt    91200
tggcaaaaga tgcagcactg ggtcctatcc gaggtaggta tacaagagct taaaacatt     91260
agaactattt attataccac cttagaagtt taagaagtcc aaaaaaatct accaagagat    91320
tttttttttc ttttggagac agggtctcac tctgttgccc aggctgtagt gcagtggcac    91380
aatcatagtt cactgcagcc tcgaaccccc caggctcagg tgattctccc acccagcctt    91440
cccagtagct gggactacag gcatgcacca tcatgcccag ataattattt tatttttatt    91500
cttgtagaga cagggtttca ccatgttgcc caagctggtc ttgaactccc gggctcaagt    91560
gagcagcctg ccttggcctc ccaaagtgct gggattacag gcatgagcca ccatgcccag    91620
ccttaaaacc attcttagct cacagatcat acaaaaacag tctatgagcc agtagactgt    91680
gaccctgtt ctaggcaaga ggtttcattt cttgatagta agtaagcagc agaaaactca     91740
aaagaaaac tttaaacaaa aaagaataat gtaaggaaaa tgttcttatc tgtttctgg      91800
ctcttttcag tattctgaca tcatttgaaa ttaatgtgtc taaaggaaat tctataagag    91860
aagttttcac tttttaatt atatcttttg agggattgca gcaaaatatt tattgctatg    91920
tttttattca ggttacttgg ttgattctga aataccacga ccaattcttt ttaggttagg    91980
ttaggataaa ctcacacaga tattttcagc tacatttcca cagccagcat cggtagtgga    92040
tggttgatgc tctcaggtat gcactcgat tattagctat gatgataaag taatcataat     92100
agctccatcc ctttctctca ttcaagaaag tacaattgaa tgtagttgta cgagaaagat    92160
```

```
gttatcatag tgtctactgt aatttgcatt aaaagcctac attatacaaa ccttttgtt    92220 ttactagtta aaaattacca gtaacacctc ccgtagtgaa atagggtgct gattaagaac    92280
tgctactttg caaaataaaa aatgtaatct tgagagtata ttttgaaact ctggatgaac    92340
aaattttctt gctgctggag cttaaatctt gttcagttag tggatttaga aacagtagct    92400
aatgcataaa tgagttgtat tttcttagaa cgttttggct attctaaggt agacaaaatt    92460
tgggtttaaa aaaagattcg catccattaa agtacagaaa atggccgggt gcagtggctc    92520
acacctataa tcccagcact ttgggaggcc aaggtgggag gatcgtgtgg gcctaatagt    92580
ttgagactag actgggcaac ataggagat cctgtctcta caaaaaaata taataaatta    92640
accaggcccg ttggcatgag cctgtaatcc cagctactcg ggagtctgaa gtaggaggat    92700
cacttgagcc tggaaggtgc aggcagcagt gagccatggt catgccactc actgcactcc    92760
agcctgggtg ggtgacatag tgaggtgctg tcttaaaaag taaataaata ggccaggcac    92820
ggtggctcac gcctgtaatc ccagcacttt gggaggccaa gatgggtgga tcatgaggtc    92880
aggagttcga gaccagcttg gccaatatgg tgaaaccgca tctctactga aaatacaaaa    92940
attagccagg cgtggttgtg cgcacctgta atcccagcta ctcaggaggc tgaggcagga    93000
gtatcgcttg aacctgggag gtgaggttgc agtaagccga gcactgcagc ctgggcaaca    93060
gagcaagact ctgtctcaaa aaaaaaaaaa aaaaaaaaa aaaaagtaa atacataaag    93120 tgcagagtaa aaacaaaaaa agactaatgc attttgtaaa gaacaagttg cattctttta    93180
agttcccttt caaatttgtg aactattgtt tttgggcagt atgcaagaaa ttgaacactt    93240
tccagttatt ccaaagaagg aatattctct tctcagcatt tataaattgt atttgctctc    93300
aaagttaaca tgtgtctctt tttttaata taatgatttg tactgaatag atacatgtag    93360
atcattgtac ttggttttgc ccttcaacaa tttcaactgc aaaatgtatg tatttttaag    93420
tgcctgactt ttatgtttta cagaactaaa accagaacag gtgaagaata tgtctgccag    93480
tgaggtatag tattttacaa tgatattttc tttgtcttct atattgtaag acatatataa    93540
gacatacata tatgaatgtg tgtgtgtgtg gttttttttt tttttttttt tttttgaga    93600 cagtctggca tgatatcggc tcactgcaac ctccacctcc tggattcaag ctattctcct    93660
gcctcagcct cccaagtagc tacaggcatg taccaccaag cccagctaat ttttgtattt    93720
ttagtagaga gggcatttca ccatgttggc cagtctggcc tcagactcct gacctcaagt    93780
gatccaccca actcggcctc ccaaagtgct gggattacag gcttgagccg ctgcatctgg    93840
ctgttttgtt tgtttgtttg tttgtttgtt tgtttgagac ggagtctcac tctgtcgccc    93900
agactggagt gcagtggtgc gatctcagct cactgcaagc tctgcctccc gggttcacgc    93960
cattctcctg cctcagcctc cctagtagct gggactacag gcgcccacca ccacgcctgg    94020 ctaattttt gtacttttag tagagacggg gtttcaccgt gttagccagg atggtctctg    94080
tctcctgatc tcgtgatctg cctgcctcag cctcccaaag tgctgggatt acaggcgtga    94140
gccactgcgc ccggccttt tttttttttt ttttgagac acagggtctt gctctgttct    94200
caggctggag tgcagtggtg caatcgtggc tgactgtagc cttgacctct tggtctcaag    94260
cagtcctctt gtctcaaact ttttagtagc tgggactaca ggcaagtgcc acaacgcccc    94320
actaattttt taattttctg tagagatggt gtctctccct gttgcccagg gtggtctcag    94380
actcttggcc tcaagtaatc ctcctgcctc agtctctcag agtgcttggg actaattttt    94440
tttaatggat ttttctagtt gattagaagc tagaaaaaat taactttgct tcatttcaaa    94500
atatggaaac ctatgaaata gtcaaaattt tttttggtaa tagacaaaac atatatacat    94560
```

```
aaagtcattt tctatcaaat catattacat aaataccaaa cagaagaaaa ttacaggccg   94620
ggtgcggtgg ctcacgcctg taatcccagc actttgggag gccgaggtgg gcagatcact   94680
tgaggtcagg agttcaagac cagcctggcc aacatggtga aaccctgtct ctatcaaaaa   94740
tacaaaaaaa ttaggccggg ggcggtggct cacacctgta atcccagcac tttgggaggc   94800
cgaggcgggc ggatcacgag gtcaggagat cgagaccatg ctggctaaca tggtgaaacc   94860
ctgtctccac taaaaaatac aaaaaaatta ccggggcgtg gtggcgggca cctgtagtcc   94920
cagctacttg ggaggctgag gcaggagaat ggcgtgaacc tgggaagtgg agcttgcagt   94980
gagccgagat cgtgccactg cactccagcc tgggcgacag agcaagactc catctcaaaa   95040
aaaaaaaaaa atagctgggc atggtggcac gtgcctgtgg tcctggctac ttgggaagct   95100
gaggcaggag aatcacttga acttgggagg cagaggttgc agtgagccaa gattgcccca   95160
ttgcactcta gcctgggcga cagagtgaga cccagtctca aaaaaaaaa aattacatga   95220 aacttgtggg ggtttataca ataaaaataa cctataacta tacgttaatc ctttaataat   95280
gttctatttt gttttttcaat aacctttatt tttttaatta atttcttttt tttgagaagg   95340
actctggctc tgtcacccag gctgcagtgc agtggcacca tcttggctca ctgcagcctc   95400
cacctcccag gttcaagcga ttctcctgcc tcagcctcct gcgtagctga gattacaggc   95460
atgggccacc acgcccagct aatttttttt tttttgtat ttttagtaga gatggggttt   95520
cactatgttg gccaggtggg tctcgaactc ctgacctcag gcgatcgcca gcctcggcct   95580
ccctaagtgc aaggattaca ggcgtgagcc accatgcctg gccaatttat taccgttttct   95640 taatatggaa gacctcctta tgagatgctg aagcatttca tttgaaaaaa gttgcatgta   95700
aaatataaaa ttgggtatgc agaatggtca taactctgtg agcaaaattt tgaaatcagg   95760
cttgaattac agtcagcctt ttctatccgt ggattctgca ttcatggatt caaccaactg   95820
cagatcaaaa atacttgggg gaaaaaagca tctgtgttga acatgtacag acttttattc   95880
ttgttattat tccctaaaca atatagtata aaaactattt acattgcatt tacattgtat   95940
taggtgttat aagtaatcta gagatgattt aaagtataca ggaggattgt gtaggttgta   96000
tgcaaatact gcaccatttt acataaggga ctttaagcgt ttgcggattt tgctatctat   96060
gggggaacca atttccgaga gatactgagg gacagctgta tatttgtaac ttatttttta   96120
tttccctaat tgcagcagct gttgagggga cagtgaactg ttaacacaga taacaagtgt   96180
attcaagtac attttggagt ttgtttgttt tttttttttca ggcttttatt cgcctgtcgg   96240
atgaggcacc atacttgaat tttttttttt aagaaagctt ttagttttct ttctttcttt   96300
tttttttttt gtgagatgga gtcttgctct gtttctaggc tggagtggag tgcagtggtg   96360
tgatctcagc tcactgcaac ctccgcctac tgggttcaag tgattctcct gcctcagcct   96420
cccgagtagc tgggactaca ggtgcacgcc accacgccca gctaattttt tttttttttt   96480
tttttttttg tatttgtagt agagacagag tttcaccatg ttggccagga tggtctcgat   96540
ctcctgacct tgggatccgc ccaccttggc ctcccaaagt gctagggatt acaggcatga   96600
gccaccacgc ccggctgaaa gcttttagtt ttctaactta tttaatttaa tttaatttaa   96660 tttatttta ttttattttt tgggacagtg tctcacttgg ttgccaggc tggagtgcag   96720 tggtacaatc atggctcact gcaccctcta gctcctgggc tcaggcaatc ctcctgcctc   96780
agccttttga gttgctggga ctacgggcat gtaccaccac actcagctaa attttttaatt   96840 ttttgtagag atggggtctc actatgttgc ctaggctggt ctcagattcc tcaagcattc   96900
```

```
ctcccacttg cacctcccaa aatgctggga ttacaggtgt gacaccgtgc cagacttgaa    96960 attttttaatc ccacacctaa aaatataatt ttatccacca ttttttaaaa gtcataacat   97020
tatttattaa aaatttagat ggtaaaacta aaaattaaag cttaataaaa ctactgagtg    97080
atttacaagg aagaatatta ctggtccctt ttgtgagcat cccattaatt atatatattc    97140
aggttatatt gttacaatat ttggttctac tgtatacttt ttttttttgag actgagtttc   97200 gctgttgttg cccaggctgg agtgcaatgg tgcaatctcg gctcactgca acctccgcct    97260
cctgggttca gtgattctc ctgcctcagc ctcctgagta gctgggatta caggcatgcg     97320
ccactatgcc tggctaattt tgtgttttttg tagagacggg gtttcactat gttggtcagg   97380
ctgatctgga actcccaacc tcaggagatc cgcccacctc ggcctcccaa agtgctggga    97440
ttgcaggtgt gagccaccat gcctggctct actatatact ttcattcagt tgtttctttt    97500
taatctagtg gttttggtat taataatttg ataatgacct ttagctgtta ttgcttactt    97560
atgagttaat atttataaag cacttaaagt agctggcacg tagtaaacac tatgtaaaga    97620
tccattaaat aactttaaaa aatataaaac tgatagtggc atttttattat agagattaag   97680 gtaatccatt ctctcatttc catttatggg atgagacgta aacacaagta gtttgctctc    97740
taaaactgta tactagaatt ttatataccc attatttgat gcaactttaa taccaaagtg    97800
tattgtcagt taccggtgaa tatatataaa tttaggtaag gaaaacccaa cttggtcgca    97860
cacagtggct cacgcctgta atcctaccac tttgggaggc cgaggcagtt ggatcacctg    97920
aggtcttgag ttcgagacca gcctggccaa cgtggcgaaa ccccgtctcc actaaaaata    97980
caaaaattag ccgggcgtgg tggcacatgc ctgtaatccc agctgctcgg gaggctgagg    98040
aaggagaatt gcttgaacct ggggaggtgg aggttgcagt gagctgagat cgtaccactg    98100
cactccagtc tgtgcgacag gagcgagact ccatctccaa aaaaaaaaaa aagaaaaacc    98160
caacttatct tttacagttt ataatagtag aagttcaaat aattggtttg gaatttctgt    98220 attttttaagg ttagtactaa aattgttggt tataaattgg ggtacaatat actttgtttt   98280 ttaagtaccct tgtgtatcta atttaacttt aagtccttta ttattttggt ttgataagac   98340 aactttcta cttatttccc cccttaactg aaccagctac catctgcctt tttcctgttg     98400
tatacattag tctcttacgt taaaatatca tataagtttc atatatatac acatatcaaa    98460
ctatagactt aaagtacaat tacatcaaca tcttttaaaa ccttaatttc tggccaggcg    98520
tggttgttca tgcctataat cccagcactt tgggaggctc aggccattgg atcccttgag    98580
ctcaggaatt cgagaccagc ctggataaca tggtgaaatc ctcatctcta caaaaattac    98640
aaaaagttag ctgggcgtgg tggcgcacac ctatagtcct agctacttgg gaggatctct    98700
taagcctggg aggcagaggt tgcagtgagc cgagatcatg ccactgcact ccagcctggg    98760
taacagtgag accctgtctc aaaacaaaaa tattaatttc tataacaaat aaattttatt    98820
tagtaatatc atgtttaata cccatgttac attcattatt cttctacact ttggcccttta  98880 ggaagaggca gtgtgtgtgt tacagttaaa taggaaacaa gtagggttca tatagtgctt    98940
atggggtttt ctttggtggg gggttgctgg gtttttgggg ttttttttttt tgagacaggg   99000 tatcactctg tctcccaggc tgaaatacat tggcatgctc atggctcact gcagcctcaa    99060
cctcccagac tcaagtgatc ctcccacctc agcttcccta gtagctgaga ctacaggcgt    99120
gcgccaccat gcctagctaa attttgtaca ttttgtagag atgaggcttt gccatgttgc    99180
ccaggctggt ctcaactcc tgggctcaag tgatccactt gcttcagcct cccaaagttc     99240
tgggattaac aggtgcgagc cactgcagcc agcctatatt ttaactatat gttttttttct  99300
```

```
ttttggctaa aatttttcag attagtttac aagttacaag tgtaggtgat atctcatgga   99360
gatatcaaag atgatatgaa gttagattgg gttttttaaga gtagttttta aaatacggat  99420
aaataccagt tgttggagtt ttgtttaaag ttctttaact tcttatttt gggccaaaat    99480
acaggtatac gctagaaatg attttttaaca caggtcattt atgccaaact gcattttgcc  99540
ttaattttt tttttttt tttttttgag agggagtctc actcattgcc caagctggag      99600
tgcaatggca cgatctcggc tcacttacaa cctccacctc ccaggttcaa gcgattctcc   99660
tgcctcagcc tcctgagtag ctgggattac aggcacctgc ctggctaatt tttgtatttt   99720
tagtggagac ggggtttcac catgttggcc aggctggtct cgaactgctg acctcaggtg   99780
atccacccgc cttggcctcc caaagtgcgg ggattacagg tgtgagccac cgtgcttggc   99840
caaaattttt attaattttt ctattgcctg gactctgtga acctatccat tttgccttt    99900
aaaaatactt aggtgtaaat atagatattc attaactcag cattgtttta atctatattt   99960
ccaaaggcaa tttaaaagat cagaaaataa gaccaaatta atataaaaat gcatacttta  100020
ggctgggcaa agtggctcac gtctgtaatc ccagcacttt gggaggccaa ggtgggcgga  100080
tcacctgagg ttaggagttc aggaccaacc tggccatcat ggcgaaaccc tgtctctact  100140
aaaaatacaa aaattagctg ggcatggagg catgtgcctg taatcccagc tactcgggag  100200
gctgagacag aagaattgct tgaaccttgg aggggaggt tgcatatctg agtggtgaaa   100260
ttgtgattct ttttttctct ttgtctgtat ttttgaactt ttctataaat gattgtgttt  100320
tgtttttata ttggaaaaat attatgcttt caaatgttaa tacctatgaa actaaacaca  100380
agtaataaat atattagtat agcatttatt aaggtttctt gtgtagcaga tcaacataga  100440
aaatatattt aaatggctga cataattttc taagaataca tacacgtata tttttttataa 100500
cattaagaaa cagcagcatc attactttaa tccatcattt cgttaaccac catatacctg  100560
ttgatcattt gtattgtcat gtgctttta aaaatctaga tgagaaatat tcgattatct   100620
gacttcactg aatccttgaa aaaaataaaa cgcagcgtca gccctcaaac tttagaagcg  100680
tacatacgtt ggaacaagga cttttggagat accactgttt aaggaaatac ctttgtaaac 100740
ctgcagaaca ttttacttaa aagaggaaac acaagatctt caatgaacgt catcggctac  100800
agaaacagcc taagtttaca ggactttttta gagtcttaca tatttgtgca ccaaacttga  100860
agatgaacca gaaaacagac ttaaacaaaa tatacaatgc aaatgtaatt ttttgttgtt  100920
taaggccttg ccttgatggt cacagttatc ccaatggaca ctaagttaga gcacaacaaa  100980
acctgattct ggtcttcttt accaatataa tcataatgta aataataatt tgtatattgt  101040
gttgcagatg aaagtattcc aggaacagtg aatggtagaa gacacaagaa catttgtttg  101100
tttgtcttct gatgtttttt cttaaaatag taatttctcc tactttttctt ttctactgtt 101160
gtcttaacta caggtgattg gaatgccaaa cactcttaag tttatttct tttttcgttt    101220
tataaattca gtgtgccaaa tgaaactttt ttcctaagta actgtaatag gaaaagttt    101280
attttgagag tttcttcttc ataaatctac agacattaaa caattgttgt gttcttttta  101340
cctttatttt ttctattacc ttgctaccaa acagtttaga tagcaatata atagcaaaaa  101400
agcaaatatg gtaaaataga gaaggtttga aggtttgagt tactctgtca tataacatgt  101460
agatcagtct tcatgtgacc tgcagtattt ttttttctaa tgtatttgtc agaaatctgt  101520
tgtagactgt taacttcttc ctgatggaat ttattttctg caagaattat tctgatattt  101580
aagagagcca atttaactg ctgtgaaaat gtttccagtg caagagaagg gaaatactag   101640
```

```
gaactaagac atttctaatt tattgcttat tactttctta attttacagg ataattataa    101700
gcaagtggaa ctaccatctt ttattcttaa taattattaa tcccttcaat gaaactttaa    101760
aaaaactgaa tttttataca tggcatacat ttttctagtt ccttctgctt gctttattaa    101820
ctcaaaagtt ctagttctag tctgttgatc tgccttttgt tctcccaaaa tgtacagtaa    101880
ttccatttgt ttgtataaat atgcctggat tttcattata aaaatgtcat tgtagggagt    101940
agagactcat atcatggcct tttaaatatt gtaataaagg caaatagata tttgcccttta   102000 gtttactggt taaaagtttg tttacagaac ttttctctgg tgcttaaatg atgctatgta    102060
aaatgtcatg agtggaaaga atatttgtag tagtaacaag aattttttcat ttaggaaaga   102120 tttcttaggt tttgaaagaa tacattaaaa taaaaaactt gccctacta ggtaagaact     102180 ttataatgaa gacatacatt cttcttaatt ttactcttgc tcttgttaaa gatttgtttg    102240
aatatagaag atgcatgatt tctgggtttt tttttttttt tgagacagag tttcgctctt    102300
gttgcccagg ctggagtgca atggcgcaat ctcgactcac acaacctcc gcctcccagg     102360 ttcaagcaat tctcctgcct cagcctcccg agtagctggg attacaggca tgcgccacta    102420
ccccagctaa ttttgtattt ttagtagaga tggggtttct ccatgttggt caggctggtc    102480
ttgaactcct gacctcaggt gatccgcctg cctcggcctc ccaaagtgct gggattacag    102540
gcataagcca ctgcgcccag ccagaagatg catgatttct taggatcata tgctgtttgt    102600
agccataagg taaatcatgt ctcttccaat catgactttg gaactccctg aataataaaa    102660
atgagagttg agataaatag gggaaaaaaa attttttttca agccagagct atgcatatgt    102720
taggtgatgg gtagtatccc tttaaggtct caaacattac aacatcaatt atgaaatact    102780
gataacgaaa ggtagtaatg aaatatatat gatgaaaaga attgagaagt tctaaattaa    102840
gacatttcag ttaagctcat aaaatttcat tgttttcatt taaaagatta acgttattga    102900
tacttggata actggctaat catattaaag gactatgtgg ttccagctca acttttaata    102960
tattgtctcc tttaaaacta tcatggttat aattctattg ggaaagactt ttagataaca    103020
aagatttcaa atgttaaaag agataaaagt caggttaata ctatcttaaa cactgagtca    103080
gaaaatcatt actgtataga agttgctttc ctgatcaagt ctgaacttca gctagtgcta    103140
gagaactatt ttctatgact taactctaac caagttttat tttaagctgt ttctttgata    103200
gaagggccat gaaaatagag taatgatata gtaggagata agggattggt ttggtctttt    103260
tcaataaaga tagaagttgc tgaagttttc tgaattaata atgacttaga ttgtgacctt    103320
ttagattcgg tgttgagctc tgtgttgtat tacttcctaa aagataatgc ttaaacatta    103380
agcattagtg tgctcttcat gttaatatgg cagagttttg taaactaaat taaaacttac    103440
tgatatattg gactttgagc caagggaaag aatgagtact atctttccag atatcttaag    103500
ggtaaaagct tattctaaga cagtctgtcc attgagaata ttagatttct gacttgcaaa    103560
tatgtttgta ctccagaaga attagaggaa aagcagatac tagaattcta atttaattac    103620
atatacagcc gtctttgttt atagtgtaga attctttata ttttgtacaa aaactaattc    103680
ttttggtaaa atgaaccatt tacagttcgg ttttggactc tgagtcaaag gattttcctt    103740
taaatgcttg tctcaatttt agtctggtct tttgtacttt tcttcagaag aaatgaatta    103800
aagggtacag ttgcataaag tgggttttta tcctaatgta ttggaaataa atgataaact    103860 ttatttgtc tttactttt tactttaaa cttttgata ttttaggggt tggagtctga       103920
taatgaagga gttgtgtgta ttggactctt agtaacaatt ataaacgctt aacaaaatat    103980
agaaagcaat gattgggtgg ctctgcagag caatcaaaac aaggtagaaa ctgcaaagtc    104040
```

```
ctataatgga agagattcag gctgggtgtg gtggctcatg cctgtttggg aggccagtat   104100
gggagaatcg cttacactca ggaattcaag accagcctgg ggaatatagg gagaccctgt   104160
ttctgccaaa aaaaaaaaaa aaaaaaaaac taaactaaaa attagccagg tttggtggcc   104220
tacacctgta gtcccggtta ctcaagaggc tgaggttaga ggatcgctta agcccgggag   104280
gaggaggttg cagtgagcca agatcacacc accacactcc agcccaggtt acagagaacc   104340
tgtctcaaaa aataaaaagt aaacgagatt caccttaacc agcttttacc cataaggcaa   104400
tttccagttt gtgcagttca cttggatata gaattcaggt agaatgtgac agttttgaca   104460
ggctgaggaa tcatttggga cttctagaac acctgaaaat tagaagagaa attttgggaa   104520
ggagagtgcc tcagaaagta agctctaaaa tctgcctaca tattcctttc aaatccttgg   104580
tggattccaa aattgtgctg gtgcagtgtg attatttaaa ggaacccagg agaaagcaag   104640
ttaaagtcta aaaactcag cagcgattgc agctgcccaa ggacagagag tttgaaattc   104700
aagttccact aagaaggact gagtaaatac ttggtgtttc ccattgaacc cccaaaatgc   104760
cacgccttaa ggaagaatga cagcatccta gaactaaagg ctgtgcttca gcactaagga   104820
caaaatggaa ataaacttac tgtaatgaag cttaaaatca aatctcacag catcaaggtt   104880
atccattagt aatttaaaac cagaacaaaa cacagcattc ttgagaagaa acaattcag   104940 tcatcacagc atatatccaa agctcagtac ataataaaca gttactaagc atgcaaagaa   105000
aaattatgtg atccttttga ctcaacttcc ctgatggaaa aaaaaagtg gtccatacca   105060 tactcaacag aaaatataca gaagcagatg cacaagtgac ctctatgaga gtgattttaa   105120
aatagcgtta aaatatgtta aaagaattta caagaagaga taatgggtga atagataggg   105180
agtttcagca gaaaaataag aattgaaaac ccaacgagg ccaggcaccg tgcctcacgc   105240
ccgtaatcac agcactttgg gaggccaagg caggtggatc acctaaggtc aggagttcaa   105300
gaccagcctg accaacatgg tgaaacccgg tctctactaa aaatacaaaa ctagccgggc   105360
atgggtgatg catgcccata atcctagcta cttgggaggc tgaagcagga gaattgcttg   105420
aacctgggag gtagaggttg cagtgaacca agatcatgcc attgcactcc agcctgggca   105480
agaagagcaa aactccatct caaaaaataa taataataat tggctgggcg cggtggctca   105540
cgcctgtaat cccagcactt tgggaggccg agacaggcag atcacaaggt caggagattg   105600
agaccatcct ggctaacatg gtgaaacccc gtctctacta aaaatacaaa aaattagcct   105660
ggcatggtgg cgggcacctg tagtcccagc tactcgggag gctgaagcag gagaatggca   105720 tgacccagg aggcggaact tgcaatgagc ccagatcgcg ccactgcact ccagcctggg   105780
caaccgtctc aaaaataata ataataataa ttagaaaata ataaaaaata acccactgga   105840
aagtcttgta atgaaaacta cagtatctga aattaaaaat ttaaatggat ggacttaaca   105900
gtaaactagg cacaacagga aagactgaaa aagacaagta agtatcaaac caaagcagag   105960
agagaaagaa aaagaaaata gcagaggttt gagacctttg gaacattatc agttcctgta   106020
atttgaagta aagaaggaaa ggaagagaat ggggcaagag aaatctttga agcaatgatg   106080
cgtgaaattt tccccaaagt gttgaaagac atcaacgtac agatctaaga agttcactga   106140
atccccaagc agaataaata caacaaagac tacatctggg tacatcacat tgccaaaaaa   106200
aaaaaaaaaa aaaatcttaa aagcaatcaa ggtgggagt gggaaggagt agcattacat   106260
tcagataaac aagagtgatg gctaacctca tcagaaatga tggaattaag aaaatgatgg   106320
aatgacatct ttaaggtgca aagatgaaac aaaggttaac ttaaaactct gtatccagtt   106380
```

-continued

```
aaaatatcct tcaagatgtt aaggcaatgg ccaggctcag tggcttatgc ctgtaatccc 106440
aacactttgg ggggctgaga caggagaatc ccttgaggcc atgagtgacc agcctgggca 106500
acctagtgag aaccccatca aaaataaaa ttagctgggc atgggctgtg gtcgtgctac 106560
tgcactccag cctgggggac agagtcccta tctcttgaaa aacttaagac aaaatctttt 106620
ccagatgaaa acagaatttg ttgctggcag actgacttta tacggaatgc tttaagaaat 106680
tcttcaggct gaaggaaaat ataaatctgg agtgaaaaac gtagtatctg aaattaaaat 106740
tttccttgga tggacttatc agtaaatgga tttcccaatg ggaacctgta tctccaggat 106800
ggaattaaga attttgaaat gataaacatg ttggtaaata agaaagacat ttttcttttt 106860
tatttttcta aatatcattg ctgtttaaag caaacaaaaa tagtattgca gtgtttataa 106920
tatatgtata agtaaaatat aggacagaaa tagcatgaag ggtcagagag ggcaataaat 106980
gtaattatat tgagataata ttactatatt gtacacaaag tgagatagca ttagtgtaag 107040
gtagattgtg ataagaatgc attttgtaat ctctcacccc atcactgggg tgcagtagat 107100
ctaaaaagcc attagagaag ataaaatggg tcactaagaa ttatgtgatt agtcaaatga 107160
aatcaaggaa agaaaacag agcaaagaag tgtaagataa aacagtggga tggaagagct 107220
gaaattaata atgtcactaa attgcttacc ttcctccttc ctgaactgtt gtggattttt 107280 ttttttttcag ggggttgagg ttttttttta gagacagagt ctctattgcc ccaggctgga 107340
cagcagtggc gtaatcagtc tcaaaatccc tgcagtctca aactcctggg ctcaagtgat 107400
cctcctgcct cggcctccca aaatgctggg attacaggca ggcagagcca ccacccctg 107460 ccagaactat tgttttaaag tcattaggtg gttaagccct cgagactatg tgcaagtttg 107520
atgattcgtt aggagcactc acaggactca gcatatagtc ttattcccaa caatgattta 107580
ttagagcaaa aggatatgaa gcaaattcag caaagggaaa aaaggaatta agtgaagtcc 107640
agaggaaacc aagcaccagc ttctaagggt tctctcctaa tgaagtcaca caggatgtca 107700
ctccagcaac aagtgacagc atgtgaaagt gttaagcctc actgttagac atagtaagct 107760
tgttagggaa tagagggaat ctcccctcaa attcaagttc ccagatgcct ggcaagggcc 107820
aaccttgcca gcaggacttt ctggggatag cagtcccagg cacgtgtttg cacagtggtt 107880
cagatcaatg tgcttacatt gggtagaggg gacctatgga agtccaaatt tgggtgtcag 107940
agacctaata gggtgaagac agtgtctaca atgatggaca gctaggtatg aggtgtcagg 108000
gacagattga ggcagttatt cacatggtgg atagggcaa cctggaatga ggaataagct 108060
caagcacaga aaggggtgtc catatgggt aagggtgtca gcagagatgg tagattggtt 108120
gcacaccaaa gacttgatgg aataaagtga atatactaac cacagagaag gtaattataa 108180
atacagaaag gggggaaact agaatgaaac ctggagttca gcttgaattg ggtttaagaa 108240
agtgaattca tggtttaaaa tctataaaaa tagatgaaat atcggctggg cacagtggct 108300
cacgcatata atcccagcac tttgggaggc cgaggcgggc agatcgcttg agatcaggag 108360
tttgagacca gcctggccaa cactgcgaaa ccccatctct agtaaaaata caaaaattag 108420
ccaggtgtgg tggtacacac ctgtagtccc agctacttgg gaggctgagg cacgagaatc 108480
acttgaacct gggaggcaga ggttgcagtg ggctgagatc gcaccactgc actccagcct 108540
gggcaacaga gcgagatcct gcctcaaata aaaatagagg acatataagc atataaatat 108600
acacgtgtgt atgtgtccaa atatgtatat tccctagtct gtccaccaag gtggccttgg 108660
agcagttatg ctccaataat aatgagcaca taaagtaccc atatcttgcc ttccaaattc 108720
ttcactgtct tagtctgctt gggctgcatt acaaaatacc atagactggg cagcttaaat 108780
```

```
aacagaaatt tatcctcaca gttctagaag cttggaagtc caagattaaa gtaccagcca   108840
gtttggtttc tagtgagggc tttcttcctg gcttgcagat ggccaccttc tcaccgtgtc   108900
cttgtatggc agacagcaca agctctctgg tgtccctttt taaaagggca ttaatcccat   108960
catgacagtc ccatcctcat tatctcatct aaccctaggt acttcccaaa ggctgaatca   109020
ccaaagacca tcacattgct ggtgaaggct tcaacatatg aatttgaggg acacgaatat   109080
tcagtccata acatcaacta aaggaaccaa gactctttga taaaatggct aaattcaggg   109140
ctggggcaga gaaatacat gagtgtggaa cttcttgtgc cagagagaaa aagtgcccaa   109200
agattgatga ggatgaatca ttgaaatgac acacagatta aaagggttcc cactggacaa   109260
atttgagcat caaataagt aatagtagta attaattata acccatcaga agaaataaac   109320
catgagctca tgtgaatata tgaatacaaa cataaacaaa ttacaagcat aatgaggaat   109380
gtgatattta tatggtttaa aggtacctct ccaggccggg tgcagtaact ctcacctgta   109440
atcccagcac tttgggaggc caaggcaggt agatcacctg aggtcaggca tttgagacca   109500
gcctgcacaa catggtgaaa ccctgactct actaaaaata cataacgcga gccgggcgtg   109560
gtggcacgtg tctataatct gccactgatt aggtgtgtga ttttcccaag cagggggataa   109620
tagtagtacc tatgtcaaag gctgttatga ggattaaatg agctaacaca taatcgtgct   109680
tttttttttt tttttttttt ttgagacaga gtcttgcact gtcgcctggg ctggagtgca   109740
atggcacgat ctcggcccac tgcaacctct gcctcccagg ttcaagtgat tctcctgcct   109800
cagcctcctg agtagctggg attacaggct cctgccacca cacctggcta ttttcaatag   109860
agacggggtt tcactatgtt ggccaggcta gtctcaaaaa cctgacctcg tgatccaccc   109920
gctttggcct cccaaagtgc tgggattaca ggcatgagcc actgcacccg ctttttttt    109980
tttttttttg agatggaatc                                               110000
```

<210> SEQ ID NO 2
<211> LENGTH: 3263
<212> TYPE: DNA
<213> ORGANISM: Homo sapiens
<400> SEQUENCE: 2

```
gctcctgaga ccggcgggca cacggggtc tgtggccccc gccgtagcag tggctgccgc     60
cgtcgcttgg ttcccgtcgg tctgcgggag gcgggttatg gcggcggcgg cagtgagagc   120
tgtgaatgaa ttctccgggt ggacgaggga agaagaaagg ctccggcggc gccagcaacc   180
cggtgcctcc caggcctccg ccccttgcc tggcccccgc cctcccgcc gccgggccgg     240
cccctccgcc cgagtcgccg cataagcgga acctgtacta tttctcctac ccgctgtttg   300
taggcttcgc gctgctgcgt ttggtcgcct tccacctggg gctcctcttc gtgtggctct   360
gccagcgctt ctcccgcgcc ctcatggcag ccaagaggag ctccggggcc gcgccagcac   420
ctgcctcggc ctcggccccg cgccggtgc cgggcggcga ggccgagcgc gtccgagtct   480
tccacaaaca ggccttcgag tacatctcca ttgccctgcg catcgatgag gatgagaaag   540
caggacagaa ggagcaagct gtggaatggt ataagaaagg tattgaagaa ctggaaaaag   600
gaatagctgt tatagttaca ggacaaggtg aacagtgtga aagagctaga cgccttcaag   660
ctaaaatgat gactaatttg gttatggcca aggaccgctt acaacttcta gagaagatgc   720
aaccagtttt gccattttcc aagtcacaaa cggacgtcta taatgacagt actaacttgg   780
catgccgcaa tggacatctc cagtcagaaa gtggagctgt tccaaaaaga aaagacccct   840
```

```
taacacacac tagtaattca ctgcctcgtt caaaaacagt tatgaaaact ggatctgcag      900
gcctttcagg ccaccataga gcacctagtt acagtggttt atccatggtt tctggagtga      960
aacagggatc tggtcctgct cctaccactc ataagggtac tccgaaaaca ataggacaa      1020 ataaaccttc taccoctaca actgctactc gtaagaaaaa agacttgaag aattttagga     1080
atgtggacag caaccttgct aaccttataa tgaatgaaat tgtggacaat ggaacagctg     1140
ttaaatttga tgatatagct ggtcaagact tggcaaaaca agcattgcaa gaaattgtta     1200
ttcttccttc tctgaggcct gagttgttca cagggcttag agctcctgcc agagggctgt     1260
tactctttgg tccacctggg aatgggaaga caatgctggc taaagcagta gctgcagaat     1320
cgaatgcaac cttctttaat ataagtgctg caagtttaac ttcaaaatac gtgggagaag     1380
gagagaaatt ggtgagggct cttttgctg tggctcgaga acttcaacct tctataattt      1440
ttatagatga agttgatagc cttttgtgtg aagaagaga aggggagcac gatgctagta     1500
gacgcctaaa aactgaattt ctaatagaat ttgatggtgt acagtctgct ggagatgaca     1560
gagtacttgt aatgggtgca actaataggc cacaagagct tgatgaggct gttctcaggc     1620
gtttcatcaa acgggtatat gtgtctttac caaatgagga gacaagacta cttttgctta     1680
aaaatctgtt atgtaaacaa ggaagtccat tgacccaaaa agaactagca caacttgcta     1740
gaatgactga tggatactca ggaagtgacc taacagcttt ggcaaaagat gcagcactgg     1800
gtcctatccg agaactaaaa ccagaacagg tgaagaatat gtctgccagt gagatgagaa     1860
atattcgatt atctgacttc actgaatcct tgaaaaaaat aaaacgcagc gtcagccctc     1920
aaactttaga agcgtacata cgttggaaca aggactttgg agataccact gtttaaggaa     1980 ataccttgt aaacctgcag aacatttac ttaaaagagg aaacacaaga tcttcaatga      2040
acgtcatcgg ctacagaaac agcctaagtt tacaggactt tttagagtct tacatatttg     2100
tgcaccaaac ttgaagatga accagaaaac agacttaaac aaaatataca atgcaaatgt     2160
aattttttgt tgtttaaggc cttgccttga tggtcacagt tatcccaatg gacactaagt     2220
tagagcacaa caaaacctga ttctggtctt ctttaccaat ataatcataa tgtaaataat     2280
aatttgtata ttgtgttgca gatgaaagta ttccaggaac agtgaatggt agaagacaca     2340
agaacatttg tttgtttgtc ttctgatgtt ttttcttaaa atagtaattt ctcctacttt     2400
tcttttctac tgttgtctta actacaggtg attggaatgc caaacactct taagtttatt     2460
ttcttttttc gttttataaa ttcagtgtgc caaatgaaac ttttttccta agtaactgta     2520
ataggaaaaa gtttattttg agagtttctt cttcataaat ctacagacat taaacaattg     2580
ttgtgttctt tttaccttt attttttctat taccttgcta ccaaacagtt tagatagcaa     2640
tataatagca aaaaagcaaa tatggtaaaa tagagaaggt ttgaaggttt gagttactct     2700
gtcatataac atgtagatca gtcttcatgt gacctgcagt attttttttt ctaatgtatt     2760
tgtcagaaat ctgttgtaga ctgttaactt cttcctgatg gaatttattt tctgcaagaa     2820
ttattctgat atttaagaga gccaatttta actgctgtga aatgtttcc agtgcaagag      2880 aaggaaata ctaggaacta agacatttct aatttattgc ttattacttt cttaatttta      2940
caggataatt ataagcaagt ggaactacca tctttattc ttaataatta ttaatccctt      3000
caatgaaact ttaaaaaaac tgaatttta tacatggcat acatttttct agttccttct     3060
gcttgcttta ttaactcaaa agttctagtt ctagtctgtt gatctgcctt tgttctccc      3120 aaaatgtaca gtaattccat ttgtttgtat aaatatgcct ggattttcat tataaaaatg     3180
tcattgtagg gagtagagac tcatatcatg gcctttttaaa tattgtaata aaggcaaata    3240
```

-continued gatatttgcc cttagtttac tgg                                              3263

<210> SEQ ID NO 3
<211> LENGTH: 616
<212> TYPE: PRT
<213> ORGANISM: Homo sapiens

<400> SEQUENCE: 3

Met Asn Ser Pro Gly Gly Arg Gly Lys Lys Gly Ser Gly Gly Ala
1               5                   10                  15

Ser Asn Pro Val Pro Pro Arg Pro Pro Pro Cys Leu Ala Pro Ala
                20                  25                  30

Pro Pro Ala Ala Gly Pro Ala Pro Pro Glu Ser Pro His Lys Arg
                35                  40                  45

Asn Leu Tyr Tyr Phe Ser Tyr Pro Leu Phe Val Gly Phe Ala Leu Leu
            50              55                  60

Arg Leu Val Ala Phe His Leu Gly Leu Leu Phe Val Trp Leu Cys Gln
65                  70                  75                  80

Arg Phe Ser Arg Ala Leu Met Ala Ala Lys Arg Ser Ser Gly Ala Ala
                85                  90                  95

Pro Ala Pro Ala Ser Ala Ser Ala Pro Ala Val Pro Gly Gly Glu
                100                 105                 110

Ala Glu Arg Val Arg Val Phe His Lys Gln Ala Phe Glu Tyr Ile Ser
                115                 120                 125

Ile Ala Leu Arg Ile Asp Glu Asp Glu Lys Ala Gly Gln Lys Glu Gln
130                 135                 140

Ala Val Glu Trp Tyr Lys Lys Gly Ile Glu Glu Leu Glu Lys Gly Ile
145                 150                 155                 160

Ala Val Ile Val Thr Gly Gln Gly Glu Gln Cys Glu Arg Ala Arg Arg
                165                 170                 175

Leu Gln Ala Lys Met Met Thr Asn Leu Val Met Ala Lys Asp Arg Leu
                180                 185                 190

Gln Leu Leu Glu Lys Met Gln Pro Val Leu Pro Phe Ser Lys Ser Gln
                195                 200                 205

Thr Asp Val Tyr Asn Asp Ser Thr Asn Leu Ala Cys Arg Asn Gly His
                210                 215                 220

Leu Gln Ser Glu Ser Gly Ala Val Pro Lys Arg Lys Asp Pro Leu Thr
225                 230                 235                 240

His Thr Ser Asn Ser Leu Pro Arg Ser Lys Thr Val Met Lys Thr Gly
                245                 250                 255

Ser Ala Gly Leu Ser Gly His His Arg Ala Pro Ser Tyr Ser Gly Leu
                260                 265                 270

Ser Met Val Ser Gly Val Lys Gln Gly Ser Gly Pro Ala Pro Thr Thr
                275                 280                 285

His Lys Gly Thr Pro Lys Thr Asn Arg Thr Asn Lys Pro Ser Thr Pro
                290                 295                 300

Thr Thr Ala Thr Arg Lys Lys Lys Asp Leu Lys Asn Phe Arg Asn Val
305                 310                 315                 320

Asp Ser Asn Leu Ala Asn Leu Ile Met Asn Glu Ile Val Asp Asn Gly
                325                 330                 335

Thr Ala Val Lys Phe Asp Asp Ile Ala Gly Gln Asp Leu Ala Lys Gln
                340                 345                 350

Ala Leu Gln Glu Ile Val Ile Leu Pro Ser Leu Arg Pro Glu Leu Phe
                355                 360                 365

```
Thr Gly Leu Arg Ala Pro Ala Arg Gly Leu Leu Phe Gly Pro Pro
    370                 375                 380

Gly Asn Gly Lys Thr Met Leu Ala Lys Ala Val Ala Ala Glu Ser Asn
385                 390                 395                 400

Ala Thr Phe Phe Asn Ile Ser Ala Ala Ser Leu Thr Ser Lys Tyr Val
                405                 410                 415

Gly Glu Gly Glu Lys Leu Val Arg Ala Leu Phe Ala Val Ala Arg Glu
                420                 425                 430

Leu Gln Pro Ser Ile Ile Phe Ile Asp Glu Val Asp Ser Leu Leu Cys
            435                 440                 445

Glu Arg Arg Glu Gly Glu His Asp Ala Ser Arg Arg Leu Lys Thr Glu
        450                 455                 460

Phe Leu Ile Glu Phe Asp Gly Val Gln Ser Ala Gly Asp Asp Arg Val
465                 470                 475                 480

Leu Val Met Gly Ala Thr Asn Arg Pro Gln Glu Leu Asp Glu Ala Val
                485                 490                 495

Leu Arg Arg Phe Ile Lys Arg Val Tyr Val Ser Leu Pro Asn Glu Glu
                500                 505                 510

Thr Arg Leu Leu Leu Lys Asn Leu Leu Cys Lys Gln Gly Ser Pro
        515                 520                 525

Leu Thr Gln Lys Glu Leu Ala Gln Leu Ala Arg Met Thr Asp Gly Tyr
        530                 535                 540

Ser Gly Ser Asp Leu Thr Ala Leu Ala Lys Asp Ala Ala Leu Gly Pro
545                 550                 555                 560

Ile Arg Glu Leu Lys Pro Gln Val Lys Asn Met Ser Ala Ser Glu
                565                 570                 575

Met Arg Asn Ile Arg Leu Ser Asp Phe Thr Glu Ser Leu Lys Lys Ile
                580                 585                 590

Lys Arg Ser Val Ser Pro Gln Thr Leu Glu Ala Tyr Ile Arg Trp Asn
        595                 600                 605

Lys Asp Phe Gly Asp Thr Thr Val
    610                 615

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
cggagctcct cttggctgcc atg                                              23

<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5
agaagcgctg gcagagccac acgaag                                           26

<210> SEQ ID NO 6
<211> LENGTH: 27
<212> TYPE: DNA
<213> ORGANISM: Artificial sequence
<220> FEATURE:
```

```
<223> OTHER INFORMATION: Primer

<400> SEQUENCE: 6
aaggcgacca aacgcagcag cgcgaag                                27

<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
aggagcaagc tgtggaatgg tataag                                 26

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
tggttatggc caaggaccgc ttacaac                                27

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
caaacggacg tctataatga cagtac                                 26

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10
ttaggaatgt ggacagcaac cttgc                                  25

<210> SEQ ID NO 11
<211> LENGTH: 25
<212> TYPE: DNA
<213> ORGANISM: Artificial sequence
<220> FEATURE:
<223> OTHER INFORMATION: Primer

<400> SEQUENCE: 11
cttctctgag gcctgagttg ttcac                                  25

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
tgctagaatg actgatggat actcagg                                27
```

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
agatgcagca ctgggtccta tccg                                    24

<210> SEQ ID NO 14
<211> LENGTH: 26
<212> TYPE: DNA
<213> ORGANISM: Artificial sequence
<220> FEATURE:
<223> OTHER INFORMATION: Primer

<400> SEQUENCE: 14
atgaacgtca tcggctacag aaacag                                  26

<210> SEQ ID NO 15
<211> LENGTH: 19
<212> TYPE: DNA
<213> ORGANISM: Artificial sequence
<220> FEATURE:
<223> OTHER INFORMATION: Primer

<400> SEQUENCE: 15
tagcagtggc tgccgccgt                                          19

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
aagcggtcct tggccataac                                         20

<210> SEQ ID NO 17
<211> LENGTH: 19
<212> TYPE: DNA
<213> ORGANISM: Artificial sequence
<220> FEATURE:
<223> OTHER INFORMATION: Primer

<400> SEQUENCE: 17
ggcggcagtg agagctgtg                                          19

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
ctagctcttt cacactgttc                                         20

<210> SEQ ID NO 19
<211> LENGTH: 20
<212> TYPE: DNA
<213> ORGANISM: Artificial sequence
<220> FEATURE:
<223> OTHER INFORMATION: Primer

```
<400> SEQUENCE: 19
aacaggcctt cgagtacatc                                               20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
ctgtgaacaa ctcaggcctc                                               20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
atgagaaagc aggacagaag                                               20

<210> SEQ ID NO 22
<211> LENGTH: 18
<212> TYPE: DNA
<213> ORGANISM: Artificial sequence
<220> FEATURE:
<223> OTHER INFORMATION: Primer

<400> SEQUENCE: 22
tgccaagtct tgaccagc                                                 18

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
ctacaactgc tactcgtaag                                               20

<210> SEQ ID NO 24
<211> LENGTH: 19
<212> TYPE: DNA
<213> ORGANISM: Artificial sequence
<220> FEATURE:
<223> OTHER INFORMATION: Primer

<400> SEQUENCE: 24
cagtgctgca tcttttgcc                                                19

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
taggaatgtg gacagcaacc                                               20

<210> SEQ ID NO 26
<211> LENGTH: 20
```

```
<212> TYPE: DNA
<213> ORGANISM: Artificial sequence
<220> FEATURE:
<223> OTHER INFORMATION: Primer

<400> SEQUENCE: 26
aaagctgtta ggtcacttcc                                          20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tggagatgac agagtacttg                                          20

<210> SEQ ID NO 28
<211> LENGTH: 19
<212> TYPE: DNA
<213> ORGANISM: Artificial sequence
<220> FEATURE:
<223> OTHER INFORMATION: Primer

<400> SEQUENCE: 28
ctggaatact ttcatctgc                                           19

<210> SEQ ID NO 29
<211> LENGTH: 19
<212> TYPE: DNA
<213> ORGANISM: Artificial sequence
<220> FEATURE:
<223> OTHER INFORMATION: Primer

<400> SEQUENCE: 29
atgaggctgt tctcaggcg                                           19

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
gtgagccgaa ctgcacattg                                          20

<210> SEQ ID NO 31
<211> LENGTH: 21
<212> TYPE: DNA
<213> ORGANISM: Artificial sequence
<220> FEATURE:
<223> OTHER INFORMATION: Primer

<400> SEQUENCE: 31
caaagtcgac agctacagtg c                                        21

<210> SEQ ID NO 32
<211> LENGTH: 20
<212> TYPE: DNA
<213> ORGANISM: Artificial sequence
<220> FEATURE:
<223> OTHER INFORMATION: Primer

<400> SEQUENCE: 32
```

| | |
|---|---|
| ggaactgtag ttgagtggga | 20 |

<210> SEQ ID NO 33
<211> LENGTH: 19
<212> TYPE: DNA
<213> ORGANISM: Artificial sequence
<220> FEATURE:
<223> OTHER INFORMATION: Primer

<400> SEQUENCE: 33

| | |
|---|---|
| agatgaggct ccgacctac | 19 |

<210> SEQ ID NO 34
<211> LENGTH: 20
<212> TYPE: DNA
<213> ORGANISM: Artificial sequence
<220> FEATURE:
<223> OTHER INFORMATION: Primer

<400> SEQUENCE: 34

| | |
|---|---|
| aatgccacac ttgtaatctc | 20 |

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35

| | |
|---|---|
| tgtgaatata tcataatttg gg | 22 |

<210> SEQ ID NO 36
<211> LENGTH: 19
<212> TYPE: DNA
<213> ORGANISM: Artificial sequence
<220> FEATURE:
<223> OTHER INFORMATION: Primer

<400> SEQUENCE: 36

| | |
|---|---|
| tacagcagtt ctcatgatg | 19 |

<210> SEQ ID NO 37
<211> LENGTH: 21
<212> TYPE: DNA
<213> ORGANISM: Artificial sequence
<220> FEATURE:
<223> OTHER INFORMATION: Primer

<400> SEQUENCE: 37

| | |
|---|---|
| gaccaaattg gtgcatgcat g | 21 |

<210> SEQ ID NO 38
<211> LENGTH: 20
<212> TYPE: DNA
<213> ORGANISM: Artificial sequence
<220> FEATURE:
<223> OTHER INFORMATION: Primer

<400> SEQUENCE: 38

| | |
|---|---|
| acatttccaa tacatcccac | 20 |

<210> SEQ ID NO 39
<211> LENGTH: 20
<212> TYPE: DNA
<213> ORGANISM: Artificial sequence

```
<220> FEATURE:
<223> OTHER INFORMATION: Primer

<400> SEQUENCE: 39
atttgtcatt tcacatgcac                                              20

<210> SEQ ID NO 40
<211> LENGTH: 20
<212> TYPE: DNA
<213> ORGANISM: Artificial sequence
<220> FEATURE:
<223> OTHER INFORMATION: Primer

<400> SEQUENCE: 40
ttagaatgac tatacctgac                                              20

<210> SEQ ID NO 41
<211> LENGTH: 18
<212> TYPE: DNA
<213> ORGANISM: Artificial sequence
<220> FEATURE:
<223> OTHER INFORMATION: Primer

<400> SEQUENCE: 41
tcaggttaag taagactc                                                18

<210> SEQ ID NO 42
<211> LENGTH: 19
<212> TYPE: DNA
<213> ORGANISM: Artificial sequence
<220> FEATURE:
<223> OTHER INFORMATION: Primer

<400> SEQUENCE: 42
ttcctatcta cctagtgac                                               19

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
ttttatagca agttgccctg                                              20

<210> SEQ ID NO 44
<211> LENGTH: 19
<212> TYPE: DNA
<213> ORGANISM: Artificial sequence
<220> FEATURE:
<223> OTHER INFORMATION: Primer

<400> SEQUENCE: 44
cctatgaaga tcctggtac                                               19

<210> SEQ ID NO 45
<211> LENGTH: 20
<212> TYPE: DNA
<213> ORGANISM: Artificial sequence
<220> FEATURE:
<223> OTHER INFORMATION: Primer

<400> SEQUENCE: 45
tgtcatgatt ctaacaaggg                                              20
```

-continued

<210> SEQ ID NO 46
<211> LENGTH: 20
<212> TYPE: DNA
<213> ORGANISM: Artificial sequence
<220> FEATURE:
<223> OTHER INFORMATION: Primer

<400> SEQUENCE: 46
tctatttcac tcctgacatg                               20

<210> SEQ ID NO 47
<211> LENGTH: 19
<212> TYPE: DNA
<213> ORGANISM: Artificial sequence
<220> FEATURE:
<223> OTHER INFORMATION: Primer

<400> SEQUENCE: 47
gtcatagggc ttaggcttc                                19

<210> SEQ ID NO 48
<211> LENGTH: 20
<212> TYPE: DNA
<213> ORGANISM: Artificial sequence
<220> FEATURE:
<223> OTHER INFORMATION: Primer

<400> SEQUENCE: 48
atcatactac ccacttttcc                               20

<210> SEQ ID NO 49
<211> LENGTH: 20
<212> TYPE: DNA
<213> ORGANISM: Artificial sequence
<220> FEATURE:
<223> OTHER INFORMATION: Primer

<400> SEQUENCE: 49
tgtttgggaa gatgctactg                               20

<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ctactgaaga taacgtacat g                             21

<210> SEQ ID NO 51
<211> LENGTH: 20
<212> TYPE: DNA
<213> ORGANISM: Artificial sequence
<220> FEATURE:
<223> OTHER INFORMATION: Primer

<400> SEQUENCE: 51
cattgattgc catgtattgg                               20

<210> SEQ ID NO 52
<211> LENGTH: 20
<212> TYPE: DNA
<213> ORGANISM: Artificial sequence
<220> FEATURE:
<223> OTHER INFORMATION: Primer

<400> SEQUENCE: 52
agaaggccag aaatactcag                                              20

<210> SEQ ID NO 53
<211> LENGTH: 22
<212> TYPE: DNA
<213> ORGANISM: Artificial sequence
<220> FEATURE:
<223> OTHER INFORMATION: Primer

<400> SEQUENCE: 53
gtacttaaat cggtaaatat gg                                           22

<210> SEQ ID NO 54
<211> LENGTH: 20
<212> TYPE: DNA
<213> ORGANISM: Artificial sequence
<220> FEATURE:
<223> OTHER INFORMATION: Primer

<400> SEQUENCE: 54
ctcaagtctt aggaatgcag                                              20

<210> SEQ ID NO 55
<211> LENGTH: 20
<212> TYPE: DNA
<213> ORGANISM: Artificial sequence
<220> FEATURE:
<223> OTHER INFORMATION: Primer

<400> SEQUENCE: 55
gcacttaacc aggctgtatg                                              20

<210> SEQ ID NO 56
<211> LENGTH: 19
<212> TYPE: DNA
<213> ORGANISM: Artificial sequence
<220> FEATURE:
<223> OTHER INFORMATION: Primer

<400> SEQUENCE: 56
ctcagatgac tcacatagc                                               19

<210> SEQ ID NO 57
<211> LENGTH: 22
<212> TYPE: DNA
<213> ORGANISM: Artificial sequence
<220> FEATURE:
<223> OTHER INFORMATION: Primer

<400> SEQUENCE: 57
ctttactaga ctaattctcc tg                                           22

<210> SEQ ID NO 58
<211> LENGTH: 20
<212> TYPE: DNA
<213> ORGANISM: Artificial sequence
<220> FEATURE:
<223> OTHER INFORMATION: Primer

<400> SEQUENCE: 58
cagattcaag aagacagatc                                              20

<210> SEQ ID NO 59

```
<211> LENGTH: 20
<212> TYPE: DNA
<213> ORGANISM: Artificial sequence
<220> FEATURE:
<223> OTHER INFORMATION: Primer

<400> SEQUENCE: 59
gcaataattc accacacttg                                              20

<210> SEQ ID NO 60
<211> LENGTH: 20
<212> TYPE: DNA
<213> ORGANISM: Artificial sequence
<220> FEATURE:
<223> OTHER INFORMATION: Primer

<400> SEQUENCE: 60
ggtagttctt gtttctgctc                                              20

<210> SEQ ID NO 61
<211> LENGTH: 20
<212> TYPE: DNA
<213> ORGANISM: Artificial sequence
<220> FEATURE:
<223> OTHER INFORMATION: Primer

<400> SEQUENCE: 61
caagtgtggt gaattattgc                                              20

<210> SEQ ID NO 62
<211> LENGTH: 19
<212> TYPE: DNA
<213> ORGANISM: Artificial sequence
<220> FEATURE:
<223> OTHER INFORMATION: Primer

<400> SEQUENCE: 62
gagctgaaaa gtattcagc                                               19

<210> SEQ ID NO 63
<211> LENGTH: 20
<212> TYPE: DNA
<213> ORGANISM: Artificial sequence
<220> FEATURE:
<223> OTHER INFORMATION: Primer

<400> SEQUENCE: 63
tgcaaaggac atagccagtg                                              20

<210> SEQ ID NO 64
<211> LENGTH: 20
<212> TYPE: DNA
<213> ORGANISM: Artificial sequence
<220> FEATURE:
<223> OTHER INFORMATION: Primer

<400> SEQUENCE: 64
agcctctgga gatagtatgc                                              20

<210> SEQ ID NO 65
<211> LENGTH: 20
<212> TYPE: DNA
<213> ORGANISM: Artificial sequence
<220> FEATURE:
<223> OTHER INFORMATION: Primer

<400> SEQUENCE: 65
```
ctagaacagg ggtcacagtc                     20

<210> SEQ ID NO 66
<211> LENGTH: 18
<212> TYPE: DNA
<213> ORGANISM: Artificial sequence
<220> FEATURE:
<223> OTHER INFORMATION: Primer

<400> SEQUENCE: 66
ttggacttct taaacttc                       18

<210> SEQ ID NO 67
<211> LENGTH: 21
<212> TYPE: DNA
<213> ORGANISM: Artificial sequence
<220> FEATURE:
<223> OTHER INFORMATION: Primer

<400> SEQUENCE: 67
gcagtatgca agaaattgaa c                   21

<210> SEQ ID NO 68
<211> LENGTH: 19
<212> TYPE: DNA
<213> ORGANISM: Artificial sequence
<220> FEATURE:
<223> OTHER INFORMATION: Primer

<400> SEQUENCE: 68
ggcctgtaat tttcttctg                      19

<210> SEQ ID NO 69
<211> LENGTH: 21
<212> TYPE: DNA
<213> ORGANISM: Artificial sequence
<220> FEATURE:
<223> OTHER INFORMATION: Primer

<400> SEQUENCE: 69
gtactgaata gatacatgta g                   21

<210> SEQ ID NO 70
<211> LENGTH: 19
<212> TYPE: DNA
<213> ORGANISM: Artificial sequence
<220> FEATURE:
<223> OTHER INFORMATION: Primer

<400> SEQUENCE: 70
gtgtagcaga tcaacatag                      19

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
catcttcaag tttggtgcac                     20

<210> SEQ ID NO 72
<211> LENGTH: 1689
<212> TYPE: DNA

-continued

```
<213> ORGANISM: Mus musculus
<220> FEATURE:
<223> OTHER INFORMATION: Incomplete Spg4 DNA.

<400> SEQUENCE: 72
aggccgagag cgtccgcgtc ttccacaagc aggccttcga gtacatctcc attgccctgc      60
gcatcgacga ggaagagaaa gcaggacaga aggaacaagc tgtggaatgg tataagaaag     120
gtatcgaaga actggaaaaa ggaatcgctg ttatagttac gggccaaggt gaacagtatg     180
aaagagctag acgtcttcaa gccaaaatga tgactaattt agttatgcc aaggaccgtt      240 tacaacttct agagaagctg caaccagttt tgcaattttc caagtcacag acggacgtct     300
ataacgagag tactaacctg acatgccgca atggacatct ccagtcagaa agtggagcag     360
ttccgaagag gaaagacccc ttaacacatg ctagtaattc attgcctcga tcaaaaactg     420
tcctgaaaag tggctccgca gggctctccg tcaccacag gcgcctagt tgcagtggtt       480 tgtccatggt ttctggagca agaccgggac ctggtcctgc agctaccaca cataagggta    540
ctccaaaacc aaatagaacc aacaaacctt ctactcccac aactgcagtt cggaaaaaga    600
aagacttgaa aaattttagg aatgtggaca gcaatcttgc taaccttata atgaatgaaa    660
ttgttgacaa tgggacagct gttaagtttg atgacatagc cgggcaggag ctggcaaagc    720
aagcgctgca ggagattgtc atccttcctt ctctgcggcc tgagttgttc acagggctca    780
gagctcctgc tagaggcttg ttactcttcg gtccgccagg aaacggaaaa acaatgctgg    840
ctaaagcagt agctgcagag tctaatgcga ccttttttcaa cataagtgct gccagtttaa    900
cttcaaaata tgtgggagaa ggagagaaat tggtgagagc tctctttgct gtggctcgag    960
aacttcaacc atctataatt tttatagatg aagttgacag tcttttgtgt gagagacggg   1020
aaggggagca cgacgctagc agacggctaa agacggaatt tttaatagaa tttgacgggg   1080
tgcaatctgc tggagatgac agagtacttg taatgggtgc aactaacagg ccccaagagc   1140
ttgatgaagc tgttctcagg cgtttcatta acgggtata tgtgtcctta ccaaatgagg    1200
agacaagact ccttctgctt aaaaacctgt tgtgtaaaca aggaagtcca ctgacccaaa   1260
aagaactcgc acagcttgct agaatgaccg atggatactc tggaagtgat ctgaccgctt   1320
tggccaagga tgcagccctg ggtcctatcc gagaactgaa gccagagcag gtgaagaata   1380
tgtctgccag tgagatgaga aatattcgat tatctgactt cacagaatcc ttaaaaaga    1440 taaaacgcag tgtgagtcct cagaccttag aagcatacat acgctggaac aaggattttg   1500
gagacaccac tgtttaaagg aatggatgcc tctgtgagcc catagaacat cgcacttcac   1560
aggaaacaag agctttggct acaggaaccc agacttcgtt tacaggacgt tttagagttt   1620
tcatttttgt gcaccaaact tgaagaggaa caagaagaca gacctaaata aaatatgcaa   1680
tatgaatgg                                                            1689

<210> SEQ ID NO 73
<211> LENGTH: 504
<212> TYPE: PRT
<213> ORGANISM: Mus musculus
<220> FEATURE:
<223> OTHER INFORMATION: Incomplete murine spastin.

<400> SEQUENCE: 73

Ala Glu Ser Val Arg Val Phe His Lys Gln Ala Phe Glu Tyr Ile Ser
 1               5                  10                  15

Ile Ala Leu Arg Ile Asp Glu Glu Glu Lys Ala Gly Gln Lys Glu Gln
            20                  25                  30
```

-continued

```
Ala Val Glu Trp Tyr Lys Lys Gly Ile Glu Glu Leu Glu Lys Gly Ile
         35                  40                  45
Ala Val Ile Val Thr Gly Gln Gly Glu Gln Tyr Glu Arg Ala Arg Arg
         50                  55                  60
Leu Gln Ala Lys Met Met Thr Asn Leu Val Met Ala Lys Asp Arg Leu
 65                  70                  75                  80
Gln Leu Leu Glu Lys Leu Gln Pro Val Leu Gln Phe Ser Lys Ser Gln
                 85                  90                  95
Thr Asp Val Tyr Asn Glu Ser Thr Asn Leu Thr Cys Arg Asn Gly His
                100                 105                 110
Leu Gln Ser Glu Ser Gly Ala Val Pro Lys Arg Lys Asp Pro Leu Thr
            115                 120                 125
His Ala Ser Asn Ser Leu Pro Arg Ser Lys Thr Val Leu Lys Ser Gly
        130                 135                 140
Ser Ala Gly Leu Ser Gly His His Arg Ala Pro Ser Cys Ser Gly Leu
145                 150                 155                 160
Ser Met Val Ser Gly Ala Arg Pro Gly Pro Gly Pro Ala Ala Thr Thr
                165                 170                 175
His Lys Gly Thr Pro Lys Pro Asn Arg Thr Asn Lys Pro Ser Thr Pro
                180                 185                 190
Thr Thr Ala Val Arg Lys Lys Lys Asp Leu Lys Asn Phe Arg Asn Val
            195                 200                 205
Asp Ser Asn Leu Ala Asn Leu Ile Met Asn Glu Ile Val Asp Asn Gly
        210                 215                 220
Thr Ala Val Lys Phe Asp Asp Ile Ala Gly Gln Glu Leu Ala Lys Gln
225                 230                 235                 240
Ala Leu Gln Glu Ile Val Ile Leu Pro Ser Leu Arg Pro Glu Leu Phe
                245                 250                 255
Thr Gly Leu Arg Ala Pro Ala Arg Gly Leu Leu Leu Phe Gly Pro Pro
                260                 265                 270
Gly Asn Gly Lys Thr Met Leu Ala Lys Ala Val Ala Ala Glu Ser Asn
            275                 280                 285
Ala Thr Phe Phe Asn Ile Ser Ala Ala Ser Leu Thr Ser Lys Tyr Val
        290                 295                 300
Gly Glu Gly Glu Lys Leu Val Arg Ala Leu Phe Ala Val Ala Arg Glu
305                 310                 315                 320
Leu Gln Pro Ser Ile Ile Phe Ile Asp Glu Val Asp Ser Leu Leu Cys
                325                 330                 335
Glu Arg Arg Glu Gly Glu His Asp Ala Ser Arg Arg Leu Lys Thr Glu
                340                 345                 350
Phe Leu Ile Glu Phe Asp Gly Val Gln Ser Ala Gly Asp Asp Arg Val
        355                 360                 365
Leu Val Met Gly Ala Thr Asn Arg Pro Gln Glu Leu Asp Glu Ala Val
        370                 375                 380
Leu Arg Arg Phe Ile Lys Arg Val Tyr Val Ser Leu Pro Asn Glu Glu
385                 390                 395                 400
Thr Arg Leu Leu Leu Leu Lys Asn Leu Leu Cys Lys Gln Gly Ser Pro
                405                 410                 415
Leu Thr Gln Lys Glu Leu Ala Gln Leu Ala Arg Met Thr Asp Gly Tyr
            420                 425                 430
Ser Gly Ser Asp Leu Thr Ala Leu Ala Lys Asp Ala Ala Leu Gly Pro
        435                 440                 445
```

```
Ile Arg Glu Leu Lys Pro Glu Gln Val Lys Asn Met Ser Ala Ser Glu
    450                 455                 460

Met Arg Asn Ile Arg Leu Ser Asp Phe Thr Glu Ser Leu Lys Lys Ile
465                 470                 475                 480

Lys Arg Ser Val Ser Pro Gln Thr Leu Glu Ala Tyr Ile Arg Trp Asn
                485                 490                 495

Lys Asp Phe Gly Asp Thr Thr Val
            500
```

<210> SEQ ID NO 74
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 74 atttttatt ttaaagcagg acag                                    24

<210> SEQ ID NO 75
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 75 aattttttc tttcaggtga acag                                    24

<210> SEQ ID NO 76
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 76
cttctctgtt gcatagagaa gatg                                   24

<210> SEQ ID NO 77
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 77 acttttcct tgtcagaaag tgga                                    24

<210> SEQ ID NO 78
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 78
ttttgtatcc tttaagggta ctcc                                   24

<210> SEQ ID NO 79
<211> LENGTH: 24
<212> TYPE: DNA
<213> ORGANISM: Homo sapiens
<220> FEATURE:
<223> OTHER INFORMATION: SPG4 gene splice acceptor site.

```
<400> SEQUENCE: 79
aggtcttgtt tcttagtgga acag                                              24

<210> SEQ ID NO 80
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 80
agtatatatt ttttagttgt tcac                                              24

<210> SEQ ID NO 81
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 81
cttgtgattt ttaaaggcta aagc                                              24

<210> SEQ ID NO 82
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 82
taatgctttg ttttaggtgg gaga                                              24

<210> SEQ ID NO 83
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 83
cttgtatttc ctctagatga agtt                                              24

<210> SEQ ID NO 84
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 84 gatttttgc ttgtaggtac agtc                                               24

<210> SEQ ID NO 85
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 85 ggatttttt ttttaggcgt ttca                                               24

<210> SEQ ID NO 86
```

```
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 86
ttttaatatt tttcagacaa gact                                          24

<210> SEQ ID NO 87
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 87
tccttccctt cctcagaatg actg                                          24

<210> SEQ ID NO 88
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 88
cttttatgtt ttacagaact aaaa                                          24

<210> SEQ ID NO 89
<211> LENGTH: 24
<212> TYPE: DNA
<213> ORGANISM: Homo sapiens
<220> FEATURE:
<223> OTHER INFORMATION: SPG4 gene splice acceptor site.

<400> SEQUENCE: 89 cttttaaaa atctagatga gaaa                                           24

<210> SEQ ID NO 90
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 90
tgagaaaggt aactaggggg ctgg                                          24

<210> SEQ ID NO 91
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 91
aggacaaggt aagattgtat ttgt                                          24

<210> SEQ ID NO 92
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 92
```

```
acttctaggt atcaattaat gtat                                        24

<210> SEQ ID NO 93
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 93
ccagtcaggt gggtttaggt taac                                        24

<210> SEQ ID NO 94
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 94
ctcataaggt attctgggac agta                                        24

<210> SEQ ID NO 95
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 95
gtggacaagt aagttttgcc atct                                        24

<210> SEQ ID NO 96
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 96
ggcctgaggt aagaacttta tatt                                        24

<210> SEQ ID NO 97
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 97
caatgctggt aagggttctc ttca                                        24

<210> SEQ ID NO 98
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 98
caaaatacgt gagtgctctg tttc                                        24

<210> SEQ ID NO 99
<211> LENGTH: 24
<212> TYPE: DNA
```

-continued

```
<213> ORGANISM: Homo sapiens
<220> FEATURE:
<223> OTHER INFORMATION: SPG4 gene splice donor site.

<400> SEQUENCE: 99
ttttataggt aagaacatat tttc                                          24

<210> SEQ ID NO 100
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 100
ttgatggtgt aagtgttgat tatg                                          24

<210> SEQ ID NO 101
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 101
gttctcaggt agggagattt atat                                          24

<210> SEQ ID NO 102
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 102
atgaggaggt atgtatctgt gttt                                          24

<210> SEQ ID NO 103
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 103
cttgctaggt gagtaatttg gatt                                          24

<210> SEQ ID NO 104
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 104
tatccgaggt aggtatacaa gagc                                          24

<210> SEQ ID NO 105
<211> LENGTH: 24
<212> TYPE: DNA
<213> ORGANISM: Homo sapiens
<220> FEATURE:
<223> OTHER INFORMATION: SPG4 gene splice donor site.

<400> SEQUENCE: 105
ccagtgaggt atagtatttt acaa                                          24
```

-continued

<210> SEQ ID NO 106
<211> LENGTH: 2152
<212> TYPE: DNA
<213> ORGANISM: Mus musculus
<220> FEATURE:
<223> OTHER INFORMATION: Complete Spg4 DNA

<400> SEQUENCE: 106

| | | | | | |
|---|---|---|---|---|---|
| gctcccgggc | tccggcgggc | gcgcgagcgg | ctccgtgggc | ccccgccgcc | gcagtggcag | 60 |
| tggccgccgc | cgccgcttgg | tcgccgtcgg | tctgcgggaa | gcgggttatg | gcggcggcgg | 120 |
| cagtgggagc | tgtgaatgag | ttctccggcc | ggacgacgga | agaagaaagg | ctcgggcggc | 180 |
| gcgagcccgg | cgcccgccag | gcctccgccc | ccgccgcgg | tccccgcccc | tgccgccggc | 240 |
| ccggcccctg | cggccggctc | gccgcctaag | cggaacctgt | cttctttctc | gtcccgctg | 300 |
| gtcgtcggct | tcgccctgct | gcgcctgctg | gcctgccacc | tggggctcct | cttcgcgtgg | 360 |
| ctctgccagc | gcttctcccg | cgccctcatg | gccgccaaga | ggagctccgg | gaccgcgccg | 420 |
| gcgcccgcct | cgccctcgcc | cccagcgccc | ggaccgggtg | gcgaggccga | gagcgtccgc | 480 |
| gtcttccaca | gcaggccttc | cgagtacatc | tccattgccc | tgcgcatcga | cgaggaagag | 540 |
| aaagcaggac | agaaggaaca | agctgtggaa | tggtataaga | aggtatcga | agaactggaa | 600 |
| aaggaatcg | ctgttatagt | tacgggccaa | ggtgaacagt | atgaaagagc | tagacgtctt | 660 |
| caagccaaaa | tgatgactaa | tttagttatg | gccaaggacc | gtttacaact | tctagagaag | 720 |
| ctgcaaccag | ttttgcaatt | ttccaagtca | cagacgacg | tctataacga | gagtactaac | 780 |
| ctgacatgcc | gcaatggaca | tctccagtca | gaaagtggag | cagttccgaa | gaggaaagac | 840 |
| cccttaacac | atgctagtaa | ttcattgcct | cgatcaaaaa | ctgtcctgaa | aagtggctcc | 900 |
| gcagggctct | ccggtcacca | cagggcgcct | agttgcagtg | gtttgtccat | ggtttctgga | 960 |
| gcaagaccgg | gacctggtcc | tgcagctacc | acacataagg | gtactccaaa | accaaataga | 1020 |
| accaacaaac | cttctactcc | cacaactgca | gttcggaaaa | agaaagactt | gaaaaatttt | 1080 |
| aggaatgtgg | acagcaatct | tgctaacctt | ataatgaatg | aaattgttga | caatgggaca | 1140 |
| gctgttaagt | ttgatgacat | agccgggcag | gagctggcaa | agcaagcgct | gcaggagatt | 1200 |
| gtcatccttc | cttctctgcg | gcctgagttg | ttcacagggc | tcagagctcc | tgctagaggc | 1260 |
| ttgttactct | tcggtccgcc | aggaaacgga | aaaacaatgc | tggctaaagc | agtagctgca | 1320 |
| gagtctaatg | cgacctttt | caacataagt | gctgccagtt | taacttcaaa | atatgtggga | 1380 |
| gaaggagaga | aattggtgag | agctctcttt | gctgtggctc | gagaacttca | accatctata | 1440 |
| atttttatag | atgaagttga | cagtcttttg | tgtgagagac | gggaagggga | gcacgacgct | 1500 |
| agcagacggc | taaagacgga | atttttaata | gaatttgacg | gggtgcaatc | tgctggagat | 1560 |
| gacagagtac | ttgtaatggg | tgcaactaac | aggccccaag | agcttgatga | agctgttctc | 1620 |
| aggcgtttca | ttaaacgggt | atatgtgtcc | ttaccaaatg | aggagacaag | actccttctg | 1680 |
| cttaaaaacc | tgttgtgtaa | acaaggaagt | ccactgaccc | aaaaagaact | cgcacagctt | 1740 |
| gctagaatga | ccgatggata | tctctggaagt | gatctgaccg | ctttggccaa | ggatgcagcc | 1800 |
| ctgggtccta | tccgagaact | gaagccgag | caggtgaaga | atatgtctgc | cagtgagatg | 1860 |
| agaaatattc | gattatctga | cttcacagaa | tccttaaaaa | agataaaacg | cagtgtgagt | 1920 |
| cctcagacct | tagaagcata | catacgctgg | aacaaggatt | ttggagacac | cactgtttaa | 1980 |
| aggaatggat | gcctctgtga | gcccatagaa | catcgcactt | cacaggaaac | aagagctttg | 2040 |

-continued

```
gctacaggaa cccagacttc gtttacagga cgttttagag ttttcatttt tgtgcaccaa   2100
acttgaagag gaacaagaag acagacctaa ataaaatatg caatatgaat gg            2152
```

<210> SEQ ID NO 107
<211> LENGTH: 614
<212> TYPE: PRT
<213> ORGANISM: Mus musculus
<220> FEATURE:
<223> OTHER INFORMATION: Complete murine spastin

<400> SEQUENCE: 107

```
Met Ser Ser Pro Ala Gly Arg Arg Lys Lys Lys Gly Ser Gly Gly Ala
 1               5                  10                  15

Ser Pro Ala Pro Ala Arg Pro Pro Pro Ala Ala Val Pro Ala Pro
            20                  25                  30

Ala Ala Gly Pro Ala Pro Ala Ala Gly Ser Pro Pro Lys Arg Asn Leu
         35                  40                  45

Ser Ser Phe Ser Ser Pro Leu Val Val Gly Phe Ala Leu Leu Arg Leu
     50                  55                  60

Leu Ala Cys His Leu Gly Leu Leu Phe Ala Trp Leu Cys Gln Arg Phe
 65                  70                  75                  80

Ser Arg Ala Leu Met Ala Ala Lys Arg Ser Gly Thr Ala Pro Ala
                 85                  90                  95

Pro Ala Ser Pro Ser Pro Ala Pro Gly Pro Gly Gly Glu Ala Glu
            100                 105                 110

Ser Val Arg Val Phe His Lys Gln Ala Phe Glu Tyr Ile Ser Ile Ala
        115                 120                 125

Leu Arg Ile Asp Glu Glu Glu Lys Ala Gly Gln Lys Glu Gln Ala Val
    130                 135                 140

Glu Trp Tyr Lys Lys Gly Ile Glu Glu Leu Glu Lys Gly Ile Ala Val
145                 150                 155                 160

Ile Val Thr Gly Gln Gly Glu Gln Tyr Glu Arg Ala Arg Arg Leu Gln
                165                 170                 175

Ala Lys Met Met Thr Asn Leu Val Met Ala Lys Asp Arg Leu Gln Leu
            180                 185                 190

Leu Glu Lys Leu Gln Pro Val Leu Gln Phe Ser Lys Ser Gln Thr Asp
        195                 200                 205

Val Tyr Asn Glu Ser Thr Asn Leu Thr Cys Arg Asn Gly His Leu Gln
    210                 215                 220

Ser Glu Ser Gly Ala Val Pro Lys Arg Lys Asp Pro Leu Thr His Ala
225                 230                 235                 240

Ser Asn Ser Leu Pro Arg Ser Lys Thr Val Leu Lys Ser Gly Ser Ala
                245                 250                 255

Gly Leu Ser Gly His His Arg Ala Pro Ser Cys Ser Gly Leu Ser Met
            260                 265                 270

Val Ser Gly Ala Arg Pro Gly Pro Gly Pro Ala Ala Thr Thr His Lys
        275                 280                 285

Gly Thr Pro Lys Pro Asn Arg Thr Asn Lys Pro Ser Thr Pro Thr Thr
    290                 295                 300

Ala Val Arg Lys Lys Lys Asp Leu Lys Asn Phe Arg Asn Val Asp Ser
305                 310                 315                 320

Asn Leu Ala Asn Leu Ile Met Asn Glu Ile Val Asp Asn Gly Thr Ala
                325                 330                 335

Val Lys Phe Asp Asp Ile Ala Gly Gln Glu Leu Ala Lys Gln Ala Leu
            340                 345                 350
```

-continued

```
Gln Glu Ile Val Ile Leu Pro Ser Leu Arg Pro Glu Leu Phe Thr Gly
            355                 360                 365

Leu Arg Ala Pro Ala Arg Gly Leu Leu Leu Phe Gly Pro Pro Gly Asn
    370                 375                 380

Gly Lys Thr Met Leu Ala Lys Ala Val Ala Ala Glu Ser Asn Ala Thr
385                 390                 395                 400

Phe Phe Asn Ile Ser Ala Ala Ser Leu Thr Ser Lys Tyr Val Gly Glu
                405                 410                 415

Gly Glu Lys Leu Val Arg Ala Leu Phe Ala Val Ala Arg Glu Leu Gln
            420                 425                 430

Pro Ser Ile Ile Phe Ile Asp Glu Val Asp Ser Leu Leu Cys Glu Arg
            435                 440                 445

Arg Glu Gly Glu His Asp Ala Ser Arg Arg Leu Lys Thr Glu Phe Leu
    450                 455                 460

Ile Glu Phe Asp Gly Val Gln Ser Ala Gly Asp Asp Arg Val Leu Val
465                 470                 475                 480

Met Gly Ala Thr Asn Arg Pro Gln Glu Leu Asp Glu Ala Val Leu Arg
                485                 490                 495

Arg Phe Ile Lys Arg Val Tyr Val Ser Leu Pro Asn Glu Glu Thr Arg
            500                 505                 510

Leu Leu Leu Leu Lys Asn Leu Leu Cys Lys Gln Gly Ser Pro Leu Thr
        515                 520                 525

Gln Lys Glu Leu Ala Gln Leu Ala Arg Met Thr Asp Gly Tyr Ser Gly
    530                 535                 540

Ser Asp Leu Thr Ala Leu Ala Lys Asp Ala Ala Leu Gly Pro Ile Arg
545                 550                 555                 560

Glu Leu Lys Pro Glu Gln Val Lys Asn Met Ser Ala Ser Glu Met Arg
                565                 570                 575

Asn Ile Arg Leu Ser Asp Phe Thr Glu Ser Leu Lys Lys Ile Lys Arg
            580                 585                 590

Ser Val Ser Pro Gln Thr Leu Glu Ala Tyr Ile Arg Trp Asn Lys Asp
        595                 600                 605

Phe Gly Asp Thr Thr Val
610
```